(12) United States Patent
True

(10) Patent No.: US 8,088,555 B2
(45) Date of Patent: Jan. 3, 2012

(54) MULTIPLE STEP PRINTING METHODS FOR MICROBARCODES

(75) Inventor: Randall True, San Francisco, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 12/779,420

(22) Filed: May 13, 2010

(65) Prior Publication Data

US 2010/0297336 A1  Nov. 25, 2010

Related U.S. Application Data

(63) Continuation of application No. 11/521,114, filed on Sep. 13, 2006, now Pat. No. 7,745,092.

(60) Provisional application No. 60/762,238, filed on Jan. 25, 2006, provisional application No. 60/716,694, filed on Sep. 13, 2005.

(51) Int. Cl.
  *G03F 7/00* (2006.01)
  *G03F 7/20* (2006.01)

(52) U.S. Cl. ............ 430/270.1; 430/311; 430/394; 430/396

(58) Field of Classification Search ........... 430/270.1, 430/5, 311, 330, 394, 396
See application file for complete search history.

(56) References Cited

U.S. PATENT DOCUMENTS

| | | | |
|---|---|---|---|
| 2,885,366 A | 5/1959 | Iler | |
| 3,772,200 A | 11/1973 | Livesay | |
| 4,053,433 A | 10/1977 | Lee | |
| 4,390,452 A | 6/1983 | Stevens | |
| 4,499,052 A | 2/1985 | Fulwyler | |
| 5,294,476 A | 3/1994 | Calhoun | |
| 5,766,829 A | 6/1998 | Cathey et al. | |
| 6,023,540 A | 2/2000 | Walt | |
| 6,355,432 B1 | 3/2002 | Fodor | |
| 6,416,949 B1 | 7/2002 | Dower | |
| 6,432,715 B1 | 8/2002 | Nelson et al. | |
| 6,576,424 B2 | 6/2003 | Fodor | |
| 6,647,649 B2 | 11/2003 | Hun | |
| 6,822,736 B2 | 11/2004 | Johnsen | |
| 6,908,737 B2 | 6/2005 | Ravkin | |
| 6,919,009 B2 | 7/2005 | Stonas | |
| 6,951,687 B2 | 10/2005 | Nightingale | |
| 7,015,047 B2 | 3/2006 | Huang | |
| 7,045,049 B1 | 5/2006 | Natan | |
| 7,106,513 B2 | 9/2006 | Moon | |
| 2001/0019401 A1 | 9/2001 | Irie | |
| 2002/0022124 A1 | 2/2002 | Ruoff | |

(Continued)

FOREIGN PATENT DOCUMENTS

JP  2008531423  4/2009

(Continued)

OTHER PUBLICATIONS

Bangs Labs, TechNote Covalent Coupling, Mar. 2003, pp. 1-9.

(Continued)

*Primary Examiner* — Amanda C. Walke
(74) *Attorney, Agent, or Firm* — Cooley LLP

(57) ABSTRACT

A system and method for forming encoded microparticles is described. One embodiment includes a method of forming an encoded microparticle, the method comprising: depositing and patterning a plurality of layers on a substrate so as to form a plurality of microparticles, each microparticle comprising a plurality of separate segments aligned along an axis and representing a code; and releasing the microparticles in order to separate the microparticles from the substrate.

24 Claims, 39 Drawing Sheets

U.S. PATENT DOCUMENTS

| | | |
|---|---|---|
| 2002/0084329 A1 | 7/2002 | Kaye |
| 2002/0137059 A1 | 9/2002 | Wu |
| 2002/0146745 A1 | 10/2002 | Natan |
| 2003/0006143 A1 | 1/2003 | Banerjee et al. |
| 2003/0119207 A1 | 6/2003 | Dejneka |
| 2003/0129654 A1 | 7/2003 | Ravkin |
| 2003/0153092 A1 | 8/2003 | Skinner et al. |
| 2003/0203390 A1 | 10/2003 | Kaye |
| 2004/0093187 A1 | 5/2004 | Dames |
| 2004/0125424 A1 | 7/2004 | Moon |
| 2004/0137729 A1 | 7/2004 | Norman |
| 2004/0146944 A1 | 7/2004 | Fang et al. |
| 2004/0175843 A1 | 9/2004 | Roltman |
| 2004/0209376 A1 | 10/2004 | Natan |
| 2004/0233485 A1 | 11/2004 | Moon |
| 2004/0263923 A1 | 12/2004 | Moon |
| 2005/0003180 A1 | 1/2005 | Kondos |
| 2005/0019842 A1 | 1/2005 | Prober |
| 2005/0042764 A1 | 2/2005 | Sailor |
| 2005/0089890 A1 | 4/2005 | Cubicciotti |
| 2006/0023310 A1 | 2/2006 | Putnam |
| 2006/0024732 A1 | 2/2006 | Hwang |
| 2006/0063271 A1 | 3/2006 | Putnam |
| 2007/0037195 A1 | 2/2007 | Ho |

FOREIGN PATENT DOCUMENTS

| | | |
|---|---|---|
| WO | WO-9639937 | 12/1996 |
| WO | WO-9715390 | 5/1997 |
| WO | WO-9941006 | 8/1999 |
| WO | WO-0016893 | 3/2000 |
| WO | WO-0126038 | 4/2001 |
| WO | WO-0178889 | 10/2001 |
| WO | WO-0264829 | 2/2002 |
| WO | WO-02083292 | 10/2002 |
| WO | 2003081261 | 10/2003 |
| WO | WO-03091731 | 11/2003 |
| WO | WO-2004011940 | 2/2004 |
| WO | WO-2004015418 | 2/2004 |
| WO | WO-2004046697 | 6/2004 |

OTHER PUBLICATIONS

Bayerl et al, Physical properties of single phospholipid bilayers absorbed to micro glass beads, Biophys. J., Aug. 1990, vol. 58, pp. 357-362.

Beaucage, Strategies in the preparation of DNA Oligonucleotide Army, Current Medicinal Chemistry, 2001, vol. 8, No. 10, pp. 1213-1244.

Buranda et al, Biomimetic Molecular Assemblies on Glass and Mesoporous Silica Microbeads for Biotechnology, Langmuir, Jan. 2003, vol. 19, No. 5, pp. 1654-1663.

Dejneka, et al., *Rare Earth-doped Glass Microbarcodes*, PNAS, Jan. 2003, vol. 100, No. 2, pp. 389-393.

Eastman et al, Qdot Nanobarcodes for Multiplexed Gene Expression Analysis, Nano letters, Apr. 2006, vol. 6, No. 5, pp. 1059-1064.

European Search Report, Application No. 06836128.6-2401, Oct. 23, 2009.

Evans et al, An encoded Particle Array Tool for Multiplexed Bioassays, Assay and Drug Development Technologies, 2003, vol. 1, No. 1-2, pp. 1-9.

Finkel et al, Barcoding The Microworld, Analytical Chemistry, Oct. 2004, pp. 353-359.

Gao et al, Quantum Dot-Encoded Mesoporous Beads with High Brightness and Uniformity: Rapid Readout Using Flow Cytometry, Analytical Chemistry, Apr. 2004, vol. 76, No. 8, pp. 2406-2410.

Gunderson et al, Decoding Random Ordered DNA Arrays, Genome Research, 2004, vol. 14, No. 5, pp. 870-877.

Iannone et al, Multiplexed Single Nucleotide Polymorphism Genotyping by Oligonucleotide Ligation and Flow Cytometry, Cytometry, 2000, 39, pp. 121-140.

McBride et al, Multiplexed Liquid Arrays for Simultaneous Detection of Simulants of Biological Warfare Agents, Analytical Chemistry, Apr. 2003, vol. 75, No. 8, pp. 1924-1930.

Nicewarner-Peña et al, Submicrometer Metallic Barcodes, Science, Oct. 2001, vol. 294, No. 5540, pp. 137-141.

Shendure et al, Accurate Multiplex Polony Sequencing of an Evolved Bacterial Genome, Science, Sep. 2005, vol. 309, pp. 1728-1732.

True, Randall J., et al.; *Microfabricated Templates for the Electrodeposition of Metallic Barcodes for use in Multiplexed Bioassays*; Proceedings of the 26th, Annual International Conference of the IEEE EMBS, Sep. 2004, pp. 2619-2622.

Vaino et al, Euclidean shape-encoded combinatorial chemical libraries, PNAS, Jul. 2000, vol. 97, No. 14, pp. 7692-7696.

Van Blaaderen et al, Synthesis and Characterization of Colloidal Dispersions of Fluorescent, Monodisperse silica Spheres, Langmuir, 1992, vol. 8, No. 12, pp. 2921-2931.

Vignali, Multiplexed particle-based flow cytometric assays, Journal of Immunological Methods, Sep. 2000, vol. 243, No. 1, pp. 243-255.

Walton et al, Particles for Multiplexed Analysis in Solution: Detection and Identification of Striped Metallic Particles Using Optical Microscopy, Analytical Chemistry . . . , May 2002, vol. 74, No. 10, pp. 2240-2247.

Yuen et al, Microbarcode Sorting Device, Lab on a Chip, Jul. 2003, vol. 3 No. 3 pp. 198-201.

Zhi et al, Micromachining Microcarrier-Based Biomolecular Encoding for Miniaturized and Multiplexed Immunoassay, Analytical Chemistry, Jul. 2003, vol. 75, No. 16, pp. 4125-4131.

Zhi, Zheng-Liang, et al.; *Microfabricated Addressable particles for Multianalyte Immunoassay*; School of Materials Science, Japan Advanced Institute of Science and Technology; 2003 IEEE, pp. 411-414.

Final Office Action dated Mar. 22, 2011 for U.S. Appl. No. 11/521,058, Inventor-TRUE, Filing Date-Sep. 13, 2006.

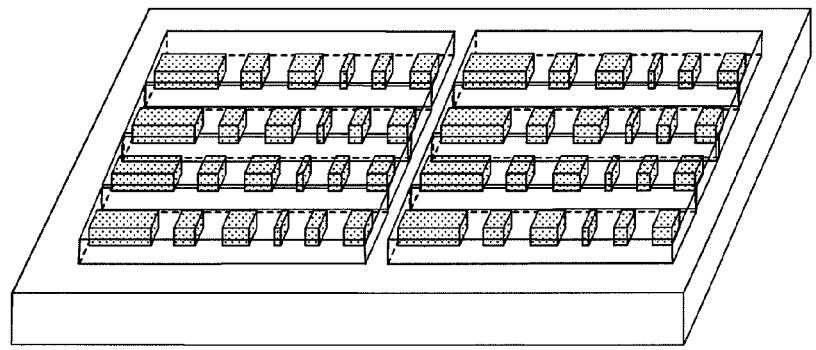
FIG. 8
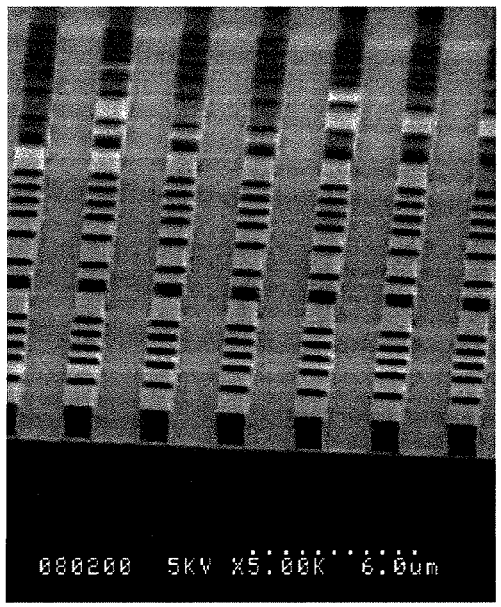 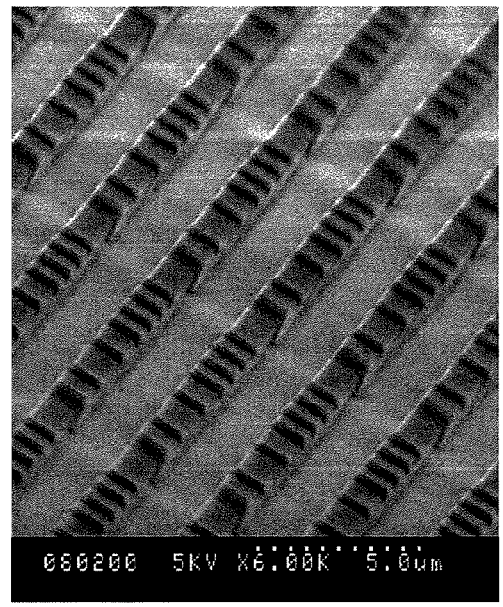
FIG. 9a  FIG. 9b

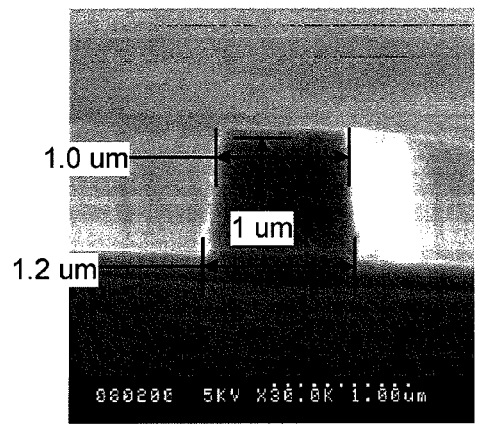 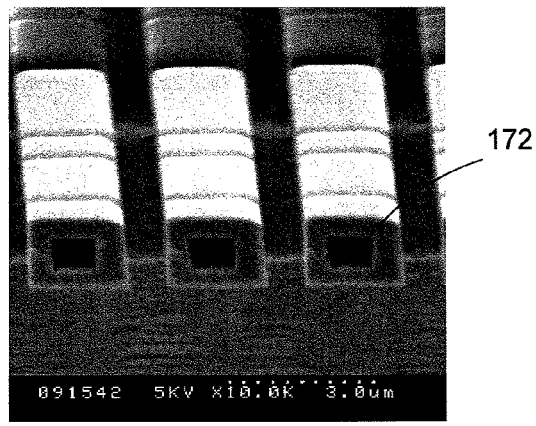
FIG. 9c          FIG. 10a
 
 
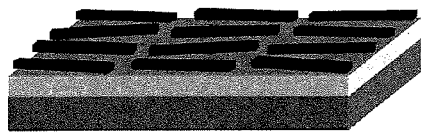 
FIG. 11a          FIG. 11b

 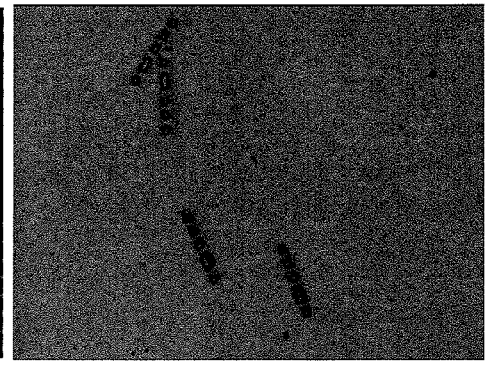
FIG. 12a  FIG. 12b
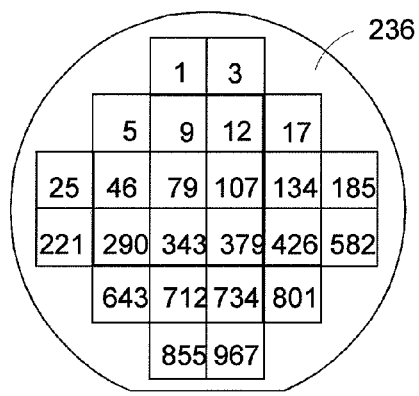
FIG. 13a
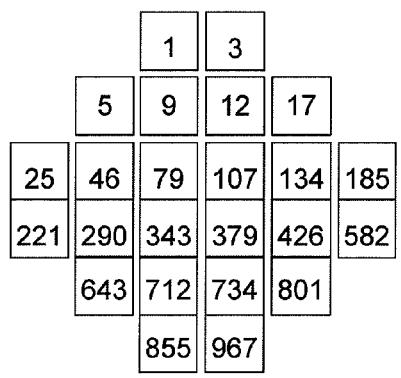
FIG. 13b
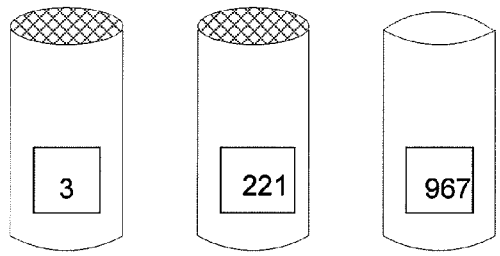
FIG. 13c 80um

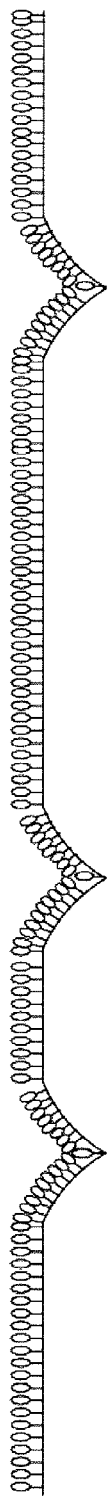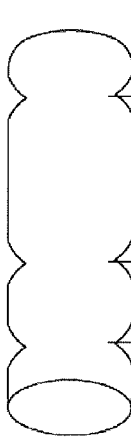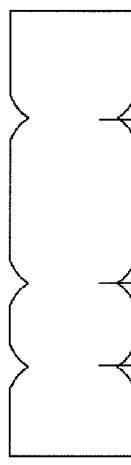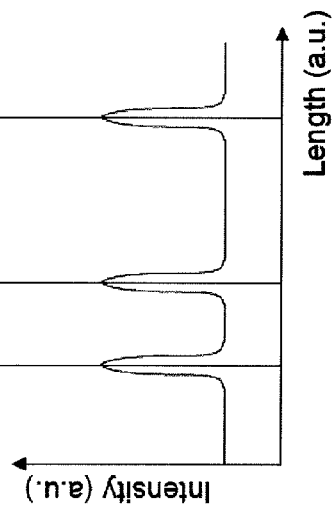
FIG. 27d
FIG. 27a
FIG. 27b
FIG. 27c
FIG. 28a
FIG. 28b
FIG. 28c

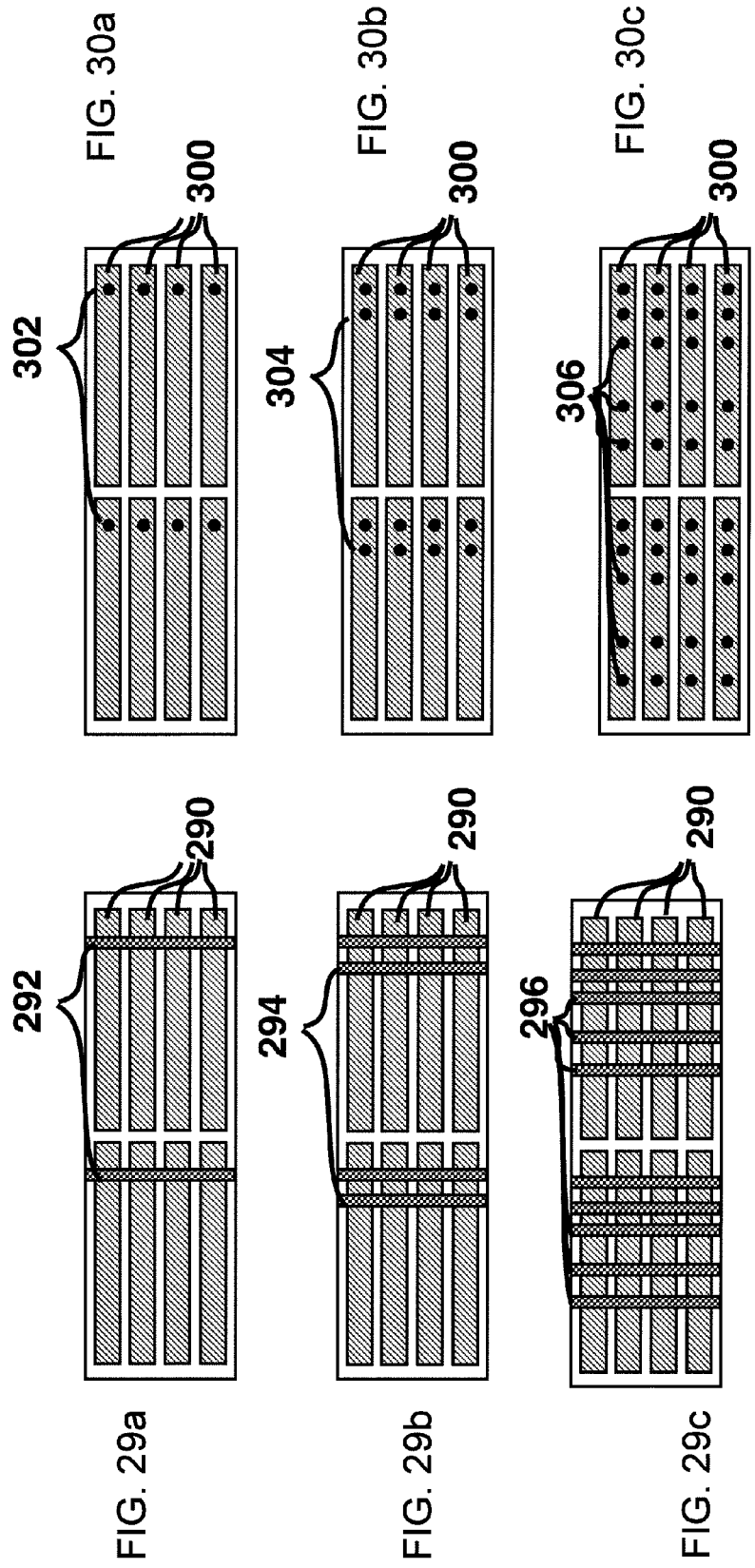

Code Pattern

Bar Pattern

Outline Pattern

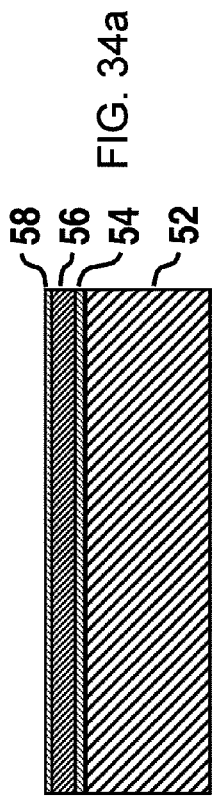
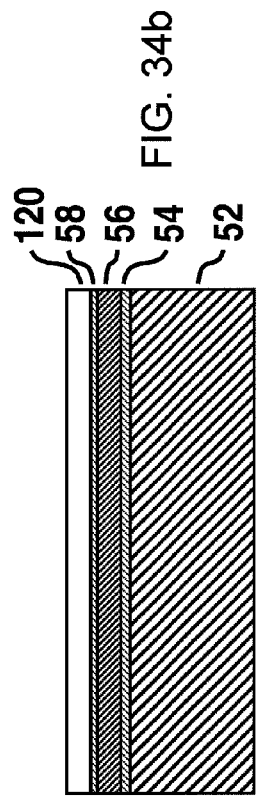
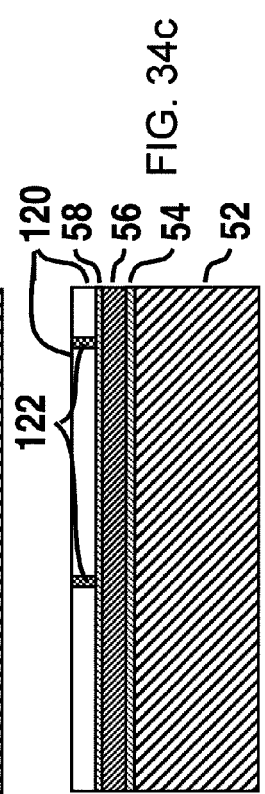
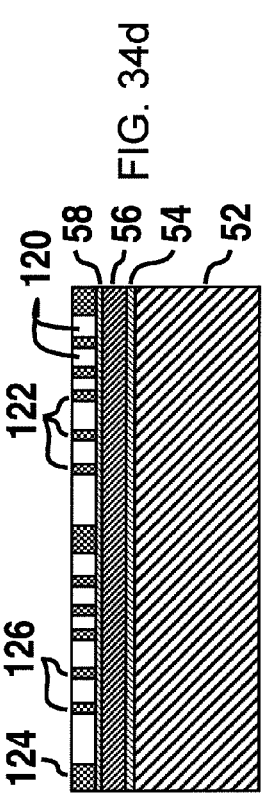
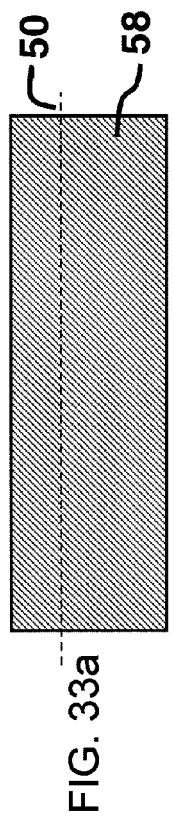
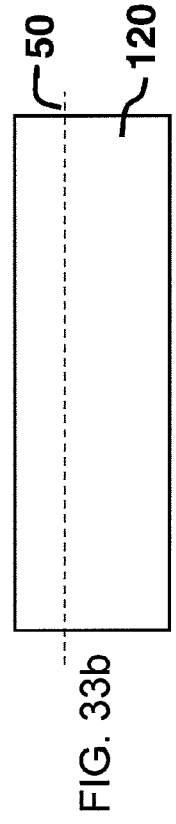
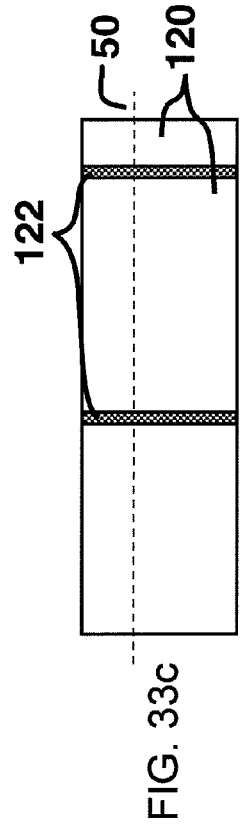
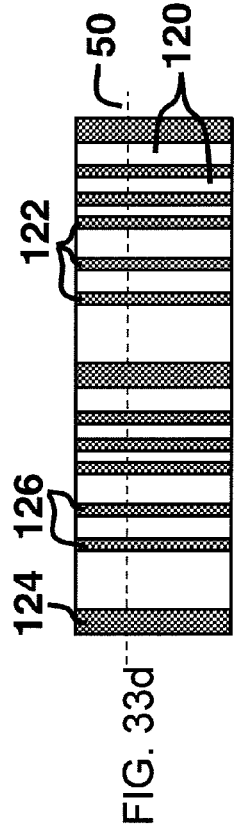

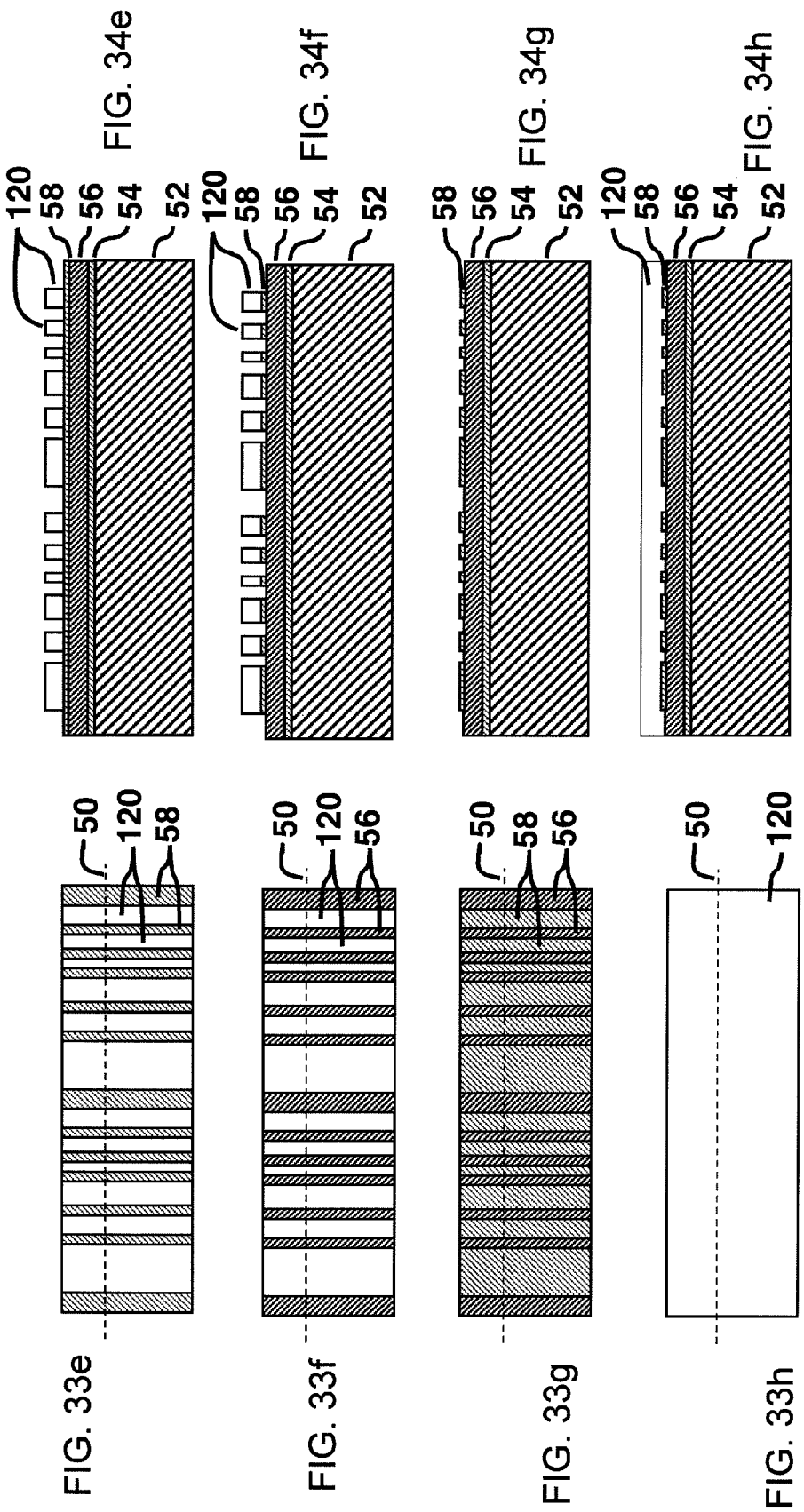

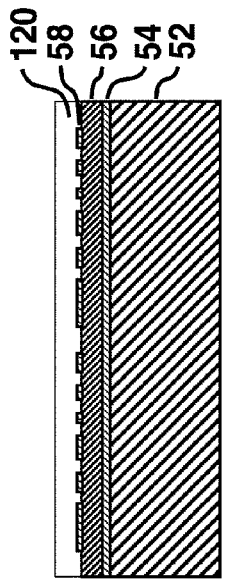
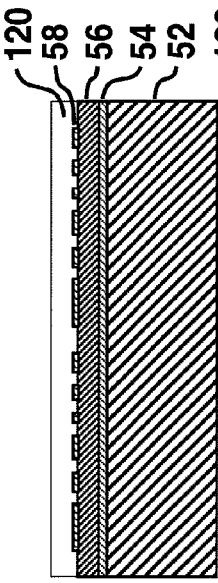
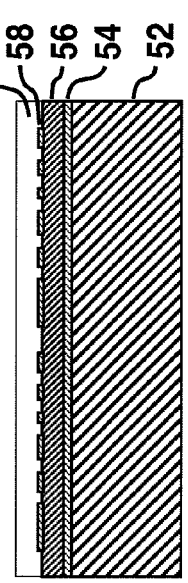
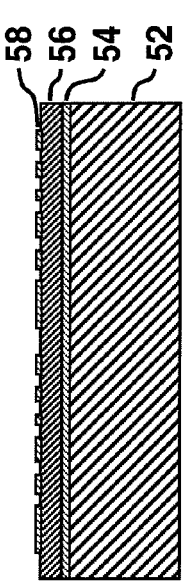
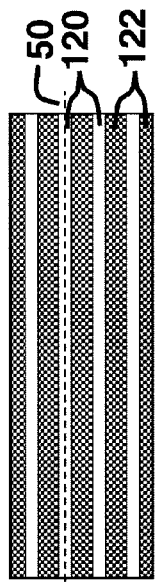
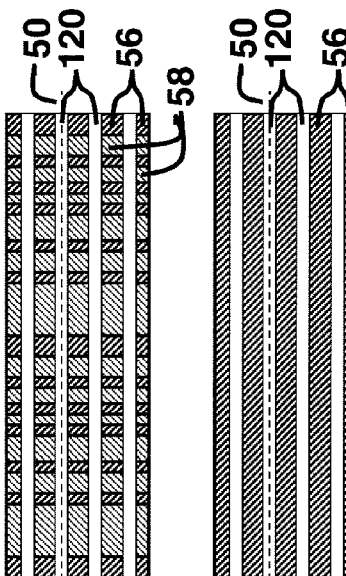
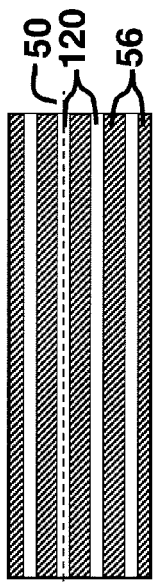
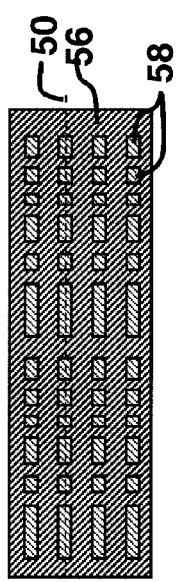

FIG. 37

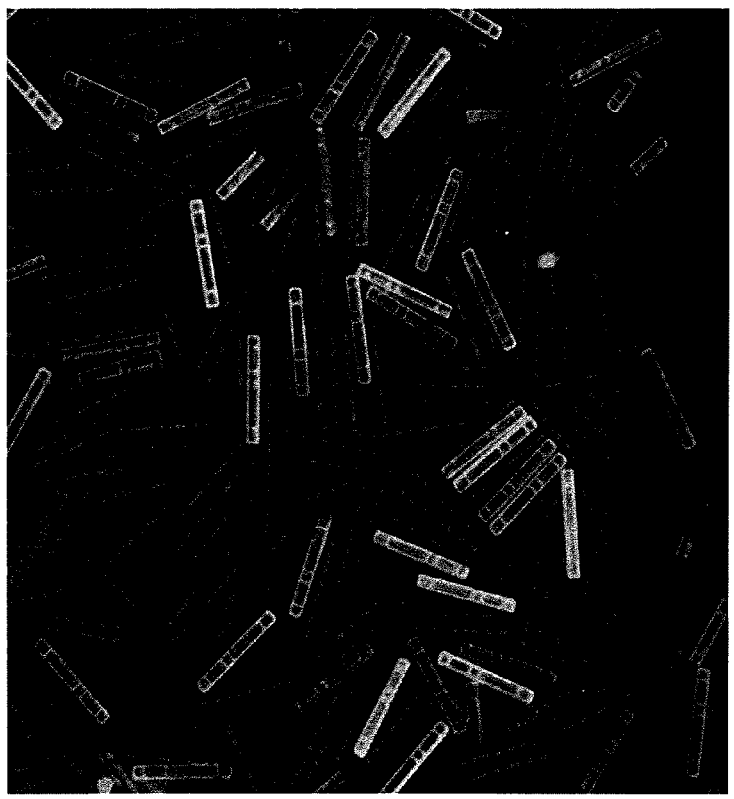
Probe1 & Probe2 + Target1    Probe1 & Probe2 + Target2
Code with 4 "cuts" – Probe1 5'/5AmMC6/AAA TCA TCG GGA GCA TTG TG-3'
                    Target1  3'-TTT AGT AGC CCT CGT AAC AC/5Cy3/5'
Code with 5 "cuts" – Probe2 5'/5AmMC6/AAC GCC TGG TCA CTG CTA TT-3'
                    Target2  3'-TTG CGG ACC AGT GAC GAT AA /5Cy3/5'
FIG. 48

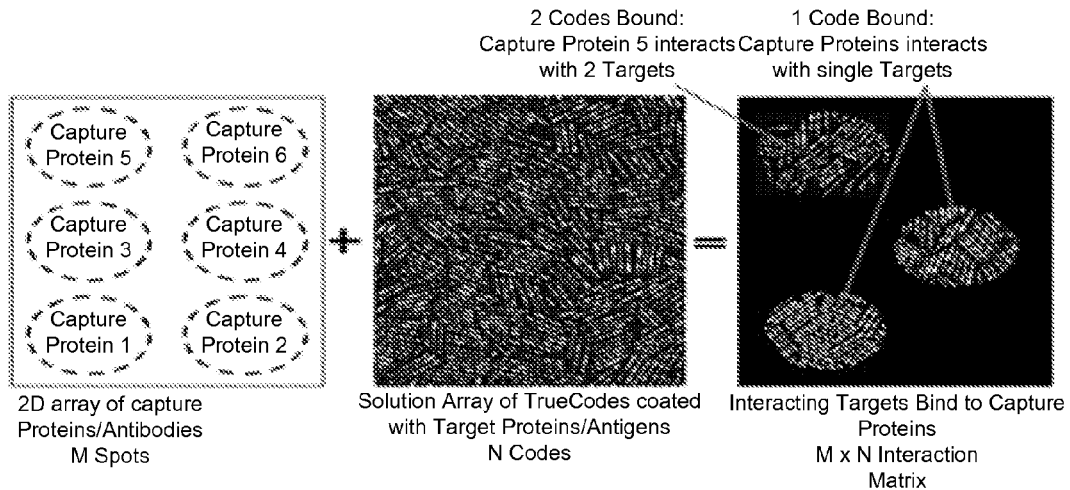
FIG. 51
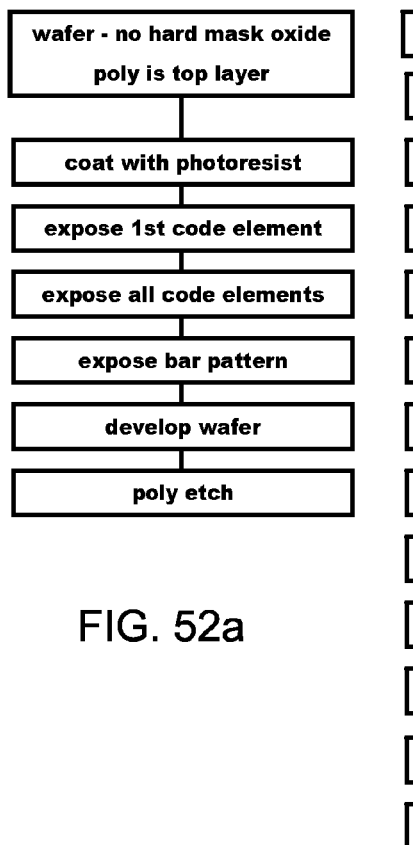
FIG. 52a
FIG. 52b
FIG. 52c

MULTIPLE STEP PRINTING METHODS FOR MICROBARCODES

CROSS-REFERENCE TO RELATED CASES

This US patent application is a continuation application of U.S. application Ser. No. 11/521,114, filed Sep. 13, 2006, now U.S. Pat. No. 7,745,092 which claims priority from U.S. provisional application Ser. No. 60/762,238, filed Jan. 25, 2006, and U.S. provisional application Ser. No. 60/716,694, filed Sep. 13, 2005, the subject matter of each being incorporated herein by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: AFFY_061_09US_SeqList_ST25.txt, date recorded: Jun. 30, 2010, file size 2 kilobytes).

TECHNICAL FIELD OF THE INVENTION

The present invention relates to the art of microstructures, and more particularly to encoded microparticles.

BACKGROUND OF THE INVENTION

Microparticles or nanoparticles are often referred to as structures whose characteristic dimensions are on the order of micrometers or less, such as those with volumes of 1 mm$^3$ or less. Due to their unique properties arising from their small characteristic dimensions, microparticles have found distinguishable applications in laboratory research and many industrial fields. Encoded microparticles possess a means of identification and are an important subclass of the general field of microparticles. Because encoded particles carry information and can be physically tracked in space and time, they greatly extend the capabilities of non-encoded particles. A particularly important application for encoded microparticles is multiplexed bioassays, including those involving DNA and proteins. Other important fields for encoded microparticles include combinatorial chemistry, tagging, etc. Many biochemical and non-biochemical applications as will be discussed herein below.

For many applications, one more desirable attributes include: a large number of identifiable codes (i.e. a high codespace), accurate and reliable identification of the encoded particles, material compatibility for a particular application, low cost manufacturing of the microparticles (on a per batch, per particle, and per code set basis), and flexibility in the detection systems.

Several approaches to produce encoded microparticles have been developed in the past, such as fragmented colored laminates, colored polystyrene beads, quantum dot loaded polymer beads, rare-earth doped glass microbarcodes, electroplated metal nano rods, diffraction grating based fiber particles, and pattern bars and disks, and other types of microparticles. These technologies however suffer from any of a number of limitations, such as, insufficient codespace, high cost, inadequate precision, poor performance in applications, problematic clumping incapability of large scale manufacture, and complicated preprocessing or assay procedures.

Therefore, what is desired is an encoded microparticle or a set of encoded microparticles carrying coded information, methods of making the same, methods for providing the codes for microparticles, methods for fabricating the microparticles, methods and systems for detecting microparticle, and methods and systems for using.

SUMMARY OF THE INVENTION

As an example of the invention, a method of forming an encoded microparticle is disclosed. The method comprises: depositing and patterning a layer on a substrate so as to form a plurality of microparticles, each comprising a plurality of separate segments aligned along an axis and representing a code; and releasing the microparticles in order to separate the microparticles from the substrate.

As another example of the invention, a method of producing an encoded particle is disclosed. The method comprises: providing a substrate; depositing a first layer on the substrate; depositing a second layer on the substrate; forming the second layer into a plurality of particle regions such that each particle region has two or more discrete segments aligned along an axis; depositing a third layer on the substrate; releasing the layers in the particle regions from the substrate to form individual particles; wherein a code is formed by the discrete segments of an individual particle.

As yet another example of the invention, a method of forming an encoded microparticle is disclosed. The method comprises: depositing and patterning a layer on a substrate so as to form a plurality of microparticles, each comprising a plurality of discrete segments aligned along an axis which is substantially parallel to the substrate and representing a code; and releasing the microparticles in order to separate the microparticles from the substrate, wherein the code for each microparticle is detectable from all directions perpendicular to the axis.

As still yet another example of the invention, a method of forming a plurality of encoded microparticles with a lithography process to define codes for identifying the particles is disclosed herein. The method comprises: providing a planar substrate on which the microparticles are to be formed; providing a $1^{st}$ pattern having a $1^{st}$ portion of an encoding pattern; exposing the substrate to the $1^{st}$ pattern, thereby printing the $1^{st}$ portion of the encoding pattern; providing a $2^{nd}$ pattern having a $2^{nd}$ portion of an encoding pattern; exposing the substrate to the $2^{nd}$ pattern, thereby printing the $2^{nd}$ portion of the encoding pattern; and wherein a complete encoding pattern is provided.

Such objects of the invention are achieved in the features of the independent claims attached hereto. Preferred embodiments are characterized in the dependent claims. In the claims, only elements denoted by the words "means for" are intended to be interpreted as means plus function claims under 35 U.S.C. §112, the sixth paragraph.

BRIEF DESCRIPTION OF DRAWINGS

While the appended claims set forth the features of the present invention with particularity, the invention, together with its objects and advantages, may be best understood from the following detailed description taken in conjunction with the accompanying drawings of which:

FIG. 1b is a side view cross-section of the microparticle in FIG. 1a;

FIG. 8 is a perspective view of an array of microparticles on a substrate during the fabrication;

FIG. 9a to FIG. 10 are SEM images of a plurality of microparticles during the fabrication of an exemplary fabrication method of the invention;

FIG. 11a and FIG. 11b illustrate an exemplary etching method that can be used in the fabrication method of the invention;

FIG. 12a and FIG. 12b are images of a plurality of microparticles of the invention;

FIG. 13a to FIG. 13c schematically illustrate an exemplary wafer level fabrication method according to an exemplary fabrication method of the invention;

FIGS. 27a to 27c show schematic diagrams of encoded microparticles of the present invention with surface indentations that form a spatial code;

FIG. 27d shows an example of encoded microparticles comprising indentations;

FIGS. 28a to 28c show the non-uniform aerial density measured normal to the particle surface for corresponding particles in FIGS. 27a to 27c;

FIG. 29a to FIG. 30c are top views of microparticles according to another example of the invention during another exemplary fabrication of the invention;

FIG. 33a to FIG. 33m illustrate the microfabrication process steps of the example encoded microparticle of FIG. 1a;

FIG. 34a to FIG. 34m show the corresponding cross sectional views of the microparticle in FIG. 33a to FIG. 33m;

FIG. 37 shows charts of example data that is input into the stepper software to generate different codes on every die on a wafer;

FIG. 48 shows real assay data from a 2-plex DNA hybridization assay;

FIG. 51 is a schematic that includes images of particles but is not the result of an actual experiment of this invention; and FIGS. 52a to 52c show flowcharts of examples of the code element patterning and etch steps.

DETAILED DESCRIPTION OF EXEMPLARY EMBODIMENTS

An encoded microparticle is provided carrying a code, and a set of encoded microparticles are provided with distinguishable codes, wherein the codes comply with a pre-determined coding scheme. Preferably, the microparticles in the examples below have a volume of 1 mm$^3$ or less. The microparticle of the invention enables fast, precise and less complicated detection of the code. Methods for providing the codes on microparticles, methods for fabricating the microparticles, methods and systems for detecting the microparticle, and methods and systems for using the microparticles are also disclosed.

In the following, the invention will be discussed with reference to specific examples. It will be appreciated by those skilled in art that the following discussion is for demonstration purposes, and should not be interpreted as a limitation. Instead, other variations without departing from the spirit of the invention are also applicable.

Overall Structure of the Microparticle

Figure 1A:
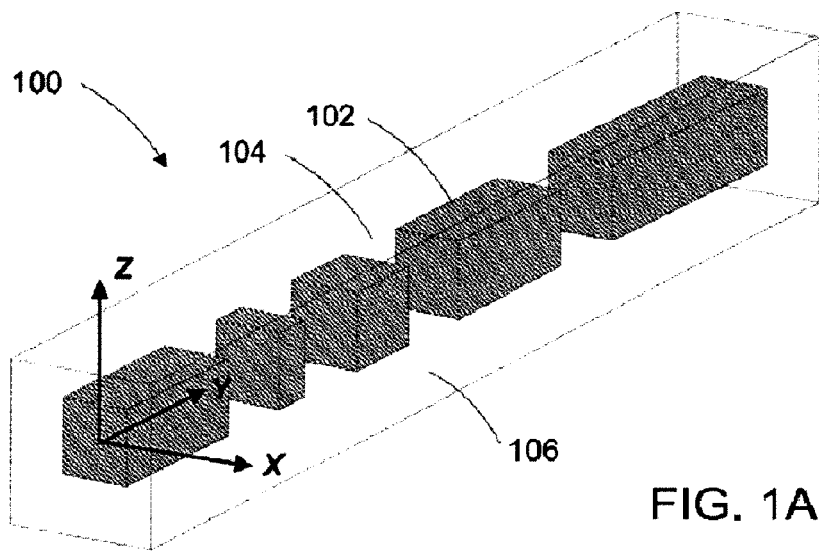
FIG. 1a schematically illustrates an encoded microparticle of the invention.

As an example, FIG. 1a schematically illustrates an encoded microparticle of the invention. Microparticle 100 is a cuboid structure elongated along the Y direction in the Cartesian coordinate as shown in the figure. The cross-sections perpendicular to the length of the microparticle have substantially the same topological shape—which is square in this example.

The microparticle in this particular example has a set of segments (e.g. segment 102) and gaps (e.g. gap 104) intervening the segments. Specifically, segments with different lengths (the dimension along the length of the microparticle, e.g. along the Y direction) represent different coding elements; whereas gaps preferably have the same length for differentiating the segments during detection of the microparticles. The segments of the microparticle in this example are fully enclosed within the microparticle, for example within body 106. As an alternative feature, the segments can be arranged such that the geometric centers of the segments are aligned to the geometric central axis of the elongated microparticle. A particular sequence of segments and gaps represents a code. The codes are derived from a pre-determined coding scheme.

Segments of the microparticle can be any suitable form. In an example of the invention, each segment of the microparticle has a substantially square cross-section (i.e. the cross-section in the X-Z plane of a Cartesian coordinate as shown in FIG. 1a) taken perpendicular to the length (i.e. along the Y direction in the Cartesian coordinate in FIG. 1a) of the microparticle. The segments may or may not be fabricated to have substantially square cross-section. Other shapes, such as rectangular, circular, and elliptical, jagged, curved or other shapes are also applicable. In particular, the code elements—i.e. segments and gaps, may also take any other suitable desired shape. For example, the segment (and/or the gaps) each may have a cross-section that is rectangular (e.g. with the aspect ratio of the rectangular being 2:1 or higher, such as 4:1 or higher, 10:1 or higher, 20:1 or higher, or even 100:1 or higher, but preferably less than 500:1).

The microparticle example of FIG. 1 A has six major surfaces, namely surfaces of (X=±$x_0$, Y, Z), surfaces (X, Y, Z=±$z_0$), and surfaces (X, Y=±$y_0$, Z), wherein $x_0$, $y_0$, and $z_0$ are respectively the width, length, and height of the microparticle. According to the invention, at least two of the above six surfaces X=±$x_0$ (or surfaces Z=±$z_0$), more preferably four of the above six major surfaces X=±$x_0$, surfaces Z=±$z_0$ are substantially continuous, regardless of whether each surface has or does not have indentations. With this configuration, the microparticle exhibits substantially the same geometric appearance and specific properties to the detector—such as an optical imaging apparatus. In fact, the major surfaces can be made substantially flat. For example, even though rough-ness or varying profiles may be caused during fabrication, substantially flat major surfaces can still be obtained using standard surface machining techniques, such as over-deposit and etch back or chemical-mechanical-polishing (CMP) techniques, as well as proper control of patterning steps to create smooth vertical sidewall profiles.

The code elements, i.e. the segments and gaps, may take any desired dimensions. As an example of the invention, each coding structure has a characteristic dimension that is 5 μm (microns) or less, such as 3 microns or less, and more preferably 1 micron or less, such as 0.8 or 0.5 microns or less. In particular, when gaps are kept substantially the same dimension while the segments vary in dimension, each gap preferably has a characteristic dimension that is 1.5 microns or less, such as 0.8 or 0.5 microns or less.

As one example, if forming the microparticles on a 12-inch silicon wafer with 0.13 line widths, the gap areas can be made to have 0.13 μm minimum widths, with the less transparent segments having widths of from 0.13 μm to much larger (depending upon the desired length of the particle and the encoding scheme and code space desired). Minimum gap widths, as well as minimum segment widths, of from 0.13 to 1.85 μm (e.g. from 0.25 to 0.85 μm) are possible depending upon the wafer fabrication used. Of course larger minimum gap and segment lengths (e.g. 1.85 to 5.0 μm, or more) are also possible. Other sized wafers (4 inch, 6 inch, 8 inch etc.) can of course be used, as well as wafers other than silicon (e.g. glass), as well as other substrates other than silicon (larger glass panels, for example).

Though the microparticle may have the same length in the X, Y and/or Z directions, preferably the encoded microparticle has a ratio of the length to width of from 2:1 to 50:1, e.g. from 4:1 to 20:1. In an example of the invention, the microparticle has a length (e.g. the dimension along the Y direction) of 70 microns or less, 50 microns or less, 30 microns or less, such as 20 microns or less, 16 microns or less, or even 10 microns or less. The width (e.g. the dimension along the X direction), as well as the height (the dimension along the Z direction), of the microparticle can be 15 microns or less, 10 microns or less, 8 microns or less, 4 microns or less, or even 1 microns or less, such as 0.13 micron. Widths as small as from 0.5 to 2 microns are also possible. Other than the shape as shown in FIG. 1a and discussed above, the microparticle may take a form of rod, bar, disk or any other desired shapes.

The coding structures and gaps of the microparticles can take any suitable form as long as the coding structures and gaps together represent detectable codes. As mentioned above, the cross-section of the microparticles, as taken perpendicular to the length of the particle, can be square, rectangular, circular, elliptical, or any desired shape such as jagged or curved shapes or other profiles. When the cross-section is rectangular, the rectangle preferably has an aspect ratio (the ratio of the length to the width or height) of 2:1 or higher, such as 4:1 or higher, 10:1 or higher, 20:1 or higher, or even 100:1 or higher, but preferably less than 500:1. The ratio of the width to height can be around 1:1 (square cross section), or have a ratio of from 1:4 to 1:1—preferably a ratio that allows the particle to rest on either the sides defining the width or height of the particle such that the code of the microparticle can be detected regardless of which of the elongated sides the particle rests.

To facilitate fast, cost-effective, reliable, and easy detection of the code represented by the coding structures and gaps, it is preferred that each coding structure is as omni-directional as possible to the detection means. That is—each coding structure exhibits substantially the same geometric appearance or detectable properties when observed from at least two directions, more preferably from four (or all, if not four-sided in cross section) directions perpendicular to the length of the microparticle. Accordingly, the coding structures preferably possess rotational symmetry along the length of the microparticle, such as 2-folded or 4-folded rotational symmetry.

A microparticle of the invention can have any suitable number of coding structures depending upon the shape or length of the particle, and the code space desired. Specifically, the total number of coding structures of a microparticle can be from 1 to 20, or more typically from 3 to 15, and more typically from 3 to 8.

The desired code can be incorporated in and represented by the microparticle in many ways. As an example, the coding elements of the pre-determined coding scheme can be represented by the segment(s)—e.g. segments of different lengths represent different coding elements of the coding scheme. Different spatial arrangements of the segments with the different (or the same) lengths and intervened by gaps represent different codes. In this code-incorporation method, the intervening gaps preferably have substantially the same dimension, especially the length in the direction to which the segments are aligned. As another example, the codes are incorporated in the microparticle by arranging gaps that vary in lengths; while the segments have substantially the same dimension and are disposed between adjacent gaps. In another example, the both segments and gaps vary in their dimensions so as to represent a code. In fact, the code can also be represented in many other alternative ways using the segments, gaps, and the combination thereof.

For representing a code derived from the predetermined coding scheme, the segments and gaps are arranged along the length (the Y direction) of the elongated microparticle (2D, or even 3D, arrangements however are also possible). Specifically, the segments and gaps are alternately aligned along the length with the each segment being separated (possibly fully separated and isolated) by adjacent gaps; and each gap is separated (possibly fully separated and isolated) by adjacent segments, which is better illustrated in a cross-sectional view in FIG. 1b, which will be discussed in the following.

In an example of the invention, any suitable number of segments can be used—e.g. from 2 to 20, or more typically from 3 to 15 segments (more typically from 3 to 8 segments) of less transparent material (as compared to the intervening gaps between the segments) are provided within the encoded microparticle. To form the code, it is possible that the segments of less transparent material are varying lengths. Alternatively, the segments of less transparent material could each have substantially the same length whereas the intermediate segments of more transparent material could have varying lengths. Of course, the segments of more transparent material and the intermediate segments of less transparent material could both have varying lengths in order to represent the code.

Figure 1B:
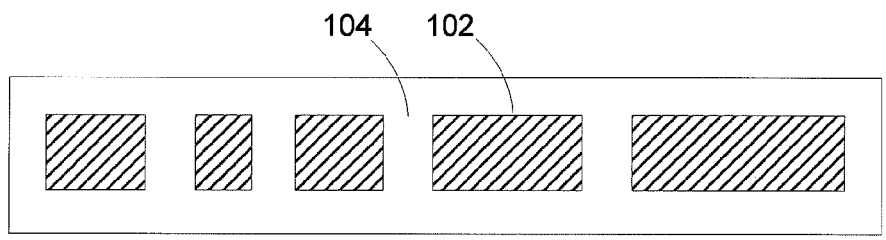

Referring to FIG. 1b, the cross-section is taken in the Y-Z plane (or equivalently in the X-Y plane) of the particle in FIG. 1a. Segments (e.g. segment 102) and gaps (e.g. gap 104) alternate along the length of the microparticle.

In order to enable detection of codes incorporated in microparticles, the segments and gaps in each microparticle can be composed of materials of different optical, electrical, magnetic, fluid dynamic, or other desired properties that are compatible with the desired detection methods. In one example the segments and gaps are directly spatially distinguishable under transmitted and/or reflected light in the visible spectrum. For example, when the code detection relies upon optical imaging, the distinguishable property (segments vs. gaps) can be a difference in transmissivity to the particular light used for imaging (which can be any desired electromagnetic radiation—e.g. visible and near-visible light, IR, and ultraviolet light. The segments can be made to be more light absorbing (or light reflecting) than the intervening spacing material (or vice versa). When the code detection relies upon the electrical property measurements, the property can be resistance and conductance. When the code detection involves magnetic methods, the properties can be inductance and electro-inductance. When the code detection involves fluid dynamic methods, the property can be viscosity to the specific fluid used in the code detection. Regardless of which specific property is relied upon, the segments and gaps are preferred to exhibit sufficient difference in the specific property such that the difference is detectable using the corresponding code detection method. In particular, when the code is to be detected by means of optical imaging, the segments and gaps are composed of materials exhibiting different transmissivity (in an optical transmittance mode) or reflectivity (in optical reflectance mode) to the specific light used in imaging the microparticles. For example, the segments of the microparticle of the less transparent material can block and/or reflect 30% or more, preferably 50% or more, or e.g. 80% or more, of the visible light or near visible light incident thereon.

Given the fact that transmissivity of electromagnetic radiation through an object varies with the thickness of the object, it is preferred that the segments that are capable of blocking and/or reflecting 30% or more, preferably 50% or more, or e.g. 80% or more (or even 90% or more), of the detection light; while the gaps between the coding structures are provided from materials and at dimensions that are capable of transmitting 50% or more, 70% or more, 80% or more, or even 90% or more of the detecting light. Alternatively, the segments and gaps are composed of different materials such that the ratio of the transmissivity difference is sufficient to detect the code, e.g. is 5% or more, 10% or more, 20% or more, 50% or more, and 70% or more. The transmissivity is defined as the ratio of the light intensities of the passed light to the incident light.

The microstructure can be made of organic and/or inorganic materials or a hybrid of organic and inorganic material. Specifically, the gaps (which are preferably more transmissive to visible or near-visible light) and segments (which are preferably less transmissive to visible or near-visible light as compared to gaps) each can be composed organic or inorganic materials, or a hybrid organic-inorganic material. The segments can be composed of a metal (e.g. aluminum), an early transition metal (e.g. tungsten, chromium, titanium, tantalum or molybdenum), or a metalloid (e.g. silicon or germanium), or combinations (or nitrides, oxides and/or carbides) thereof. In particular, the segments can be composed of a ceramic compound, such as a compound that comprises an oxide of a metalloid or early transition metal, a nitride of a metalloid or early transition metal, or a carbide of a metalloid or early transition metal. Early transition metals are those from columns 3b (Sc, Y, Lu, Lr), 4b (Ti, Zr, Hf, Rf), 5b (V, Nb, Ta, Db), 6b (Cr, Mo, W, Sg) and 7b (Mn, Tc, Re, Bh) of the periodic table. However, preferred are early transition metals in columns 4b to 6b, in particular tungsten, titanium, zirconium, hafnium, niobium, tantalum, vanadium and chromium.

The gaps which are in this example more transparent, can comprise any suitable material that is more transparent than the segments. The spacing material can be a siloxane, siloxene or silsesquioxane material, among others, if a hybrid material is selected. The spacing material, if inorganic, can be a glass material. Thin film deposited silicon dioxide is a suitable material, with or without boron or phosphorous doping/alloying agents. Other inorganic glass materials are also suitable such as silicon nitride, silicon oxynitride, germanium oxide, germanium oxynitride, germanium-silicon-oxynitride, or various transition metal oxides for example. A spin on glass (SOG) could also be used. If an organic material is used for the gap material, a plastic (e.g. polystyrene or latex for example) could be used.

Both the segments and the gaps can be deposited by any suitable methods such as CVD (chemical vapor deposition), PVD (physical vapor deposition), spin-on, sol gel, etc. If a CVD deposition method is used, the CVD could be LPCVD (low pressure chemical vapor deposition), PECVD (plasma enhanced chemical vapor deposition), APCVD (atmospheric pressure chemical vapor deposition), SACVD (sub atmospheric chemical vapor deposition), etc. If a PVD method is used, sputtering or reactive sputtering are possible depending upon the desired final material. Spin on material (SOG or hybrid organic-inorganic siloxane materials As a more specific example, the segments can be comprised of any suitable silicon material such as CVD (chemical vapor deposition) deposited amorphous silicon. Polysilicon or single crystal silicon area also suitable as are a wide range of other materials as mentioned above. It is preferred, but not necessary, that the material selected for the segments has a high degree of deposition thickness control, low surface roughness, control of etching—both patterning and release (e.g. using a dry plasma etch for patterning and a wet or dry chemical etch for release), and CMOS process compatibility. The gap material can be CVD deposited silicon dioxide. The silicon dioxide may include doping/alloying materials such as phosphorous or boron. Temperature considerations may be taken into account in choosing a combination of more and less transparent materials for the segments and gaps.

Figure 2:
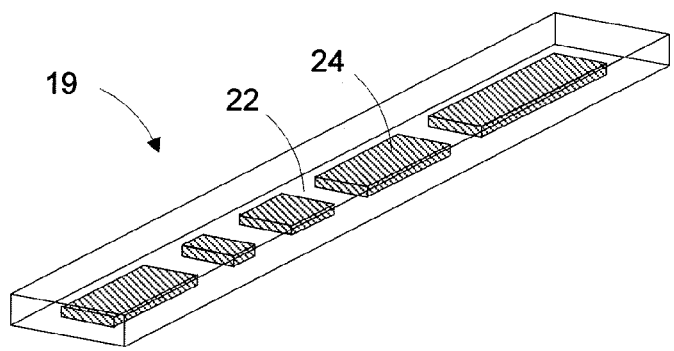
FIG. 2 schematically illustrates another example encoded microparticle of the invention.

FIG. 2 schematically illustrates another example encoded microparticle of the invention. Particle 20 has a rectangular cross section and is of a substantially flat shape. For example the ratio of the height to the width of the microparticle can be any desired ratio, e.g. can be from 1:1.2 to 1:4 or more, etc.

Figure 3A:
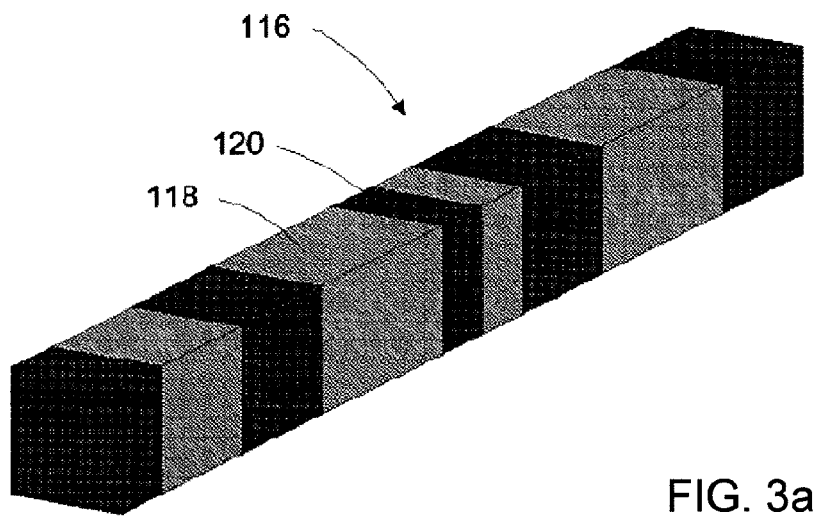
FIG. 3a schematically illustrates another example encoded microparticle of the invention.

FIG. 3a schematically illustrates another example encoded microparticle of the invention. Referring to FIG. 3a, microparticle 116 is composed of a $1^{st}$ material 118 and $2^{nd}$ material 120. The two materials can be chemically different or have the same chemical composition but be different in another respect such as grain structure or thickness. The two materials are distinguishable with the desired detection scheme. In this example each material preferably fully traverses the cross section of the particle. An example process for creating this structure involves fabrication methods as described, including those from the IC/MEMS (Integrated Circuit/Micro-Electro-Mechanical Systems) fields, including variations on the patterning and etching methods disclosed herein below, and/or with high energy ion implantation.

Figure 3B:
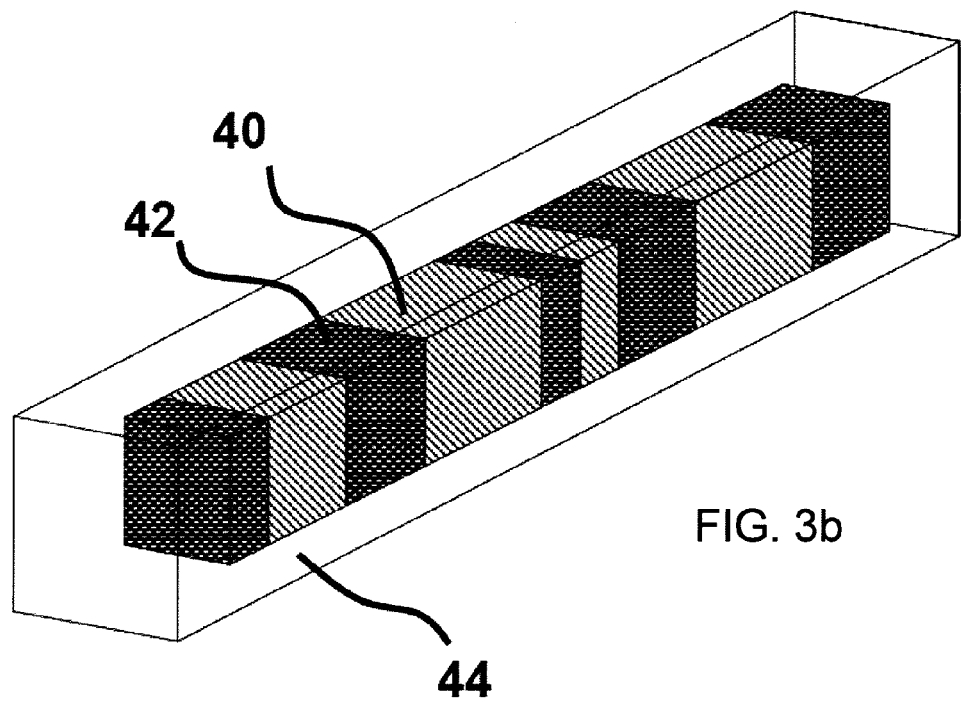
FIG. 3b schematically illustrates an another example encoded microparticle of the invention.

FIG. 3b schematically illustrates another example encoded microparticle of the invention. Referring to FIG. 3b, the microparticle is comprised of alternating segments of two different materials 40 and 42 that are surrounded by a third material 44, whereby the pattern of alternating segments forms a detectable code. Other example microparticles may contain more than two different materials in the interior of the particle. The particle may have any suitable cross sectional shape and in the example shown, is elongated.

Figure 4A:
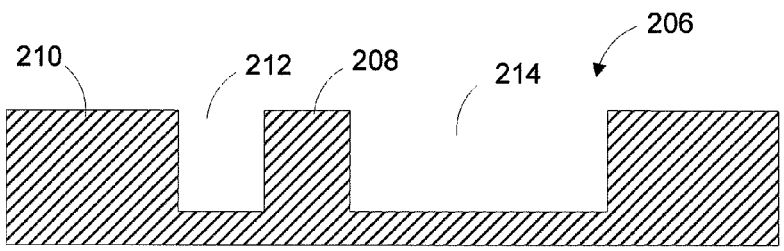
FIG. 4a and FIG. 4b schematically illustrates an exemplary microparticle whose coding structures are derived from a single material.
Figure 4B:
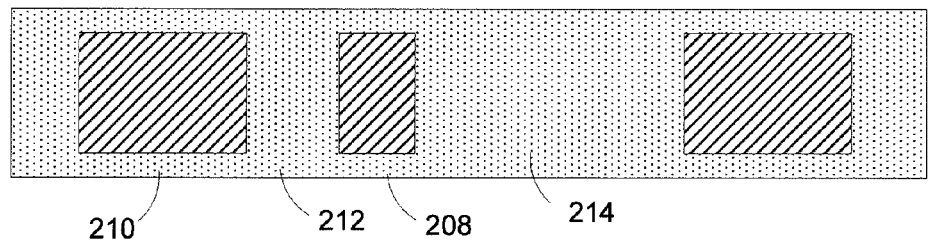

In the examples as discussed above, the microparticle is composed of materials of selected distinguishable properties, such as distinguishable optical properties. In the example above, one material has a greater transparency or optical transmissivity than the other material, which difference is detectable under magnification. A specific example of the above is where one material is a light absorbing material, and the other material is a translucent or transparent material with greater light transmittance in the visible spectrum (or in another spectrum should a different detection system be used—e.g. UV, IR etc). In another example, one material is a light reflecting material whereas the other material is either light absorbing or light transmitting. A detectable difference where one material is more opaque and the other material is less opaque, or where one material is more reflective and the other material is less reflective, are within the scope of this example. As mentioned above, the alternating portions of opaque and transparent materials can be made of silicon and glass among other materials. Given the fact that transmissivity (and reflectivity) of almost all materials exhibit dependencies from the thickness of the material, the microparticle may be formed such that the coding structures (i.e. the structures representing coding elements of a code) are derived from a single material. FIG. 4a and FIG. 4b schematically illustrates an exemplary microparticle whose coding structures are derived from a single material, such as silicon.

Referring to FIG. 4a wherein a cross-sectional view of an exemplary microparticle is illustrated therein. Microparticle 206 comprises a set of coding structures (e.g. 210, 212, 208, and 214), the combination of which represents a code derived from a coding scheme. For incorporating the code, the coding structures have different profiles, such as widths while different structures with different widths are positioned at particular locations. For defining the coding structure and code detection afterwards, a set of gaps (e.g. gaps 212 and 214) with thicknesses less than the transmissivity threshold thickness (the threshold below which the material is visible to the particular light such as visible and near-visible light). Different from the example as shown in FIG. 1a, the coding structures are not fully separated or isolated. The code incorporated in the microparticle can be read based on the different transmissivity of the coding structure (e.g. 210 and 208) which, for example, are less transmissive than the adjacent gaps (e.g. 212 and 214) between the coding structures.

For facilitating the application of the microparticles, especially biological/biochemical/biomedical/biotechnology applications wherein the sample bio-molecules are to be attached to the surfaces of the microparticles, an immobilization layer may be desired to be coated on the surfaces of the microstructures.

Figure 4C:
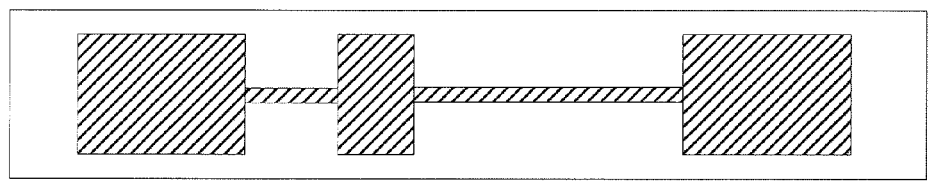
FIG. 4c schematically illustrates an another example encoded microparticle of the invention.

FIG. 4b schematically illustrates a transmissive-mode image of the microparticle in FIG. 4a. Referring to FIG. 4b, dark regions 210, 208 respectively correspond to the coding structures 210 and 208 in FIG. 4a. White regions 212 and 214 respectively correspond to the coding structures 212 and 214 in FIG. 4a. Even though the material used in the more light transmitting and less light transmitting sections is the same, the transmittance profile can still allow for a detectable code. Such a microparticle in FIG. 4a can be formed with a bottom layer of another material (e.g. silicon dioxide), and be coated with a second layer of another material (e.g. silicon dioxide) if desired. Such a microparticle can also be fully encased in a material (e.g. silicon dioxide) such that it has substantially the same rectangular parallel piped shape as the structure in FIG. 1a. FIG. 4c schematically illustrates another example encoded microparticle of the invention. Referring to FIG. 4c, the microparticle comprises larger regions connected by narrower regions. The microparticle is surrounded by a material such that a code is detectable.

Figure 4D:
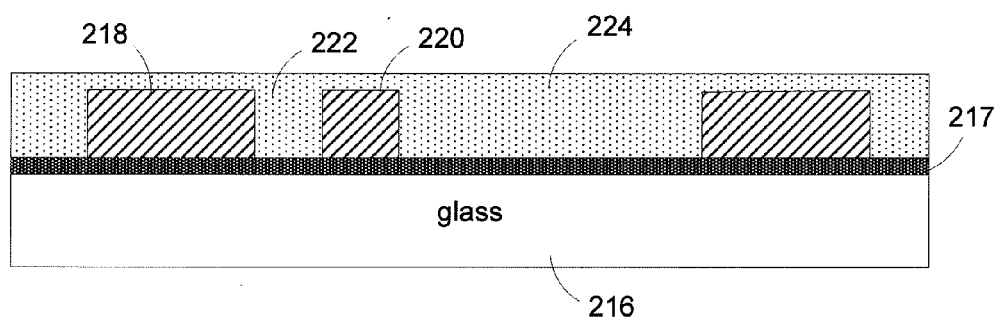
FIG. 4d is a cross-sectional view of another exemplary microparticle during an exemplary fabrication of the invention.

The microparticle of FIG. 4a and FIG. 4c can be fabricated in many ways, one of which is schematically demonstrated in a cross-sectional view of the microparticle during the exemplary fabrication in FIG. 4d. Referring to FIG. 4d, substrate 216 composed of material (e.g. glass, quartz, or other suitable materials) that is transmissive to a particular light (e.g. visible or near-visible light) is provided. Detaching layer 217 is deposited on substrate 216. The detaching layer is provided for detaching the microparticles from the glass substrate afterward by etching or other suitable methods. The etching can be wet, dry, or plasma etching; and the detaching layer is thus desired to be composed of a material etchable with the selected etching method, as discussed hereinabove. As described for previous embodiments of the particle structures, the detaching layer may be omitted such that the particle is formed directly on the substrate and is subsequently released by a bulk etch of the substrate.

A coding structure layer is deposited and patterned so as to form the coding structures, such as structures 218, 222, 220, 224. After forming the coding structures, surrounding layer 224 is deposited on the formed coding structures. Because the surrounding layer will be exposed to the target sample in the assay, it is desired that layer 224 is composed of a material that is resistant to chemical components in the assay solution wherein the microparticles are to be dispensed. Moreover, for holding the probe molecules, such as nucleic acids (e.g. DNA or RNA), proteins, antibodies, enzymes, drugs, receptors, or ligands, molecules on the surface of the layer, layer 224 is desired to be capable of immobilizing the probe molecules.

Fabrication Process

The following exemplary fabrication processes will be discussed in reference to microparticles with segments and gaps, however it should be noted that the following methods are applicable to many other types of code elements.

The microstructure of the invention can be fabricated with a method that fall into the broad field of micro-machining, such as MEMS fabrication methods. MEMS use the techniques of the semiconductor industry to form microscale structures for a wide variety of applications. MEMS techniques typically, but not in all circumstances, include the deposition of thin films, etching using dry and/or wet methods, and lithography for pattern formation. Because MEMS is an offshoot of the semiconductor industry, a vast worldwide manufacturing infrastructure is in place for cost-effective, high volume, precision production. Generally speaking, the more similar the full MEMS process is to existing integrated circuit processes, e.g. CMOS compatible, the more accessible this infrastructure is.

The microstructure of the invention can be fabricated in many ways, such as fabrication methods used for integrated circuits (e.g. interconnects) or MEMS. In the following, an exemplary fabrication method compatible with the MEMS fabrication for making a microparticle will be discussed with reference to FIG. 5 and FIG. 6a to FIG. 6m, wherein the microparticle comprises opaque segments that are composed of amorphous silicon, and visible light transmissive gaps that are comprised of silicon dioxide. It will be appreciated by those skilled in the art that the following fabrication discussion is for demonstration purposes only, and should not be interpreted as a limitation on the scope of the invention. In fact, many fabrication methods could be used without departing from the spirit of the invention.

Figure 5:
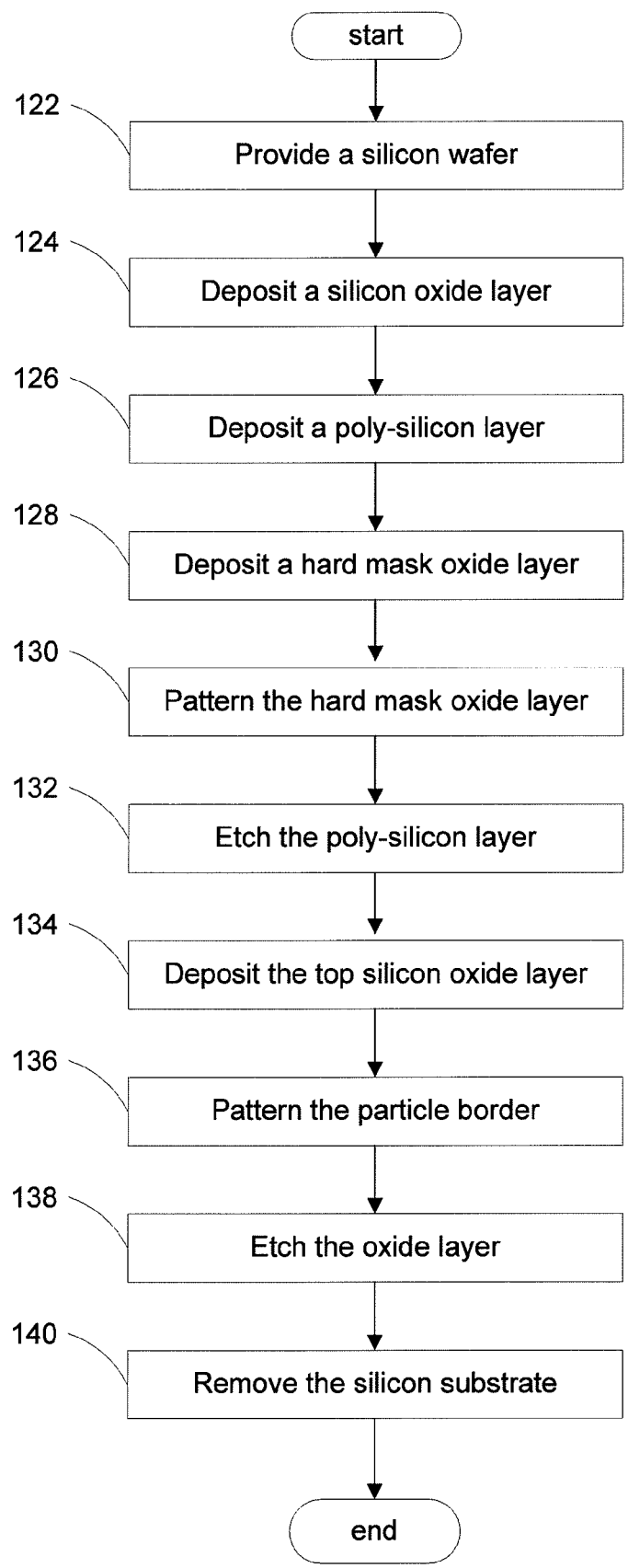
FIG. 5 is a flow chart showing the steps executed in an exemplary fabrication method of the invention.

Referring to FIG. 5, a silicon substrate is provided at step 122. Other substrates, such as glass wafers or glass panels could also be used (as will be discussed further herein below). Assuming a silicon substrate, on the substrate is deposited a silicon dioxide layer at step 124. The deposition can be performed with many suitable thin film deposition techniques, such as CVD, PVD, spin-on etc. as mentioned above. An amorphous silicon layer is then deposited on the $SiO_2$ layer at step 126 followed by deposition of a hard mask oxide layer at step 128. Though not needed, the use of a hard mask reduces photoresist coating problems cause by topology, particularly when the amorphous silicon layer is relatively thick (e.g. 1 µm or more in thickness). The hard mask oxide layer is then patterned at step 130. With the patterned hard mask layer, the amorphous silicon layer is etched with a plasma etch so as to form the desired pattern at step 132. A top $SiO_2$ layer is then deposited on the patterned silicon layer at step 134 followed by patterning the silicon dioxide layer at step 136 to form separate (but still unreleased) microparticles. Then the microparticles are released from the silicon substrate at step 140 by a non-direction silicon etch that etches into the silicon substrate and causes the microparticles to be separated as individual particles. The flow chart in FIG. 9 as discussed above can be better demonstrated in cross-sectional views and top views of the microparticle at different steps. The cross-sectional and top views are schematically illustrated in FIG. 6a to FIG. 6m.

Figure 6A:
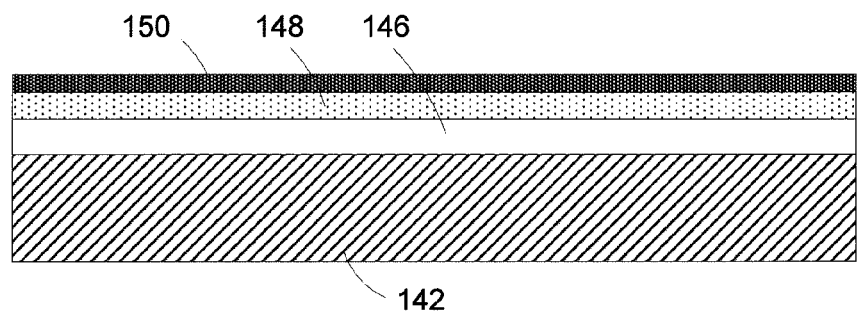
FIG. 6a to FIG. 6m are cross-section views and top views of a microparticle in an exemplary fabrication process of the invention.
Figure 6B:
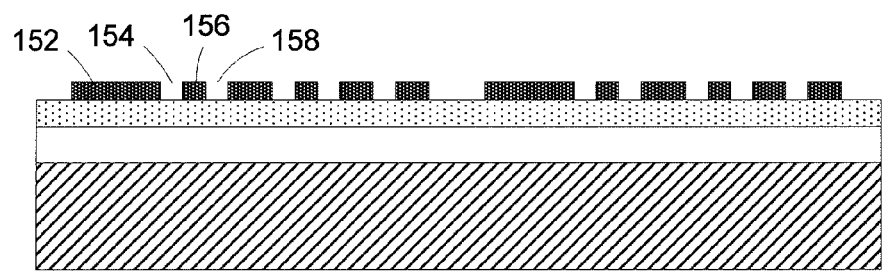
Figure 6C:
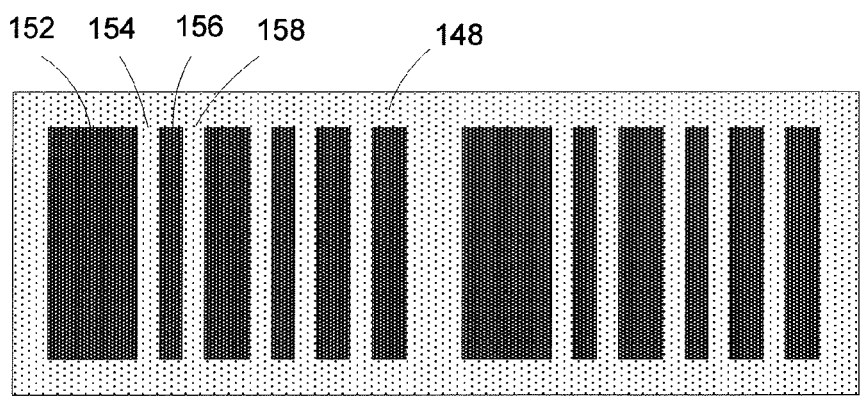

Referring to FIG. 6a, $SiO_2$ layer 146, silicon layer 148, and hard mask layer 150 are sequentially deposited on silicon substrate 142. Hard mask layer 150 is then patterned so as to form segment strips (e.g. 152 and 156) and gap strips (e.g. 154 and 158), as shown in FIG. 6b. The segment and gap strips formed from the patterning of the hard mask layer correspond to the segments and gaps of the target microparticle. The segment and gap strips are better illustrated in a top view of the microparticle in FIG. 6c. Referring to FIG. 6c, segment strips (e.g. 152 and 156) and gap strips (e.g. 154 and 158) are formed with layer 148 that is visible from the top.

The patterning of the layers can be done in many methods, one of which is photolithography that is widely used in standard fabrication for semiconductor integrated circuits and MEMS devices. The most common form of photolithography used in the MEMS industry is contact photolithography. A reticle (aka mask) is typically composed of a binary chrome pattern on a glass plate. The reticle is placed very near or in contact with a photoresist covered wafer (or other substrate). UV light is shone through the mask, exposing the photoresist. The wafer is then developed, removing the photoresist in the exposed regions (for positive-tone photoresist). The pattern on the reticle is thus transferred to the photoresist where it serves as a mask for a subsequent etching step.

Projection photolithography is another type of photolithography that is used exclusively in modern integrated circuit manufacturing. Instead of bringing the mask into physical contact, projection photolithography uses a system of lenses to focus the mask pattern onto the wafer. The primary advantage of this system is the ability to shrink the mask pattern through the projection optics. A typical system has a five times reduction factor. In general, much smaller feature sizes can be printed with projection as compared to contact lithography. A projection photolithography system is also known as a step-and-repeat system (or stepper for short). The maximum pattern or field size on the mask is significantly smaller than the wafer diameter. The mask pattern is repeatedly exposed ("stepped") on the wafer forming an array of "dies". The stepping distance is the distance the wafer stage travels in X and Y between exposures and is usually equal to the die size. This typical scheme produces a non-overlapping array of identical dies, allowing for subsequent parallel processing of the dies on the wafer.

Figure 6D:
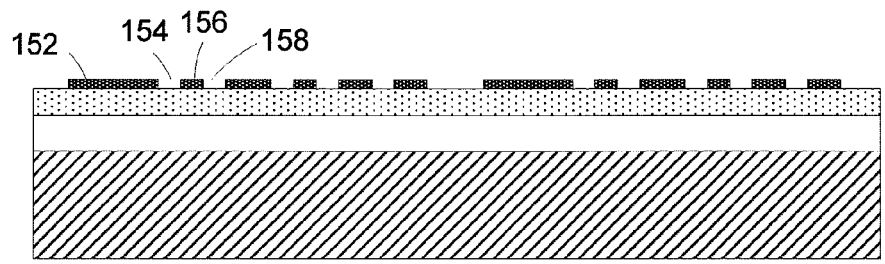
Figure 6E:
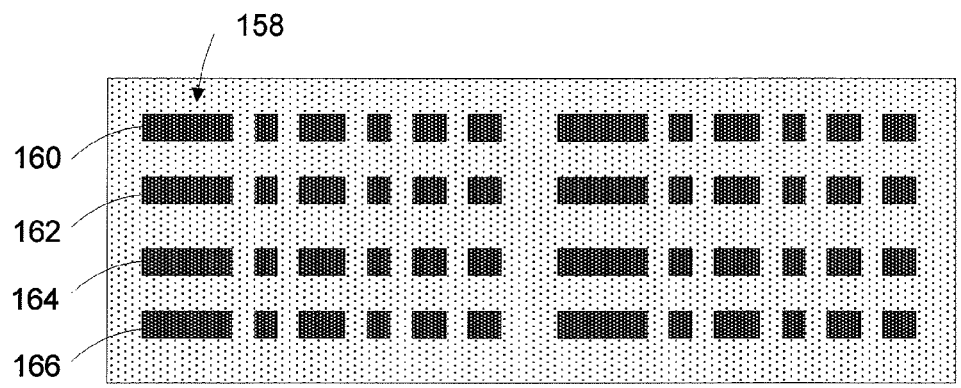

The hard mask layer (150) is further patterned so as to form discrete areas, as shown in FIG. 6d and FIG. 6e. As shown in FIG. 6d, the hard mask layer 150 is patterned in the X and Y directions so as to form discrete hard mask areas (e.g. areas 160, 162, 164, and 166 in FIG. 6e). These discrete hard mask areas will in turn be used to form discrete silicon areas in the layer below.

In the example above, the patterning of the hard mask layer is performed in two separate lithography steps. In an alternative example, the reticle may comprise a pattern such that the patterning of the hard mask can be accomplished with a single lithography step. As a further alternative, the hard mask can be omitted and either a two step or single step lithography process used.

Figure 6F:
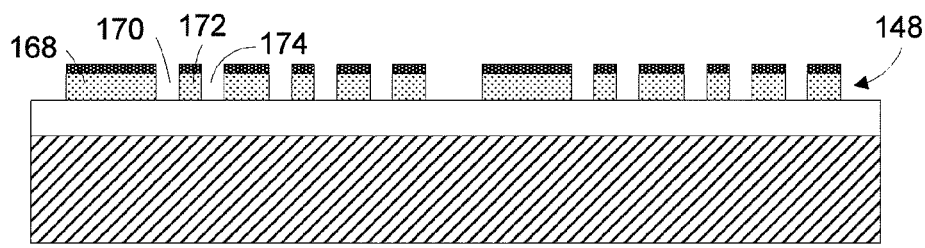
Figure 6G:
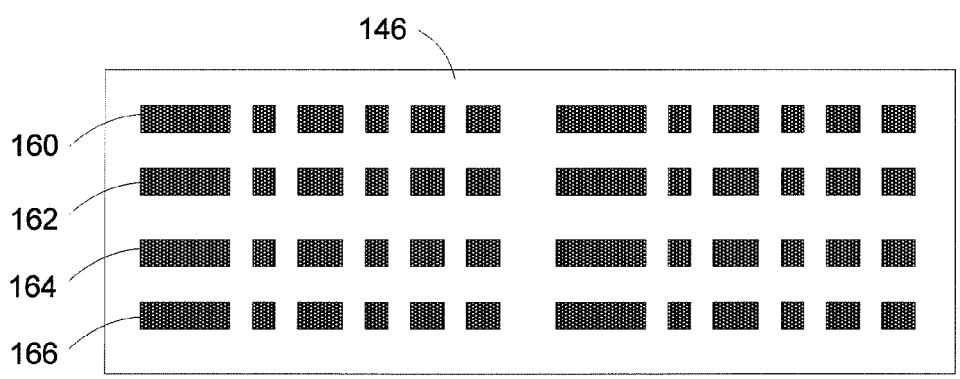

After patterning the top hard mask layer, silicon layer 148 is etched so as to form corresponding discrete silicon areas on the substrate, such as silicon segments 168 and 172, with areas there between for material of greater transparency (e.g. gap areas 170 and 172, as shown in FIG. 6f). The top view of the microparticle as shown in FIG. 6f is schematically illustrated in FIG. 6g. As seen in FIG. 6g, transmissive layer 146 is now exposed when viewed from the top, with segments 160, 162, 164, and 166 formed on transmissive layer 146. SEM images of the structures at this point in the fabrication process are shown in FIG. 9a and FIG. 9b. The structures have a very high degree of precision, e.g. vertical sidewalls and sharp corner. Of course more rounded structures are also in the scope of these methods.

Figure 6H:
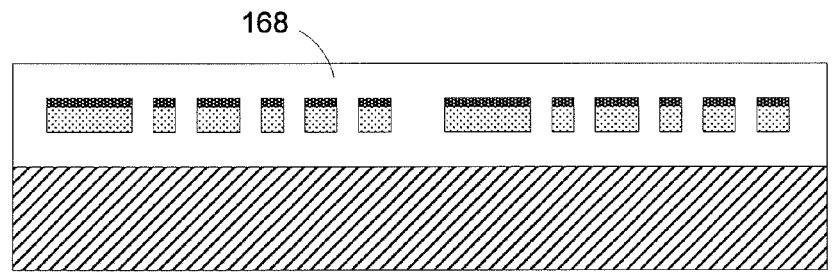
Figure 6I:
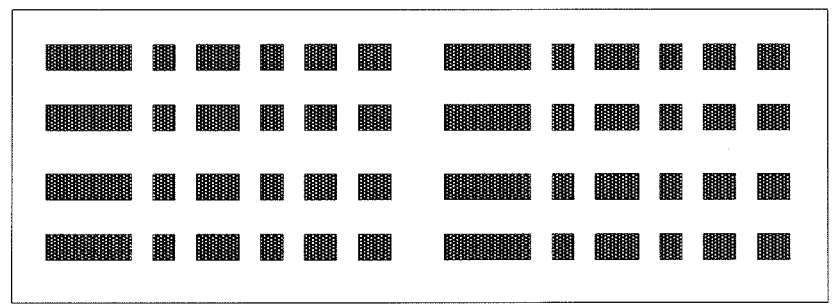
Figure 7:
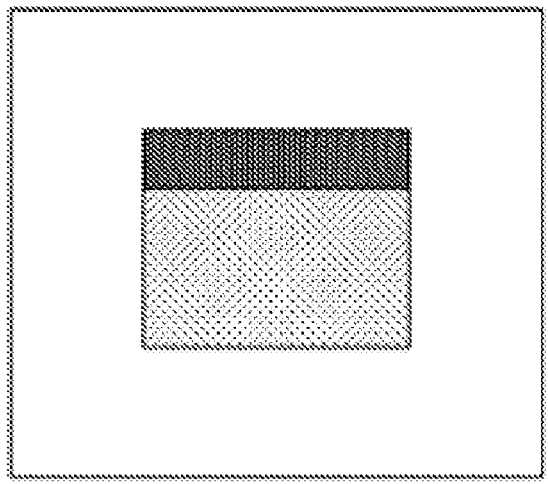
FIG. 7 is a cross section view of a microparticle from the exemplary fabrication process in FIG. 6a to FIG. 6m.

After patterning silicon layer 148, transmissive layer 168 is then deposited as shown in FIG. 6h. The more light transmissive layer 168 may or may not be composed of the same material as the more light transmissive layer 146. A top view of the microparticles in FIG. 6h is schematically illustrated in FIG. 6i. A cross section view of a microparticle is shown in FIG. 7. A perspective view of the particles on the substrate is shown in FIG. 8.

Figure 6J:
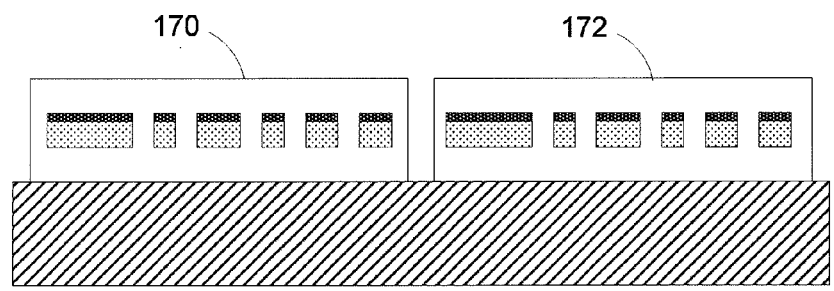
Figure 6K:
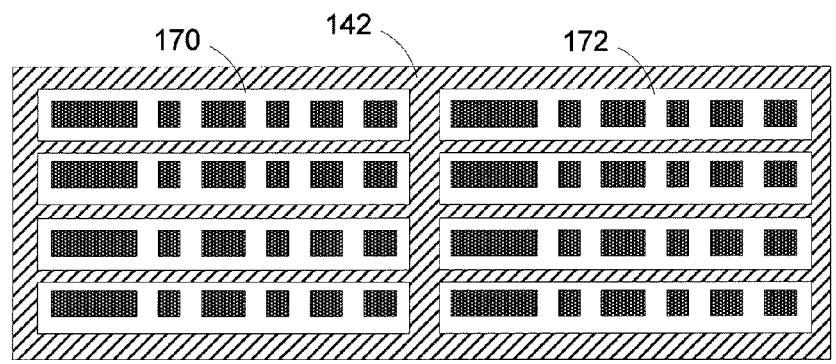
Figure 6L:
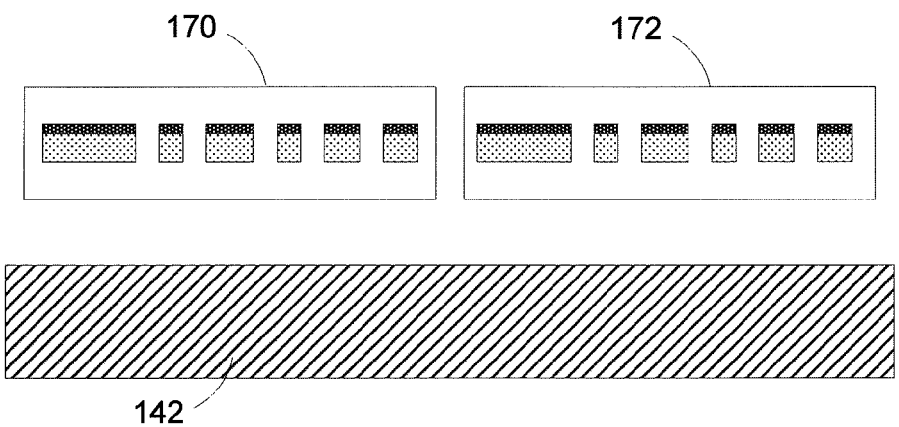
Figure 6M:
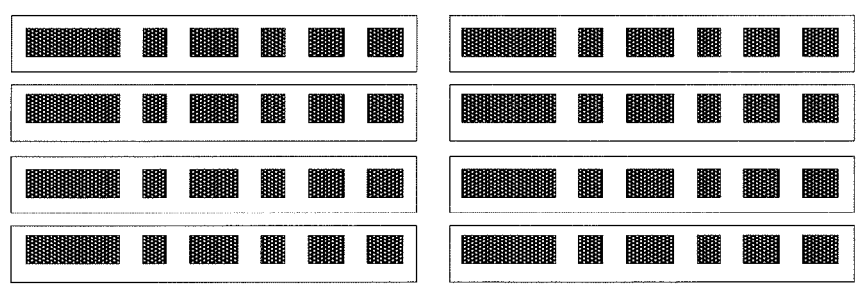

The microparticles are then separated from each other, while still attached to the underlying substrate, as shown in FIG. 6j. FIG. 6k schematically illustrates a top view of the microparticle in FIG. 6j, wherein each microparticle is separated from adjacent microparticles, but surrounded by the light transmissive layer (i.e. layer 168 in FIG. 6h). Finally, the separated microparticles are detached from the silicon substrate 142, as shown in a cross-sectional view in FIG. 6l. A top view of the detached microparticles from the silicon substrate is illustrated in FIG. 6m. The detaching of the microparticles from the underlying substrate (the "release" step) can be performed with any suitable etchant—preferably a gas or liquid matched to etch in all directions and undercut the microparticles. An additional sacrificial layer can be provided on the substrate in place of etching into the substrate itself. The etching can be wet, dry, or plasma etching; and the detaching layer is thus desired to be composed of a material etchable with the selected etching method. In particular, the etchant can be a spontaneous vapor phase chemical etchant such as an interhalogen (e.g. $BrF_3$ or $BrCl_3$), a noble gas halide (e.g. $XeF_2$), or an acidic vapor such as HF. A liquid could also be used to release the microparticles, such as TMAH, KOH (or other hydroxides such as NaOH, CeOH, RbOH, $NH_4OH$, etc.), EDP (ethylene diamine pyrocatechol), amine gallate, —HF etches glass so that won't work HNA (Hydrofluoric acid+Nitric acid+Acetic acid), or any other suitable silicon etchant (when the substrate or layer to be removed in the release is silicon (amorphous silicon or polysilicon or single crystal silicon—or tungsten, tungsten nitride, molybdenum, titanium or other material that can be removed in a silicon etchant such as $XeF_2$). If the material to be removed is not silicon, then the etchant is naturally matched to the sacrificial material (e.g. downstream oxygen plasma for a photoresist or polyimide sacrificial layer, etc.).

The indentations are as a result of the particular fabrication method; and can remain in the final product, or can be removed by, for example, planarization—e.g. chemical-mechanical-polishing (CMP) techniques. In fact, the indentations in some situations can be beneficial for code detection and/or fluorescence quantitation using fluorescent methods because the binding of a fluorescently tagged material to the surface of the microbarcode is greater in the indentation areas (per unit length of the microbarcode), the so called indentation signal enhancement, fluorescence can be greater in the indentation areas and can be used to determine the code (with or without other transmissive or reflective techniques discussed herein below). The same indentation signal enhancement would be applicable with reporter systems other than fluorescence, e.g. radioactive reporters, etc.

Though a silicon wafer was mentioned as the substrate in the example given above, a glass substrate, such as a glass wafer or larger glass sheet or panel (e.g. like those used in the flat panel display industry) could be used. Glass (or silicon) wafers can be of any suitable size—e.g. 4 in., 6 in., 8 in. or 12 in. When a glass wafer is used, typically an additional sacrificial layer will first be deposited (for later removal during the release step). The sacrificial layer can be semiconductor material, such as silicon, an early transition metal, such as titanium, chromium, tungsten, molybdenum, etc. or a polymer, such as photoresist, as mentioned earlier herein.

SEMs

A scanning-electron-microscopy (SEM) image of a segment (e.g. segment 102) in FIG. 1a is presented in FIG. 9c. As can be seen in the figure, the cross-section of the segment is substantially square. The top of the segment has a width of 1.0 micron; and the bottom width of the segment has a width of 1.2 microns. The height of the segment is approximately 1 micron. Of course larger or smaller dimensions are possible.

An SEM image of a multiplicity of microparticles fabricated with the exemplary fabrication method as discussed above is presented in FIG. 10a. The SEM image clearly illustrates the opaque segment 172 surrounded by transmissive material of the microparticle. Also, the indentations mentioned previously are clearly visible. The sample in the SEM image of FIG. 10a was prepared for characterization by cleaving a chip perpendicular to the long axis of the particles, followed by a timed silicon etch to provide higher contrast between the inner silicon and outer silicon dioxide, purely for imaging purposes.

Release

The microparticles of the invention can be fabricated at the wafer-level, and released either at the wafer level or die level. Specifically, a plurality of dies each comprising a set of microparticles can be formed on a wafer. The microparticles on each die may or may not be the same—that is the microparticles on each die may or may not have the same code. After forming the microparticles, the dies can be separated from the wafer; and the wafer(s) on the singulated dies can be then removed. An exemplary wafer-level fabrication method is demonstrated in FIG. 13a to FIG. 13C.

Referring to FIG. 13a, a plurality of dies is formed on wafer 236. In this particular example, multiple microparticles are formed on each die. The number, such as 3, 221, or 967 on each die represents the code incorporated in the microparticles in the die. The microparticles can be formed with a method as discussed above with reference to FIG. 6a to FIG. 6m. After formation of the microparticles but prior to release, the wafer can be partially cut, preferably to a depth about half the wafer thickness. The wafer is then cleaned, for example with solvents and/or a strong acid (sulfuric, hydrogen peroxide combination). The clean is an important step as it prepares a fresh glass surface for later functionalization and biomolecule attachment. The clean can also be performed after the wafer is separated into individual dies, or on the particles once they have been released.

After the formation of the microparticles, the wafer is then broken into dies as shown in FIG. 13b, where each die preferably, but not necessarily, contains a single code. The dies are then placed in separate vessels such as test tubes or the wells of a well plate for release, shown in FIG. 13c. The well plate can be a typical 96-well plate (or 24-well, 384-well, etc.), or any other suitable set of holding areas or containers. For example, dies containing the numerically represented codes: 3, 221, and 967, are placed in different tubes for release. By releasing, the microparticles are detached from the wafer; and the particles can fall into the solution in the releasing liquid when a wet etch is used. The microparticles over time settle to the bottom of the tube or well due to gravity (or the tubes can be centrifuged). In some applications, it may be desirable to release multiple dies comprising one or more codes into a single container.

FIG. 12a shows particles before release, and FIG. 12b shows the same particles (i.e. particles from the same die) after release. Both images are optical microscope images taken with a 100× air objective on a non-inverted inspection microscope. In FIG. 12b the particles are dried on a silicon chip.

The releasing step can be performed in many ways, such as dry etch, wet etch, and downstream plasma etch. In an exemplary bulk wet etch, shown schematically in FIG. 11a tetramethyl ammonium hydroxide (TMAH) is used as the etching agent. TMAH can be heated to a temperature approximately from 70-80° C. Other chemical etchants can also be used and may work equally well, such as interhalogen (e.g. $BrF_3$ and $ClF_3$) and noble gas halide (e.g. $XeF_2$), HF in spontaneous vapor phase etch, potassium hydroxide in a gas phase etch, KOH, and other suitable etchants. A screen having characteristic apertures (or filter membrane with pores) less than the smallest microparticle dimension can be placed on the top of each well or container, whether liquid or gas release is used, to keep the codes safely within each container and avoid contamination of microparticles into adjacent wells. During the etching, especially the gas phase etch or dry etch, a mesh can be attached to each tube, whether on one end of the tube, well or container, or multiple mesh covering on more than one side of a tube, well or container, such that gas etchant and etching products can flow freely through the mesh while the microparticles are stopped by the mesh. A mesh or other filter can help to drain the liquid release etchant as well, without releasing the microparticles. Another example of a release etch process is shown in FIG. 11b and involves the deposition or formation of a sacrificial layer, as has been previously described.

After pelleting the particles through centrifugation or lapse of time, the liquid (so called supernatant) is removed and the particles are washed several times in water or a solvent. "Washing" refers to the successive replacement of the supernatant with a new liquid, usually one involved in the next chemical processing step. After detaching the microparticles from the substrate (or wafer), the substrate can be removed from etchant—leaving the microparticles in tubes. The released microparticles can then be transferred to containers for use.

The microparticles can be fabricated on the wafer level, as shown in FIG. 13a to FIG. 13c. Referring to FIG. 13a, wafer 236, which is a substrate as discussed above with reference to step 122 in FIG. 2, comprises a plurality of dies, such as dies 1 and 3. In an example of the invention, the wafer has 10 or more, 24 or more, 30 or more, or 50 or more dies. Each die comprises a number of microparticles of the invention, wherein the number can be 10000 or more, 20000 or more, or 50000 or more. The microparticles in the same die are preferably the same (though not required); and the microparticles in different dies are preferably different (again, not required) so as to represent different codes. In the instance when different dies comprise microparticles of different codes, the dies are preferably assigned with unique identification numbers, as shown in the figure so as to distinguish the dies and codes in dies.

Detection

Figure 14:
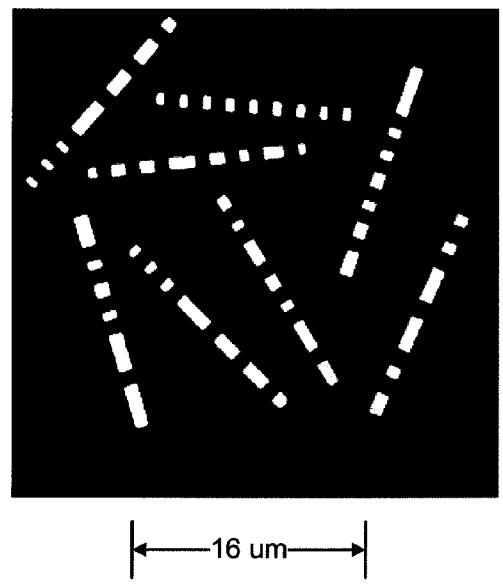
FIG. 14 presents a reflectance-mode inverted microscope image of 8 encoded microparticles of the present inventions.

FIG. 14 presents a reflectance-mode inverted microscope image of 8 encoded microparticles of the present inventions. All such black and white microscope images with a black background are taken on an inverted epi-fluorescence microscope with the released particles in the well of a well plate. The particles are dispensed into the well in a liquid and settle by gravity onto the bottom surface where they are imaged from below. Each particle in FIG. 14 has a different code. Segments of the less transparent material (e.g. opaque material in the visible spectrum), in this case amorphous silicon, reflect light and are the brighter regions in the image. The surrounding transparent material, in this case silicon dioxide, is not visible in the reflectance-mode images. The particles are 16 μm long by 2 μm wide and approximately square in cross section. The image is a combination of selections from 8 images, one for each code. The illumination light is at 436 nm, and the objective used is a 60× magnification oil immersion lens.

Figure 16:
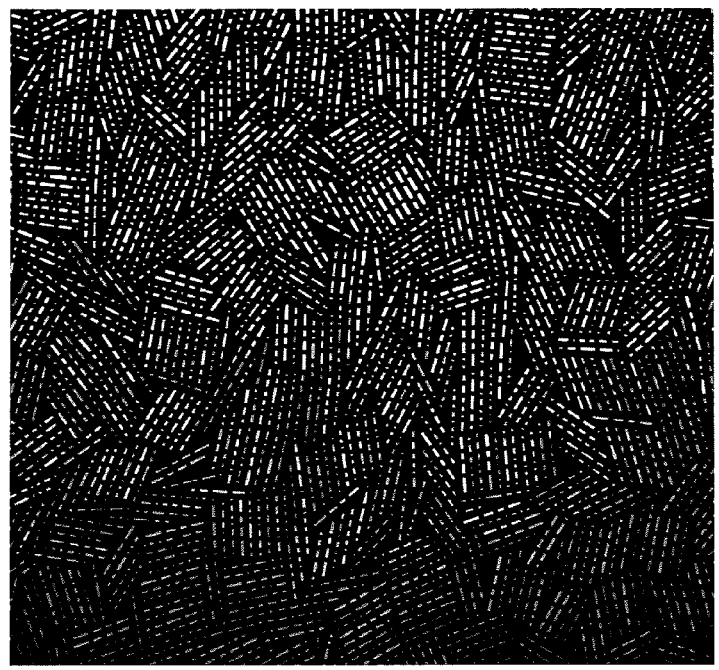
FIG. 16 presents a full field, single image taken at the same magnification as that in FIG. 14.

FIG. 16 presents a full field, single image taken at the same magnification as that in FIG. 14. The image is a mixture of many different codes. All particles form a high density monolayer—that is, there is no particle aggregation or clumping. The characteristic of the monolayer formation is one of the key advantages of the microparticles of the invention. When the microparticles are overlapped, aggregated, or clumped, the microparticles can not be properly identified. As a consequence, microparticles that do not readily form monolayers as herein, are forced to be used at relatively low densities (the total microparticles per unit area on the imaging surface). Low density imaging translates to correspondingly low throughput for the number of particles measured per unit time. This low throughput can be a limitation in many applications The tendency of the microparticles to form a monolayer is not trivial. Monolayer formation involves many factors, such as the surface charge state (or zeta potential) of the microparticles, the density of microparticles in a specific solution, the fluid in which microparticles are contained, and the surface onto which the microparticles are disposed. Accordingly, the microparticles of the invention are comprised of materials and are constructed in a form that favors the maintenance of a charged state sufficient to substantially overcome stiction forces; and thus microparticles are capable of undergoing Brownian motion which facilitates the formation of a reasonably dense monolayer of particles.

In biological applications, the microparticles are often used to carry biochemical probe molecules. For immobilizing such probe molecules, the microstructure preferably comprises a surface layer, such as a silicon dioxide layer, which can be chemically modified to attach to the probe molecules. In accordance with an example of the invention, the microparticles are constructed such that the microparticles are capable of forming a monolayer, for example, at the bottom of a well containing a liquid; and the monolayer comprises 500 or more particles per square millimeter, more preferably 1,000 or more, 2,000 or more, or 3,000 or more microparticles per square millimeter. In an alternative example, the microparticles can form a monolayer that such that the detectable particles occupy 30% or more, 50% or more, or 70% or more of the total image area (i.e. the image field of view). In connection with the example mechanism of self-assembled monolayer formation, it is preferred that the 2D diffusion coefficient of the microparticles of the invention is greater than $1 \times 10^{-12}$ cm$^2$/s. For accommodating the monolayer of the microparticles, the container for holding the microparticles in detection preferably has a substantially flat bottom portion.

Figure 15:
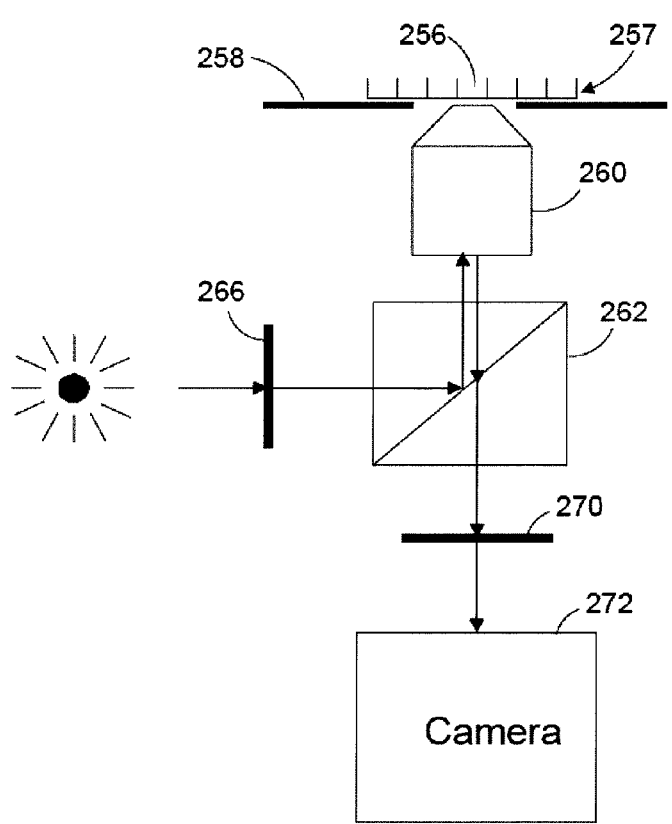
FIG. 15 shows a diagram of an optical system used to image the encoded microparticles of the invention.

FIG. 15 shows a diagram of an optical system used to image the encoded microparticles of the invention. The optical system 254 can be used to read the microparticle codes, including for bioassay applications. The system is an inverted epi-fluorescence microscope configuration. Other exemplary optical microscopy systems for the detection of the microparticles of the invention include but are not limited to confocal microscope systems, Total Internal Reflection Fluorescent (TIRF), etc. Well plate 257 contains many wells of which a single well 256 is imaged. The well plate sits on microscope stage 258. Microparticles that have been dispensed into well 256 in a liquid settle by gravity to the bottom surface. Light coming from light source 268 passes through excitation filter 266 which selects the illuminating wavelength. The illuminating light reflects off beam-splitter 262 and travels up through objective 260. Typically, only a fraction of well 256 bottom surface area is imaged. The imaged area is referred to as the "field" or "field area". Reflected or emitted light (know together as collection light) travels back down the objective and passes through the beam-splitter 262. Emission filter 270 selects for the collection wavelength. Finally the collected light is recorded with a detector 272, such as a CCD camera. This simplified version of the optical system is not meant to be complete. In practice, the actual microscope may have many more features, preferably including an automated stage and auto focus system for high throughput imaging. The excitation filter and emission filter can be mounted on computer controlled filter wheels and are automatically changed for the reflectance and fluorescence images. A computer controlled shutter controls the exposure times.

Figure 43:
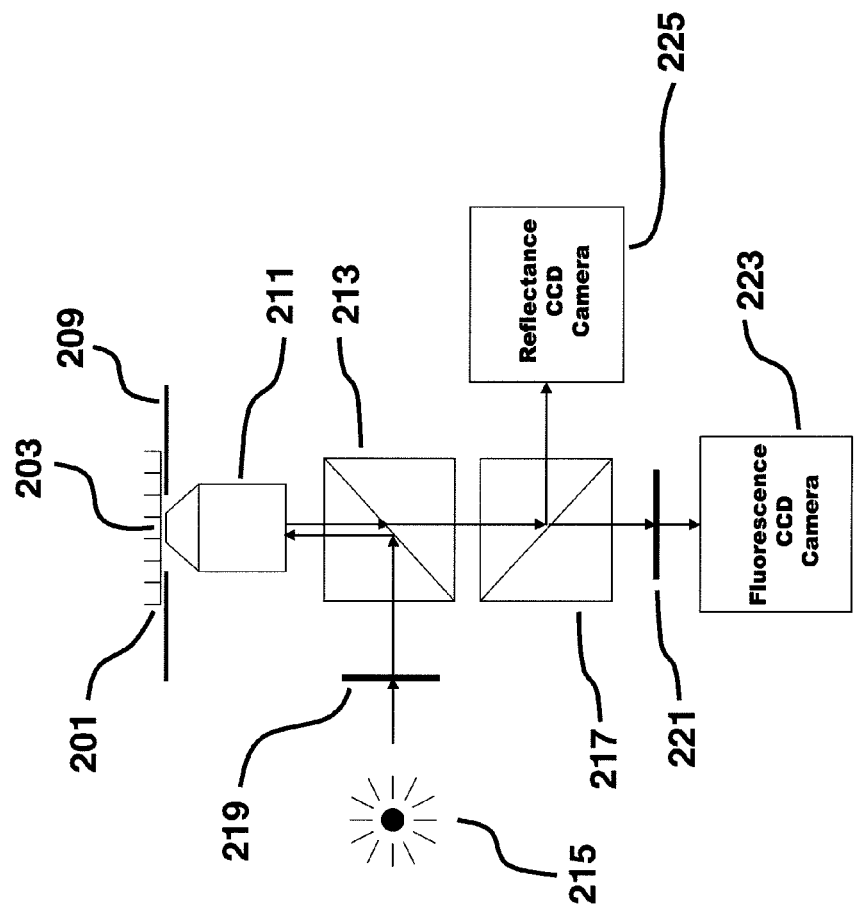
FIG. 43 shows a diagram of an optical system used to image encoded microparticles that utilizes two CCD cameras for the simultaneous acquisition of a reflectance and fluorescence image.

FIG. 43 shows a diagram of an optical system used to image encoded microparticles that utilizes two CCD cameras for the simultaneous acquisition of a reflectance and fluorescence image. The optical system is used for detection in bioassays. The system is an inverted epi-fluorescence microscope configuration. In the preferred embodiment, a wellplate 201 contains many wells of which a single well 203 is imaged. The wellplate 201 sits on the microscope stage 209. Particles that have been dispensed into the well 203 in a fluid settle by gravity to the bottom surface. Light coming from the light source 215 goes through the excitation filter 219 which selects the illuminating wavelength. The illuminating light reflects off the beam splitter 213 and travels up through the objective 211. Typically, only a fraction of the well 203 bottom surface area is imaged. The imaged area is referred to as the "field" or "field area". Reflected or emitted light (know together as the collection light) travels back down the objective and passes through the first beam splitter 213. The collection light then passes through the second beam splitter 217 which breaks it into the reflectance path and the fluorescence path. The emission filter 221 is located in the fluorescence path and selects for the appropriate fluorescence emission wavelength. The light in the fluorescence path is recorded with the fluorescence CCD camera 223. The light in the reflectance path is recorded with the reflectance CCD camera 225. This simplified version of the optical system is not meant to be complete. In practice, the actual microscope system may have more features, preferably including an automated stage and auto focus system for high throughput imaging. The excitation filter 219 and emission filter 221 may be mounted on computer controlled filter wheels to be automatically changed for multi-fluorophore experiments. A computer controlled shutter may be used to control the exposure times.

The system depicted in FIG. 43 is an improvement over the standard one camera system that utilizes filter wheels (or filter cube wheels) to acquire reflectance and fluorescence images in succession. The invention is accomplished by splitting the outgoing beam path into two components with a beam splitter. One component is the reflectance path, which is captured with one CCD camera. The other component is the fluorescence path, which is filtered for the appropriate wavelength and captured with a second matched CCD camera. The beam splitter can be designed such that more light is directed into the fluorescence path such that the exposure times on the two cameras are approximately equal. The two camera system invention offers the advantage of increased throughput. Additionally, the invention offers the advantage of eliminating the positional shifts between reflectance and fluorescence images pairs that may be present in those of the one camera system. This simplifies the computer software based processing of image pairs because the particles are in the same physical locations in both images of the image pair. In a further embodiment, the optical system is used for detection in bioassays.

Figure 17:
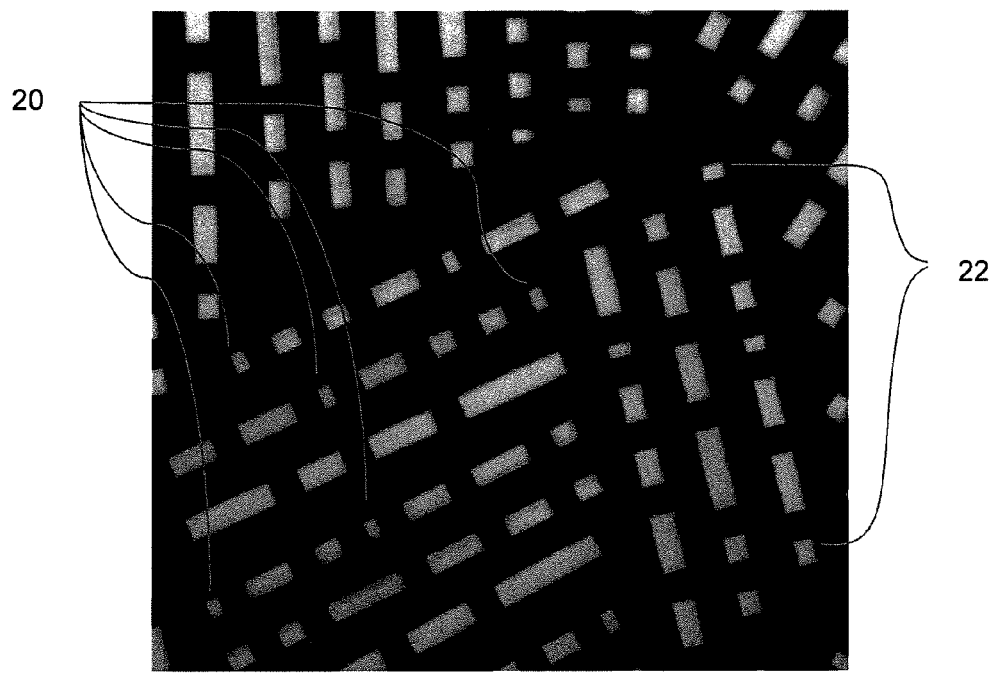
FIG. 17 shows a high magnification image of encoded microparticles.

FIG. 17 shows a high magnification image of encoded microparticles. The imaged particles consist of discrete segments of varying sizes. The smallest size segments 20 are 0.6 µm. End segments 22 form the end of a single particle. An exemplary example of the invention consists of encoded microparticles with spatial encoding features less than 1.5 µm in size.

Figure 18A:
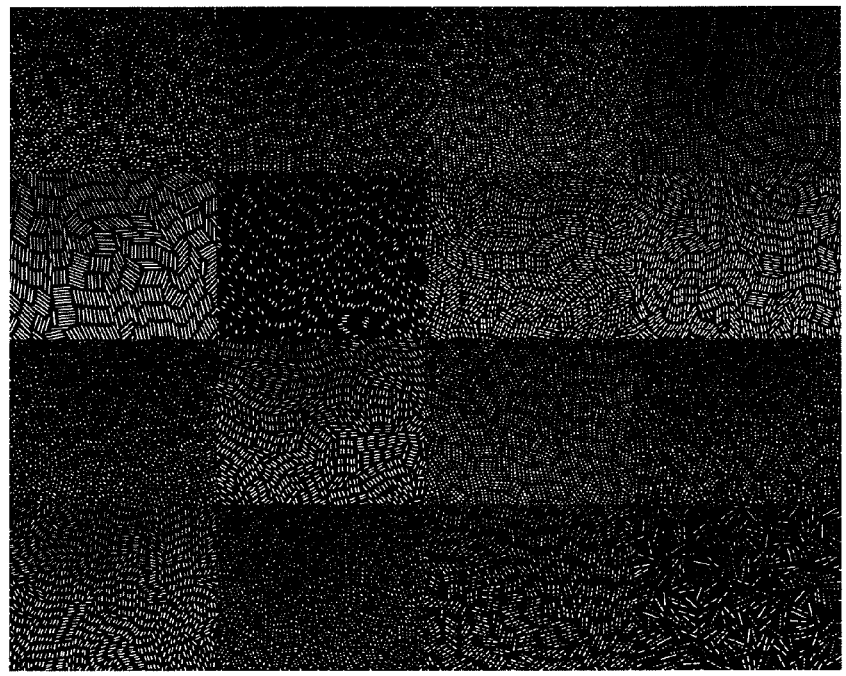
FIG. 18a shows a montage of 12 dense reflectance images of encoded microparticles.

FIG. 18a shows a montage of 12 dense reflectance images of encoded microparticles. Approximately 6,000 particles are in the images. The particles are a small fraction of the approximately 200,000 particles total in a well of a 384 well-plate. The total particles are approximately 10% of a set that contains 1035 codes (batches). The set was formed by combining approximately 2,000 particles from each of the 1035 batches where each batch contained approximately 2 million particles of a single code. These images are a subset of a larger image set from which data regarding identification accuracy is presented below.

Figure 18B:
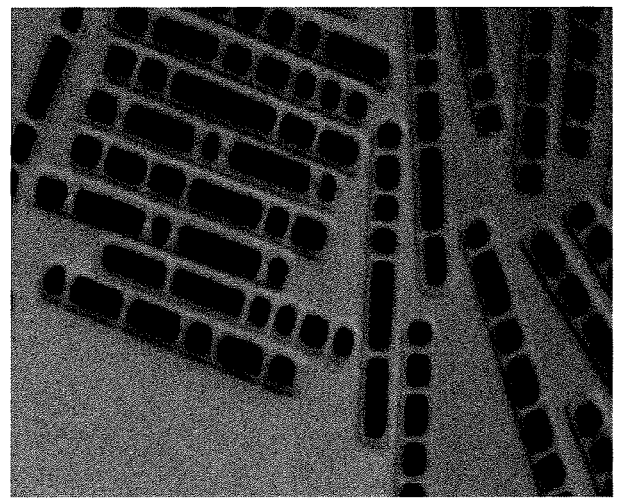
FIG. 18b shows a transmission fluorescence microscope image of example microparticles of the invention.

FIG. 18b shows a transmission fluorescence microscope image of example microparticles of the invention. Shown are here, in addition, small, elongated, encoded microparticles with an outer surface that is entirely glass. Shown are a multiplicity of non-spherical encoded particles with a silica (e.g. glass or silicon dioxide) outer surface and a length less than 70 µm (e.g. less than 50 µm.). The length of the example particles in this particular example is 15 µm.

In this image, the particles are in a solution that contains suspended fluorescent molecules. The fluorescent molecules, when excited by the microscope light source, provide illumination from above (i.e. behind with respect to the collection optics, see FIG. 15 for a diagram of the basic optical system) the particles. This image is similar to one that would be provided in transmission mode imaging configuration, and unlike the reflectance mode images of FIG. 16 to FIG. 18A, clearly shown the outer glass surface of the particles.

For successfully identifying the microparticles, e.g. reading the codes incorporated therein, the images of the microparticles may be processed. Such image processing can be performed with the aid of software programs. According to exemplary examples of software programs and algorithms, pairs of raw and processed image are presented in FIG. 19a and FIG. 19b and in FIGS. 20a and 20b.

Figures 19A, 19B:
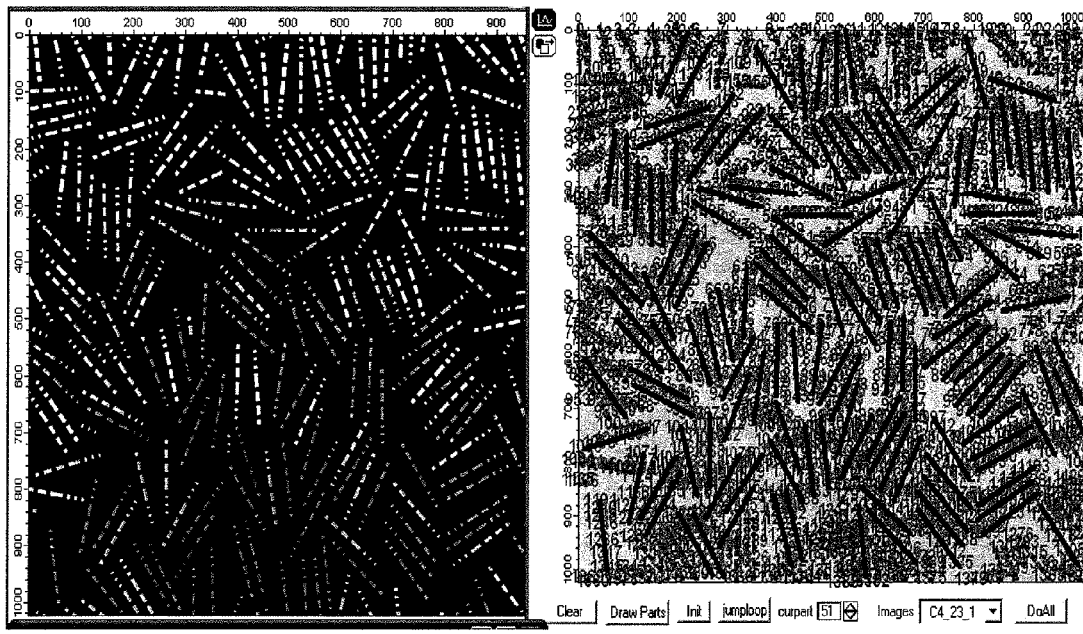
FIG. 19a shows a full field reflectance image.
FIG. 19b shows the same image selection of FIG. 19a after the image processing to associate discrete segments into full microparticles.

FIG. 19a shows a full field reflectance image; and FIG. 19b shows the same image selection of FIG. 19a after the image processing to associate discrete segments into full microparticles. The particles shown in the images are of a single code. Images of encoded microparticles of the present invention consist of discrete segments that appear white in the reflectance imaging. The gaps, which are between segments of individual microparticles consist of glass, are transparent, and therefore appear black in the reflectance image. The background of the images is also black. The segments are associated together into the particles by an algorithm. The algorithm finds the long axis of a long segment and searches along that axis for segments. Segments are accepted or rejected based on predefined parameters. The black lines in FIG. 19b correspond to particles for which segments have been associated together. In an exemplary example of the aforementioned algorithm, a computer program product that identifies the codes of encoded particles by associating discrete regions in an image into individual particles.

Figures 20A, 20B:
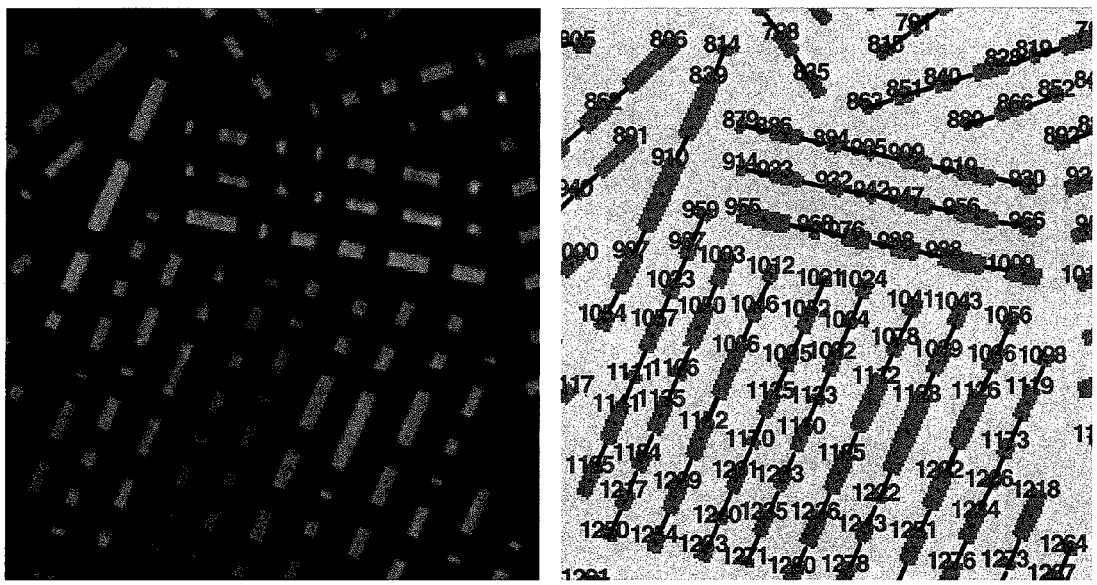
FIG. 20a shows a selection of a reflectance image.
FIG. 20b shows the same image selection of FIG. 20a after the image processing to associate discrete segments into full microparticles.

FIG. 20a shows a selection of a reflectance image; and FIG. 20b shows the same image selection of FIG. 20a after the image processing to associate discrete segments into full microparticles. The particles shown in the images are of a multiplicity of codes. The segments of the particles are numbered. The black lines in FIG. 20b are drawn to illustrate the segments that have been grouped together into particles by the image processing software.

Figure 21:
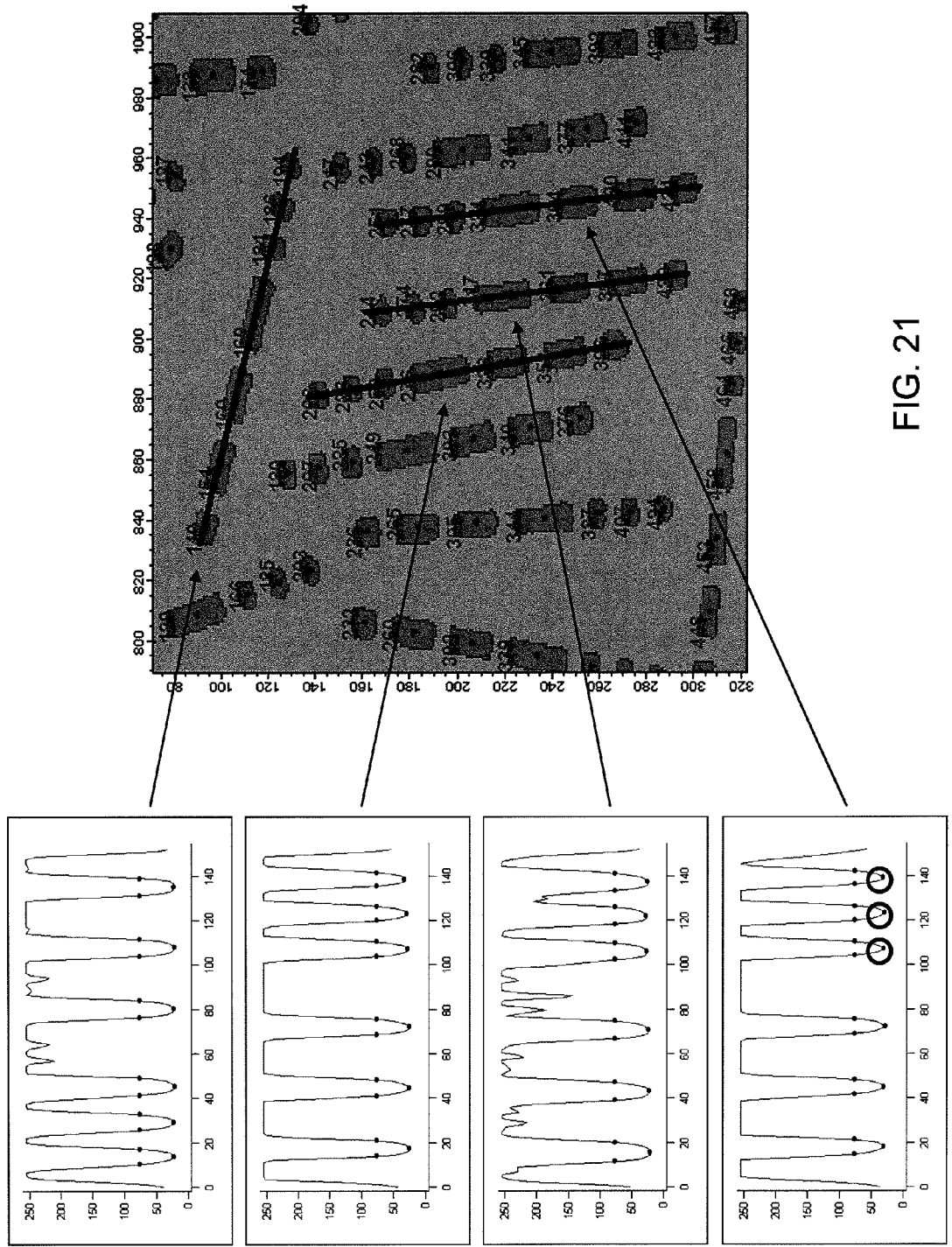
FIG. 21 illustrates a processed image is shown on the right and pixel intensity profiles from 4 example microparticles are shown on the left.

Referring to FIG. 21, a processed image is shown on the right and pixel intensity profiles from 4 example microparticles are shown on the left. The pixel intensity profiles are further processed by a computer software program to determine the codes of the microparticles. By identifying the center locations of the gaps, as indicated by circles in the pixel intensity profile in the lower left, the codes of the microparticles can be identified. As mentioned previously, the center gap locations are not sensitive to variations in both the particle fabrication process or image processing, i.e. variations in the dimensions of the actual segments, and gaps that make up the exemplary example structure of FIG. 1a. This feature is highly advantageous as it provides robust and accurate code identification of the encoded microparticles.

Table 3 shows identification data for image sets that include those images shown in FIG. 18a.

TABLE 3

| Images | Full ID % 30,069 Codes | Limited ID % 1,035 Codes |
| --- | --- | --- |
| 40x objective | | |
| ~500 particles/image 9866 particles measured | 99.5% | 99.98% |
| 60x objective | | |
| ~250 particles/image 2733 particles measured | 99.85% | 99.995% |

The microparticles included in Table 3 have a codespace of 30,069, wherein the codespace is defined as the total number of possible codes with the particular particle design, i.e. with the chosen coding scheme and coding scheme parameters. A pre-determined identification method assigns one of the 30,069 possible codes based on the analysis of the particle segment information. 1035 codes were randomly selected, manufactured, and mixed to form the collection. When analyzing the identification of the collection, if the software assigned code is one of the 1035, it is assumed to be correct. The number of "correctly" identified particles divided by the total is called the "ID %". This assumption underestimates the error rate (1-ID %) by the probability that a random error falls within the 1035 present codes, or 1035 divided by 30,069=about 3%. The assumption therefore ignores this 3% deviation and provides a close approximation to the true identification accuracy.

Figure 22:
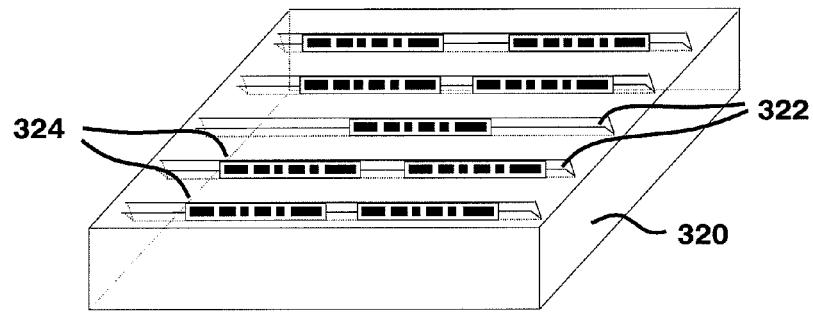
FIG. 22 shows a schematic of a specially prepared surface that have features designed to immobilize and separate the encoded microparticles for imaging.

FIG. 22 shows a schematic of a specially prepared surface that have features designed to immobilize and separate the encoded microparticles for imaging. The surface includes features, e.g. grooves and/or pits that trap the particles. Such surfaces could be useful in applications where the particles experience increased aggregation due to the nature of molecules coated on the surface or properties of the imaging medium. FIG. 22 shows an example of such a substrate 320 with grooves 322 designed to capture the particles. The substrate 320 is preferred to be glass, but may be other materials, for example other transparent materials. The grooves 322 shown in FIG. 22 have a V-shape but may take on any shape such as having a square or U-shaped bottom that accomplishes the task of capturing the particles. When particles are placed onto the surface, particles 324 fall into the grooves and are immobilized. In an exemplary example, encoded microparticles of the present invention, having an elongated and substantially square cross section, may be immobilized in grooves having a flat bottom.

Figure 23:
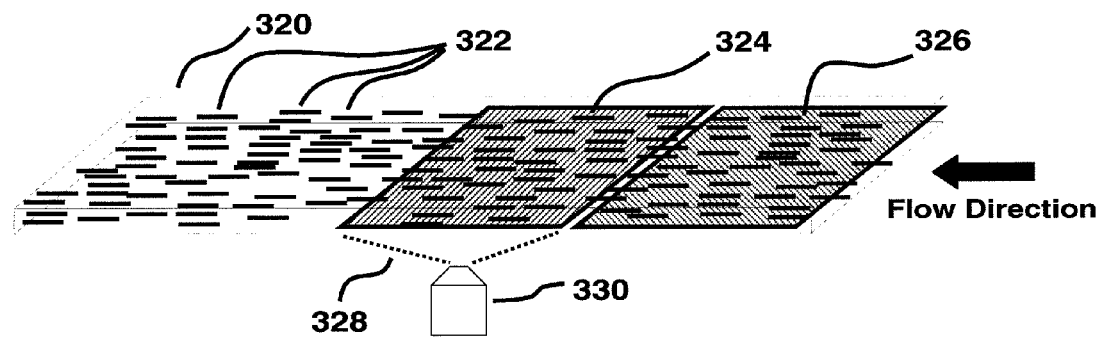
FIG. 23 and FIG. 24 show a flow-cell enabling the microparticles flowing in a fluid can be provided for detection by continuous imaging.
Figure 24:
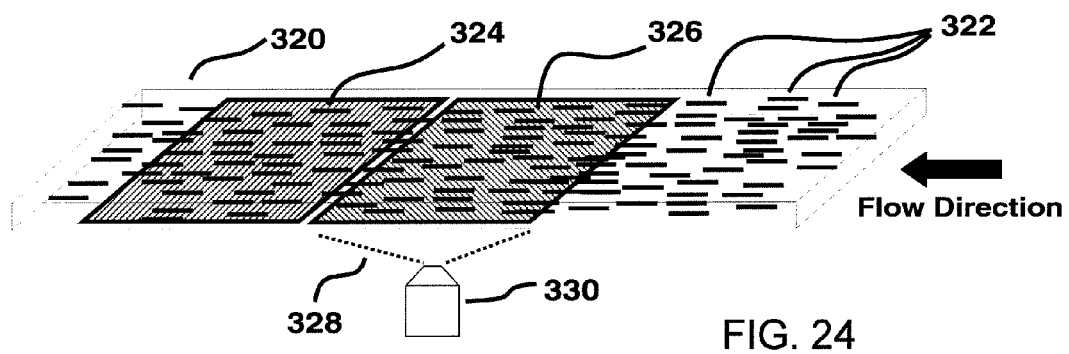

In an alternate example, a flow-cell enabling the microparticles flowing in a fluid can be provided for detection by continuous imaging, as shown in FIG. 23 and FIG. 24. Referring to FIG. 23, reflectance and fluorescence image pairs are acquired with the optical system depicted in FIG. 6 while the well plate is replaced with flowcell 320. Encoded microparticles 322 flow in a carrier fluid. Flow may be driven by pressure (hydrodynamic) or electrical means (electrophoretic or electro-osmotic). Further, microparticles may be aligned with electric or magnetic fields. The flow is from the left to the right as indicated by the arrow. The upper figure of FIG. 23 shows the flow cell at a given time and the lower figure of FIG. 23 shows the same flow cell at a subsequent time such that the particles have displaced a distance equal to approximately the length of the field of view. The optical system objective 330 is shown below the flow cell but may also be placed above the flow cell. In addition, the flow cell can be placed in other configurations with, for example, the flow being directed vertically. The objective 330 images the capture field area 328. The first field area 324 and the second field area 326 are shown as shaded regions. In the upper figure the first field area 324 overlaps with the capture field area 328 and therefore the first field area 324 is imaged. In the lower figure the second field area 326 overlaps with the capture field area 328 and therefore the second field area 326 is imaged. By appropriately matching the flow speed, flow cell size, and optical system, all particles passing through the flow cell can be imaged, thereby providing a system for high throughput detection. Another exemplary system for high throughput flow based detection of the encoded microparticles of the invention is a flow cytometer, the methods and applications thereof are well known in the art.

Other Structures

Figure 25:
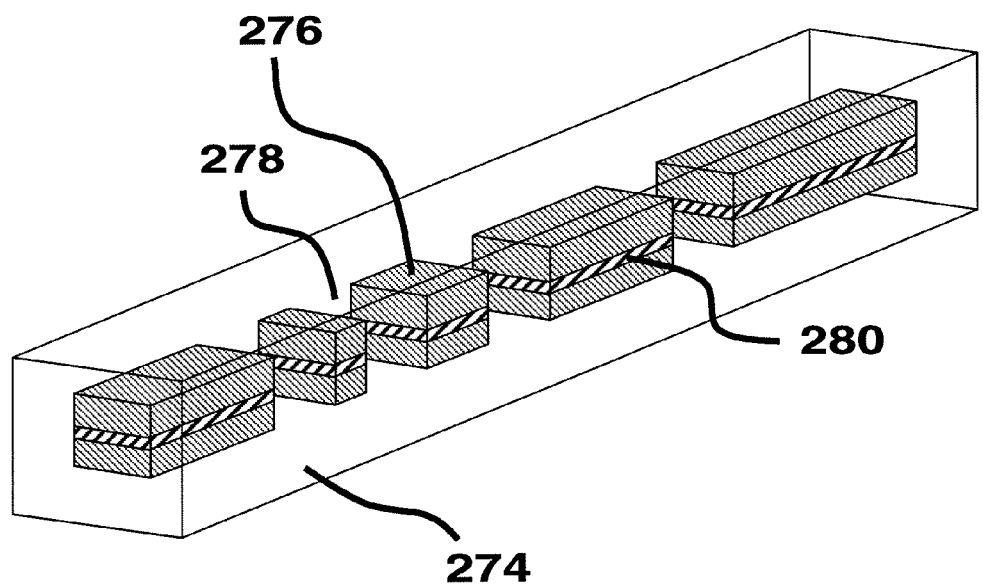
FIG. 25 illustrates another alternative microparticle of the invention.

Another alternative microparticle of the invention is schematically illustrated in FIG. 25. Referring to FIG. 25, microparticle 274 comprises opaque segments, such as 276, and gaps, such as 278, which are transmissive to the visible or near-visible light. The opaque material can be composed entirely or partially of a magnetic material such as (but not limited to) nickel, cobalt, or iron. The magnetic material could be incorporated as a thin layer 280 sandwiched between another material that forms the majority of the opaque material. The magnetic material gives the particles magnetic properties such that they can be manipulated by magnetic fields. This can aid in particle handling or facilitate the separation of biomolecules.

Figure 26:
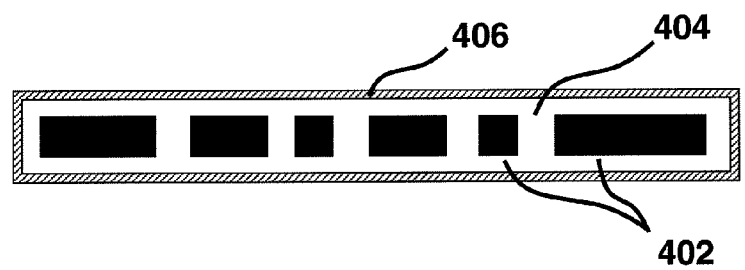
FIG. 26 shows a diagram of a spatially optically encoded microparticle with a fluorescent outer layer.

FIG. 26 shows a diagram of a spatially optically encoded microparticle with a fluorescent outer layer 406. This invention has utility in the tagging of material goods whereby the fluorescent layer improves the ability to easily find and identify the particles against diverse backgrounds. In an exemplary example, the fluorescent outer layer 406 is grown using a modified version of the Stöber process. The fluorescent outer layer 406 makes the entire particle fluorescent and facilitates the finding of the particles during detection. The reading of the particle code can be accomplished by imaging the particle in reflectance or fluorescence mode. One may be preferred over the other depending on the application, medium in which or surface to which the particles are applied. Particles of a single code can be used or mixtures of particles of different codes can be used. The particles can be applied in a medium such as a lacquer, varnish, or ink. The particles may be used to tag paper or fibers. The particles may be used to tag objects made of metal, wood, plastic, glass or any other material.

In another example, the fluorescent layer may be comprised of fluorophores, or other luminescent materials. The fluorescent layer may interact with molecular species in an assay, for example with fluorescently labeled nucleic acids or protein samples via Fluorescence Resonant Energy Transfer processes. In yet another example, the microparticles may have a non-fluorescent layer, wherein incorporated in or on the layer are molecules, for example quenchers that interact with luminescent emitter molecules.

FIGS. 27a to 27c show schematic diagrams of encoded microparticles of the present invention with surface indentations that form a spatial code. The microparticle may be fabricated by many methods including the aforementioned examples. FIG. 27a has surface indentations, aka divots, e.g. grooves, only on the face of the structure. FIG. 27b has divots on two faces. In other examples, divots and other desirable surface features may be placed on one or more surfaces of the microparticle structures, so as to provide a spatial code. FIG. 27c shows another example of such a structure, whereby the overall shape of the microparticle is substantially cylindrical. In an example method of making the microparticle of FIG. 27c, optical fibers having a diameter less than 1 mm may be laser or tip scribed to form the indentations. The composition of the structures of FIGS. 27a to 27c may be selected from a wide variety of materials, with glass being a preferred example.

In exemplary examples of encoded microparticles comprising indentations, the surface of the particles have fluorescent, or otherwise emitting, molecules attached to or in the surface, as shown in FIG. 27d. The emitting molecules may be covalently attached to the surface, adsorbed to the surface, or otherwise bound to the surface. In an exemplary example, the emitting molecules are incorporated into a layer which is deposited onto the microparticle. A uniform surface coverage of emitting molecules, e.g. a constant number of fluorophores per unit area, results in a nonuniform aerial density. Aerial density is defined as an intensity per unit length or per unit area that is integrated through a depth of field in an optical image plane. In this example, the aerial density is measured as an signal intensity profile measured by a detector, for example a CCD camera or photomultipler tube. FIGS. 28a to 28c show the nonuniform aerial density measured normal (i.e. perpendicular) to the particle surface for corresponding particles in FIGS. 27a to 27c. The signal intensity profile has peaks corresponding to the location of the surface indentions of the particles, which thus provide a detectable and useful code. The surface features of the encoded microparticles of FIGS. 27a to 27c may be detected by methods other than the use of emitting molecules, including but not limited to the measurement of light scattering, e.g. darkfield optical microscopy, etc.

Method for Producing Codes

The invented general method of generating the codes on microparticles consists of the use of multiple lithographic printing steps of a single code element per particle region. The multiple printing steps create multiple code elements per particle region. The code elements taken together form the code for the microparticle. In a preferred example, the printing steps are performed on many particles in parallel using a master pattern. A master pattern comprises an array of single code elements per particle region. A code element may represent more than one physical feature, such as holes, stripes, or gaps. The master pattern is printed multiple times such that a multiplicity of microparticles with complete codes is formed, wherein the multiplicity of microparticles comprises identical particles (e.g. all particles have the same code). Variations upon this theme, for example wherein the multiplicity of microparticles are not identical, are anticipated and will be described in detail below. Between multiple print steps, a component of the overall printing system changes to translate the code element within the particle region. In a most preferred example, this change is a movement of the substrate on which the particles are formed. In another preferred example, this change is the movement of the master pattern. In yet other examples this change is the movement of an optical element such as a mirror.

An exemplary example of the general method of generating code using multiple print steps involves photolithography as the printing mechanism, e.g. contact photolithography and projection photolithography. An exemplary example of projection photolithographic utilizes a step and repeat system (aka stepper). A reticle contains a code pattern that has a single code element per particle. Through multiple exposures of this code pattern at different lateral offsets, a multiplicity of code elements (per particle) is created. Combined, these code elements form a complete code. The lateral offsets define the code and are programmed into the stepper software. The offsets, and therefore the code, can be changed on a per die or per wafer basis. The codes printed on different dies on a wafer and/or different wafers in a lot are thus controlled by software and can be arbitrarily changed. This enables a powerful flexibility in the manufacture of large sets of codes. A single mask set, having one to a few masks, can be used to generate an arbitrary number of codes, numbering into the 105 range and beyond.

FIG. 29a to FIG. 29c shows an exemplary example of the invented method of producing the codes for microparticles. The microparticle regions 290 are areas that, upon completion of the fabrication process, will be discrete particles. FIG. 29a shows the status after the printing of the first code element 292 in each microparticle region 290, in this exemplary example the code elements are vertical stripes. FIG. 29b shows the status after the printing of a successive code element 294 in each microparticle region 290. FIG. 29c shows the status of the printing of three more code elements 296 in each microparticle region 290. The multiple printing steps thus provide codes on the microparticles.

FIG. 30a to FIG. 30c shows another example of the invented method of producing the codes for microparticles. The microparticle regions 300 are areas that, upon completion of the fabrication process, will be discrete particles. FIG. 30a shows the status after the printing of the first code element 302 in each microparticle region 300, in this exemplary example the code elements are circular. FIG. 30b shows the status after the printing of a successive code element 304 in each microparticle region. FIG. 30c shows the status of the printing of three more code elements 306 in each microparticle region 300. The multiple printing steps thus provide codes on the microparticles.

Figure 31A:
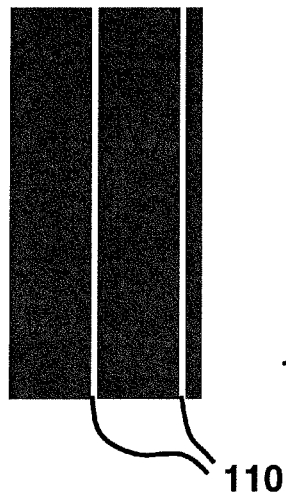
FIGS. 31a to 31c show drawings of the 3 mask fields of the preferred embodiment of the microparticle structure and FIG. 31d shows a drawing of a reticle plate.
Figure 31B:
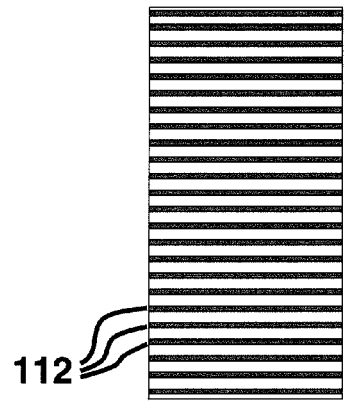
Figure 31C:
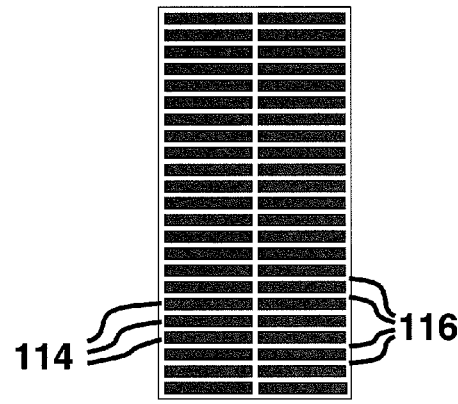
Figure 31D:
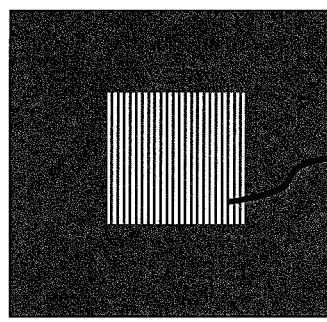

FIGS. 31a to 31c show drawings of the 3 mask fields of the preferred embodiment of the microparticle structure and FIG. 31d shows a drawing of a reticle plate. FIGS. 31a to 31c are small representative areas of the much larger full field (only 46 of approximately 2 million particles are shown). In these drawings, the regions that are gray have chrome on the actual reticle (so called "dark" in reticle terminology), and the regions that are white have no chrome (so called "clear"). Physically, the reticles are glass plates that usually measure 5" to 6.25" square and are about 0.09" thick. They are coated with a thin (a couple hundred nm) layer of chrome. The chrome is patterned with a resist through a serial lithography process, usually using a laser or ebeam system. The reticle is then wet etched which selectively removes the chrome. The final reticle then consists of a glass plate with chrome on one side in the desired pattern.

The code pattern, shown in FIG. 31a, has vertical stripes 110 that are clear. There is one vertical stripe per particle. FIG. 31b shows the bar pattern, which consists of horizontal stripes 112 that are dark (or equivalently wider horizontal stripes that are clear). The outline pattern, shown in FIG. 31c, consists of rectangles 114 that are dark. Clear streets 116 extend in the horizontal and vertical directions, separating the rectangles 114. The rectangles 116 will form the outer border of the particles. The horizontal stripes 112 define the width of the inner segments of opaque material. The vertical stripes 110 form the gaps in the segments. The gaps both form the code in the particle and separate two adjacent particles. FIG. 16d shows a full reticle plate. The reticle field 118 is the center region of the reticle which contains the pattern to be exposed. Alternate examples of the patterns described are also envisioned, including combining the code and bar pattern into a single pattern that can used according to the described multi print method.

An exemplary example of the invented method for producing codes uses photolithography and positive-tone photoresist. Positive-tone means that the areas exposed to light are developed away. For a negative-tone resist, exposed regions are what remain after development. The photocurable epoxy SU-8 is an example of a negative-tone resist. In an alternate example using a negative-tone resist such as SU-8, the regions that are to be segments are exposed to light instead of the regions that are to be gaps.

FIGS. 52a to 52c show flowcharts of examples of the code element patterning and etch steps. FIG. 52a shows the case where a hard mask is not used. This process is simpler but may produce segments with rounded corners because of the proximity effect of the photoresist exposures. At the corners of the segments, the photoresist gets some residual exposure from both the vertical stripes of the code pattern and the horizontal stripes of the bar pattern. The resulting rounding of the corners, though within the scope of the invention, is less desirable because it produces final particles that look different from the side vs. the top and bottom surfaces. The extent to which the rounding occurs depends on the specifics of the photolithography process including the pattern on the reticles, wavelength of the light source, and photoresist. FIG. 52b shows an exemplary example of the multi print method based patterning process and is described in detail in the below FIGS. 33a to 33m and FIGS. 34a to 34m. FIG. 52c shows another example of the particle fabrication process where instead of transferring the bar pattern to the hard mask, the bar pattern photoresist is used as the mask in conjunction with the hard mask oxide. This example method eliminates a few steps but may not be appropriate depending upon the specifics of the poly etch chemistry.

Figure 32:
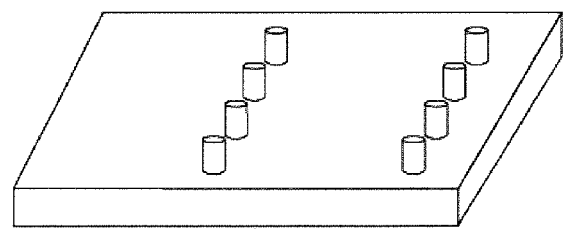
FIG. 32 shows an alternate example of the general method of generating code using multiple print steps utilizes stamping.

An alternate example of the general method of generating code using multiple print steps utilizes stamping (aka imprint lithography) as the printing mechanism, and is schematically depicted in FIG. 32. FIG. 32 schematically shows a small region of an example master pattern for stamp printing according to the invented multi-print-steps-to-build-the-code-up method, e.g. 1) stamping or pressing a stamper apparatus into the particle containing substrate, followed by 2) moving either the stamper apparatus or the substrate, and 3) stamping at least one more time in a nearby location, such that a complete code on the microparticles is formed. The substrate on which the microparticles can be formed using imprint lithography may be a wafer, such as a 100 mm, 150 mm, 200 mm, or 300 mm silicon wafer, or a panel, such as a 5" or larger glass or quartz panel, or rolled sheets (including but not limited to polymeric sheets).

Figure 33M:
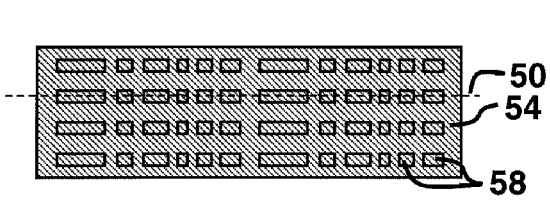
Figure 34M:
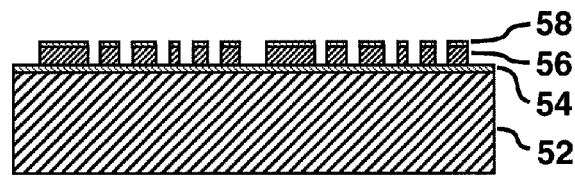

FIGS. 33a to 33m and 34a to 34m illustrate the microfabrication process steps of the example encoded microparticle of FIG. 1a. These steps define the inner opaque segments (which contain the code). The steps are shown in more detail than in FIG. 6a to FIG. 6m and include the photoresist exposure and development. FIG. 33a to FIG. 33m show top down drawings and FIG. 34a to FIG. 34m show the corresponding cross sectional views. The cross-section line 50 is shown in FIG. 33a to FIG. 33m. In FIG. 33a, the top surface is the hard mask oxide 58. In FIG. 34a, the film stack on the starting substrate 52 consists of the bottom oxide 54, poly 56, and hard mask oxide 58. In FIG. 33b the wafer has been coated with unexposed photoresist 120. The unexposed photoresist 120 is shown as the top layer in FIG. 34b. In FIGS. 33c and 34c, the unexposed photoresist 120 has been exposed with the code pattern a single time, forming exposed photoresist 122 regions. In FIGS. 33d and 34d, the code pattern has been exposed multiple times with lateral offsets applied between the exposures. In the preferred embodiment, the code pattern is exposed twice in directly adjacent regions to form double width stripes 124. Single width stripes 126 are the "gaps" that form the code. The double width stripes 124 are located in between the particles and separate the particles. To clarify, the lateral offsets are achieved by moving the stage on which the wafer sits. The lateral offsets are programmed into the stepper software. The lateral offsets define the code of the microparticles on that die. The lateral offsets (and thus code) can be different for every die on a wafer. Each wafer in a lot of wafers can have a different set of codes. In this way, very large code sets can be realized.

FIGS. 33e and 34e show the wafer after development of the photoresist. The exposed photoresist 122 from FIGS. 33d and 34d is removed revealing the underlying hard mask oxide 58. FIGS. 33f and 34f show the wafer after the oxide etch. The oxide etch removes the hard mask oxide 58 in the exposed regions revealing the underlying poly 56. FIGS. 33g and 34g show the wafer after the unexposed photoresist 120 of FIGS. 33f and 34f is removed. The hard mask oxide 58 is present in the regions that will become the segments. The poly 56 is exposed in the regions that will become the gaps in the opaque material. FIGS. 33h and 34h show the wafer after it is again coated with unexposed photoresist 120.

FIGS. 33i and 34i show the wafer after the exposure of the bar pattern. This is just a single exposure and is the same on all dies. This exposure is preferably aligned to the pattern already on the wafer. After exposure, the unexposed photoresist 120 pattern consists of horizontal stripes which define the segment width. The exposed photoresist 122 pattern consists of horizontal stripes which define the horizontal separations between the segments. FIGS. 33j and 34j show the wafer after the development of the photoresist. The exposed photoresist 122 from FIGS. 33i and 34i is removed revealing the underlying hard mask oxide 58 and poly 56. FIGS. 33k and 34k show the wafer after the oxide etch of the hard mask oxide. Only the poly 56 is present in the exposed photoresist region of FIG. 33i. FIGS. 33l and 34l show the wafer after the unexposed photoresist 120 is removed. At this point in the process, the top surface of the wafer is poly 56 with hard mask oxide 58 covering the poly 56 in the regions which are to become the segments of opaque material. Finally, FIGS. 33m and 34m show the wafer after the poly etch. The poly etch removes the poly 56 of FIGS. 33l and 34l, revealing the underlying bottom oxide 54. The hard mask oxide 58 is still present on the top surface of the poly 56 in the segment pattern.

In addition to the microparticle as illustrated in FIG. 1a, the methods above can be used to produce the codes for other encoded microparticle designs including currently known particle designs as well as other alternative designs. The method above can be used to produce the codes for the encoded microparticles, for example, in FIGS. 35a to 35c.

Figure 35A:
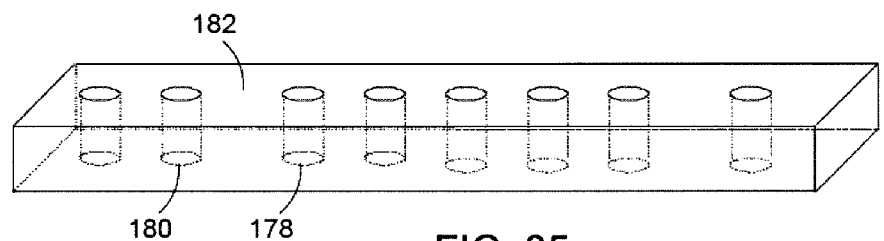
FIG. 35a to FIG. 35c show exemplary microparticles that can be produced using the method of the invention.

Referring to FIG. 35a, a bar-shaped microparticle with code elements consisting of holes such as holes 178 and 180 that are surrounded by frame material 182. The number and the arrangement of the holes forms a code derived from a predetermined coding scheme.

Figure 35B:
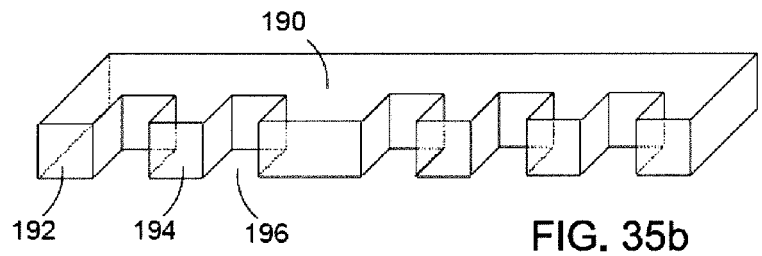

FIG. 35b shows another bar-shaped particle with the code elements comprising notches, such as notch 196. The adjacent notches define a set of protruding structures with different widths. The total number of protruding structures and the arrangement of the protruding structures with different widths represent a code derived from a coding scheme.

Figure 35C:
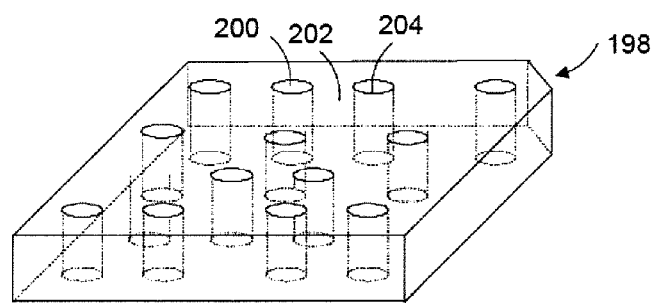

FIG. 35C shows a square plate shaped particle with the code elements consisting of holes, such as holes 200 and 202 that are separated by gap 202. The plate particle also includes an indentation 198 in one corner to break the symmetry of the particle and thus allow for more codes. Further shapes and code element architectures can also be made with the aforementioned method of producing codes.

Figure 36:
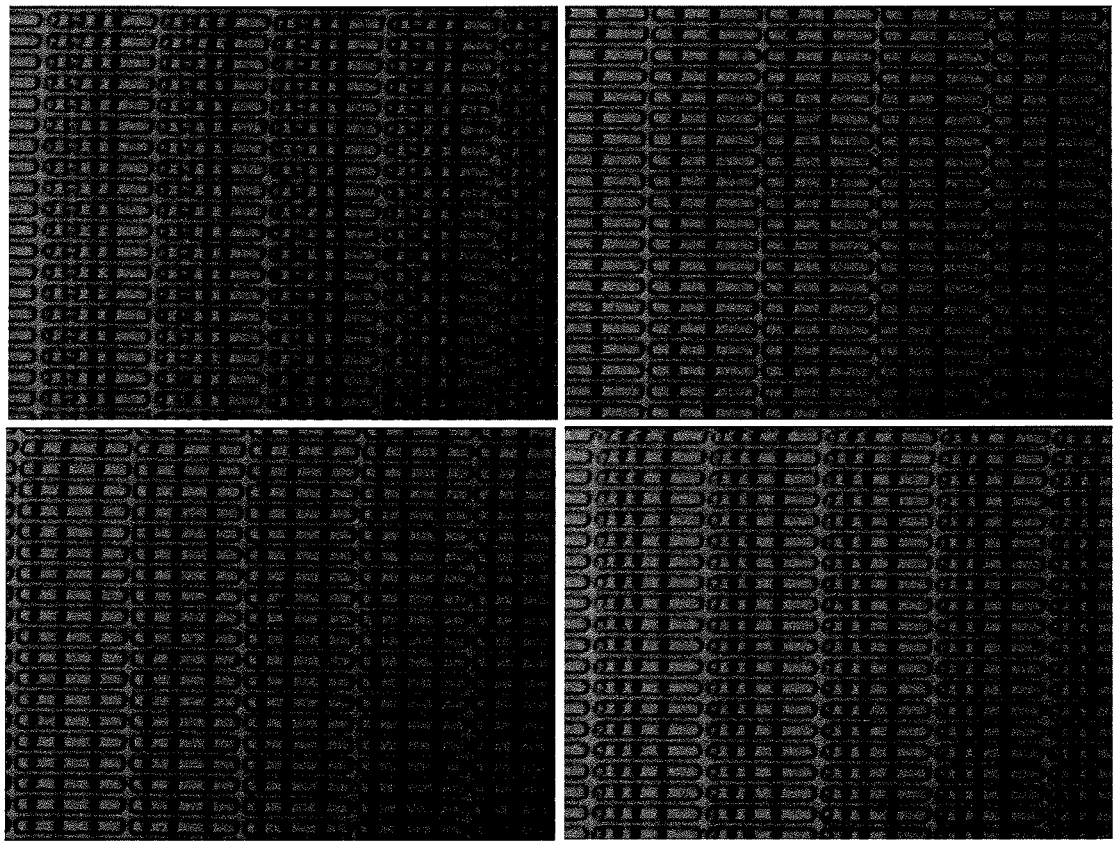
FIG. 36 shows four microscope images of actual encoded microparticles, just prior to release from the dies.

FIG. 36 shows four microscope images of actual encoded microparticles, just prior to release from the dies. These particles are produced according to the invented technique of producing codes with multiple print steps and according to designs described above.

Figure 37:
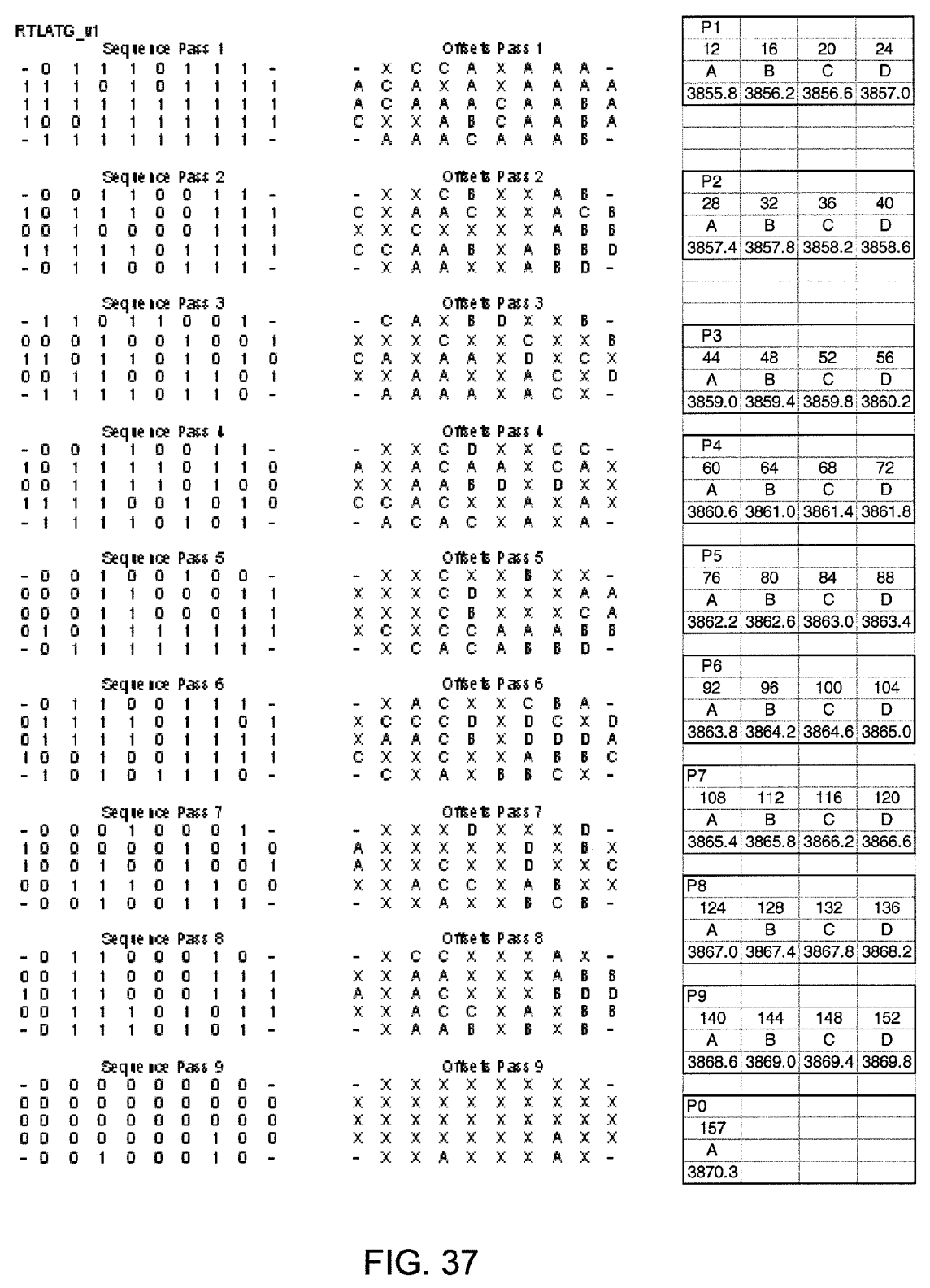

FIG. 37 shows charts of example data that is input into the stepper software to generate different codes on every die on a wafer. The charts show which dies get printed in 9 different passes and with what offsets. The data shown in FIG. 37 is an example of one system for organizing the multi print method using a stepper for providing a multiplicity of codes on a multiplicity of dies on a wafer. In this example, each die is exposed at most one time during a single pass. A wafer map of which dies are to receive exposures during the stepper exposure passes in this example is shown in the column on the left. "1" designates exposure. "0" designates no exposure. The middle column shows a wafer shot map of the exposure offsets, designated with offset letters "A", "B", "C", and "D". The right column shows a lookup chart of 1) the exposure location relative to the end of the particle, 2) the offset letter, and 3) the exposure locations programmed relative to a stepper reference point. The rows correspond to the different passes, 9 in this example.

Another example of a system for organizing the multi print method using a stepper is to exposure all of the code elements within a single die before moving on to the next die. Of course, a number of offsets other than four could be used. Though this and other examples of the general method of producing codes on microparticles has been described with respect to using a projection photolithography and a stepper, contact lithography and other patterning methods may also be used.

Figure 38:
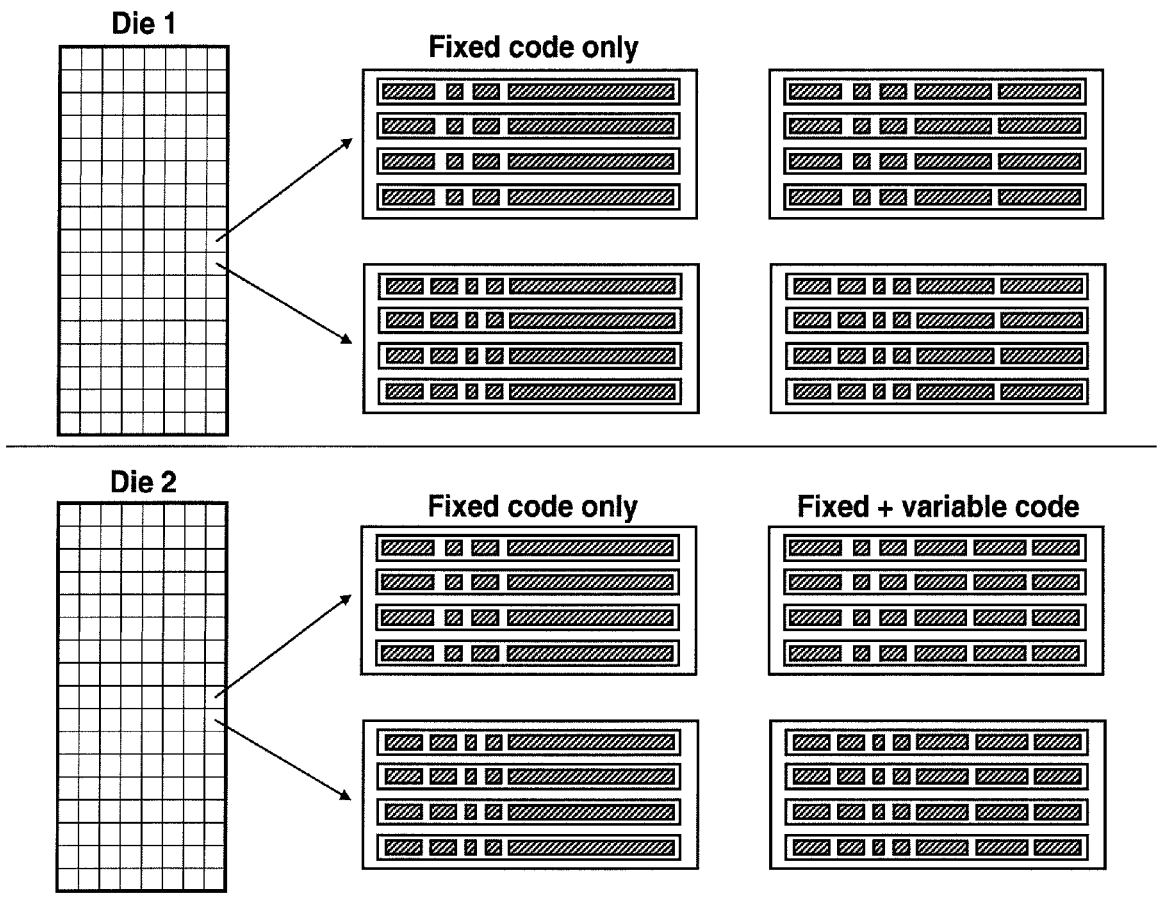
FIG. 38 shows drawings of an example scheme for producing an increased number of codes per die.

FIG. 38 shows drawings of an example scheme for producing an increased number of codes per die. In this scheme, within a die there are fixed and variable code element locations. Dies are divided into sub regions where each sub region has a different pattern of fixed code elements. For each die, a different pattern of variable code elements is exposed. The fixed and variable code elements together make up the entire code. A single wafer thus contains a total number of codes equal to the product of the number of dies per wafer and sub regions per die. An individual die, containing sub regions of different codes, could be physically separated into smaller sub-dies and the different codes released into different tubes. An alternative is to keep the dies intact and release the whole die into a single tube. This would create a mixture of codes from the different sub regions. This approach may be particularly useful for combinatorial synthesis applications.

The invented method of producing codes, for example the use of a photolithographic step and repeat system to form a complete code through multiple exposure steps of a single reticle field, may be used to apply unique codes to many types of components, e.g. MEMS and IC devices.

Coding Scheme

The microparticles as discussed above have incorporated therein codes derived from any desired coding scheme, such as binary or non-binary coding.

Figure 39A:
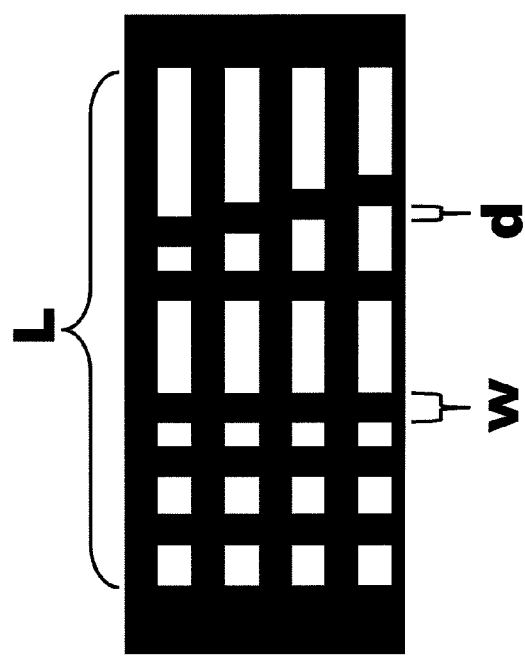
FIG. 39a shows a graphical representation of encoded microparticles that are formed according to the invented non-binary coding scheme.
Figure 39B:
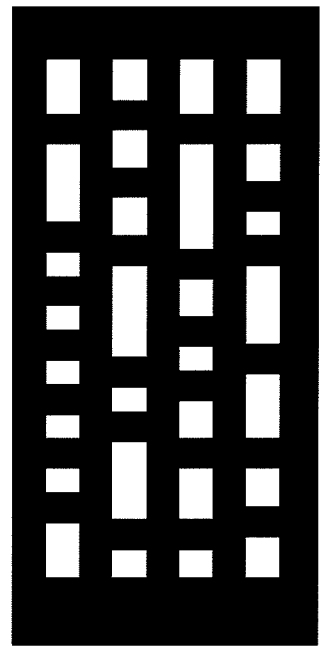
FIGS. 39b and 39c show random codes with different numbers of gaps and gaps of varying location.
Figure 39C:
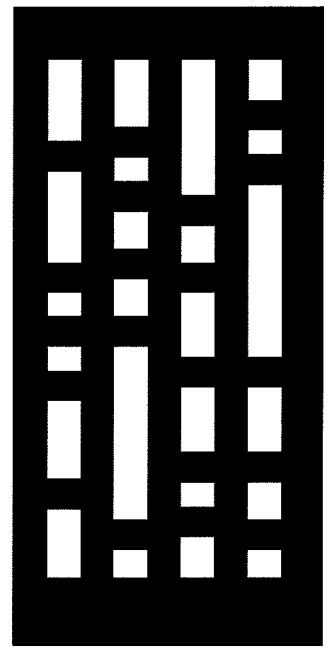

By way of example, FIG. 39a shows a graphical representation of encoded microparticles that are formed according to the invented non-binary coding scheme. Referring to FIG. 39a, the coding scheme parameters are L (the length of the particle), w (the width of the gap between segments), and d (the delta in the position of the gap center of the gap). FIG. 39a shows 4 particles with different codes such that only one of the gaps is varied in location. The gap is varied by amount equal to d, showing "adjacent" codes (e.g. codes that are similar and therefore more likely to be mis-identified for one another. FIGS. 39b and 39c show random codes with different numbers of gaps and gaps of varying location. Table 1 presents the total number of codes (codespace) for a variety of different parameter combinations. The number of codes is calculated from a computer software program that implements the invented non-binary coding scheme. Code degeneracy is taken into account in the algorithm (e.g. a pair of codes, such that when one is reversed, the codes are equivalent and the two codes are considered a single code). The parameters in Table 1 and Table 2 are specified in 100 nm units. The parameter combination L=152, w=8, d=4 which gives 30,069 is shown in FIGS. 39a to 39c. Table 2 presents the total number of codes that can be represented by the microparticles by different L. In an exemplary example, the discretization distance w is equal to or smaller than the characteristic segment size. As shown in Table 2, very large codespaces are available, and practically achievable with the aforementioned methods. The parameter combination L=152, w=5, d=4 has a codespace of approximately 2 million.

TABLE 1

| L | w | d | Number of Codes (Codespace) |
|---|---|---|---|
| 152 | 8 | 8 | 2134 |
| 152 | 8 | 7 | 3281 |
| 152 | 8 | 6 | 5846 |
| 152 | 8 | 5 | 11439 |
| 152 | 8 | 4 | 30069 |
| 152 | 8 | 3 | 105154 |
| 100 | 5 | 5 | 3,409 |
| 110 | 5 | 5 | 8,904 |
| 120 | 5 | 5 | 23,296 |
| 130 | 5 | 5 | 62,376 |
| 140 | 5 | 5 | 170,083 |

TABLE 2

| L | w | d | Number of Codes (Codespace) |
|---|---|---|---|
| 80 | 5 | 4 | 928 |
| 90 | 5 | 4 | 2,683 |
| 100 | 5 | 4 | 7,753 |
| 110 | 5 | 4 | 22,409 |
| 120 | 5 | 4 | 64,777 |
| 130 | 5 | 4 | 187,247 |
| 140 | 5 | 4 | 541,252 |
| 150 | 5 | 4 | 1,564,516 |
| 152 | 5 | 4 | 1,934,524 |
| 160 | 5 | 4 | 4,522,305 |

In an exemplary example, the coding scheme utilizes code elements placed at locations spanned by interval lengths smaller than the code element size itself. This deviates from the standard binary coding where the code consists of the absence or presence of a feature at discrete, evenly spaced locations. In the preferred embodiment of this coding scheme, naturally applicable to the above structure manufactured using the multiple print technique, the code element is the gap in the segmented inner opaque material. The gap size is chosen to be one that is reliably defined by the stepper and photolithography process and also resolvable by the microscope (working at the desired magnification). The gap size, interval length, and particle length determine the codespace (number of codes possible). The determination of a codespace involves tradeoffs between particle density on the wafer, identification accuracy, optical detection system complexity, and particle number per microscope image. Codespaces of over a million can be produced and accurately identified using practical parameter combinations.

In the example of a standard binary coding scheme, the particle would be divided into units of equal length. Each unit could then be black or white, 0 or 1. Because the particle is symmetric, there are two codes that are the same when one is reversed (so called "degenerate" codes). When counting the codes, one from each of the pair of degenerate codes is preferably discarded. Without the degeneracy, there would be $2^N$ possible codes, where N is the number of bits (units). With the degeneracy, there are about half that number. Exactly, the number of possible codes with the standard binary format is $[2^{N+2\mathit{floor}(N+1)/2}]/2$. In the example of the high contrast encoded microparticle structures of the present invention, previously shown in FIG. 14, FIG. 17, etc., within the full set of codes, there may be individual codes that have long runs of black or white regions. The black of the particles is indistinguishable from the black of the background, giving the particles extremely high contrast. However, codes having long runs of black are less desirable (though certainly within the scope of the invention) because it is more difficult to associate the white regions into the separate particles. For example, a more difficult code would be 1000 . . . 0001 (single white bits at both ends). It should be noted that, particularly for the structures and methods of making mentioned earlier herein, any suitable coding scheme can be used, as many other coding schemes are possible beyond that discussed in the example above.

The non binary coding scheme mentioned above has many advantages in the fabrication and detection of microparticles, including providing for high codespaces and robust code identification. In the example of the coding scheme, the reliability of the microparticle fabrication process is improved by permitting optimization of patterning and etch conditions for features, of a single size, e.g. gaps in the segments having a single width.

In the exemplary examples of encoded microparticles and methods of determining codes therein, e.g. as shown in FIG. 21, the code is determined by the center location of the gaps and not the lengths of segments. Therefore, if the dimensions change, either because of variation in the manufacture or variation in the imaging conditions or variation in the image processing algorithm used, the center position of the gaps does not change, rendering the code ID is robust. This scheme exploits the fact that in an optical imaging system the position of features, in this case the gaps, can be located to a resolution much smaller than the minimum resolvable dimension of the features themselves. For example, if the gap width may be 1.5 µm or less, and located to a distance smaller than 1.0 µm, more preferably smaller than 0.5 µm.

In general, a high codespace is desirable. In the field of genomics, having a codespace in the tens of thousands is especially important because it enables full genomes of complex organisms, such as the human genome, to be placed on a single particle set. The top portion of Table 1 shows the effect of varying the delta parameter, d, on the codespace. Shrinking d gives many more codes but places increased demand on the optical system. The need to resolve a smaller d means that a more expensive objective would typically be used. Practically, the lower limit of the gap interval distance is set by the resolution by the optical system (manifested as the pixel size of the digital image captured using a CCD camera). Using a 60× objective and 6.2 mm 1024×1024 CCD chip, an interval distance of d=0.4 µm equals approximately 4 pixels. If the interval distance is reduced to 0.3 µm (3 pixels), there are 105,154 codes. The codespace can be extended into the millions for longer particle lengths, L, and/or smaller gap widths, w.

The lower portion of Table 1 shows the effect of varying the length of the particle at fixed w and d. The length L is inversely proportional to the density of particles on the die (number of particles per unit area). The length also affects the number of particles in an image and thus throughput (particles detected per second). Tradeoffs exist between codespace, density, identification, and throughput. Optimization of the coding scheme parameters will determine the selected coding scheme for a particular application.

Large Particle Sets

Figure 40:
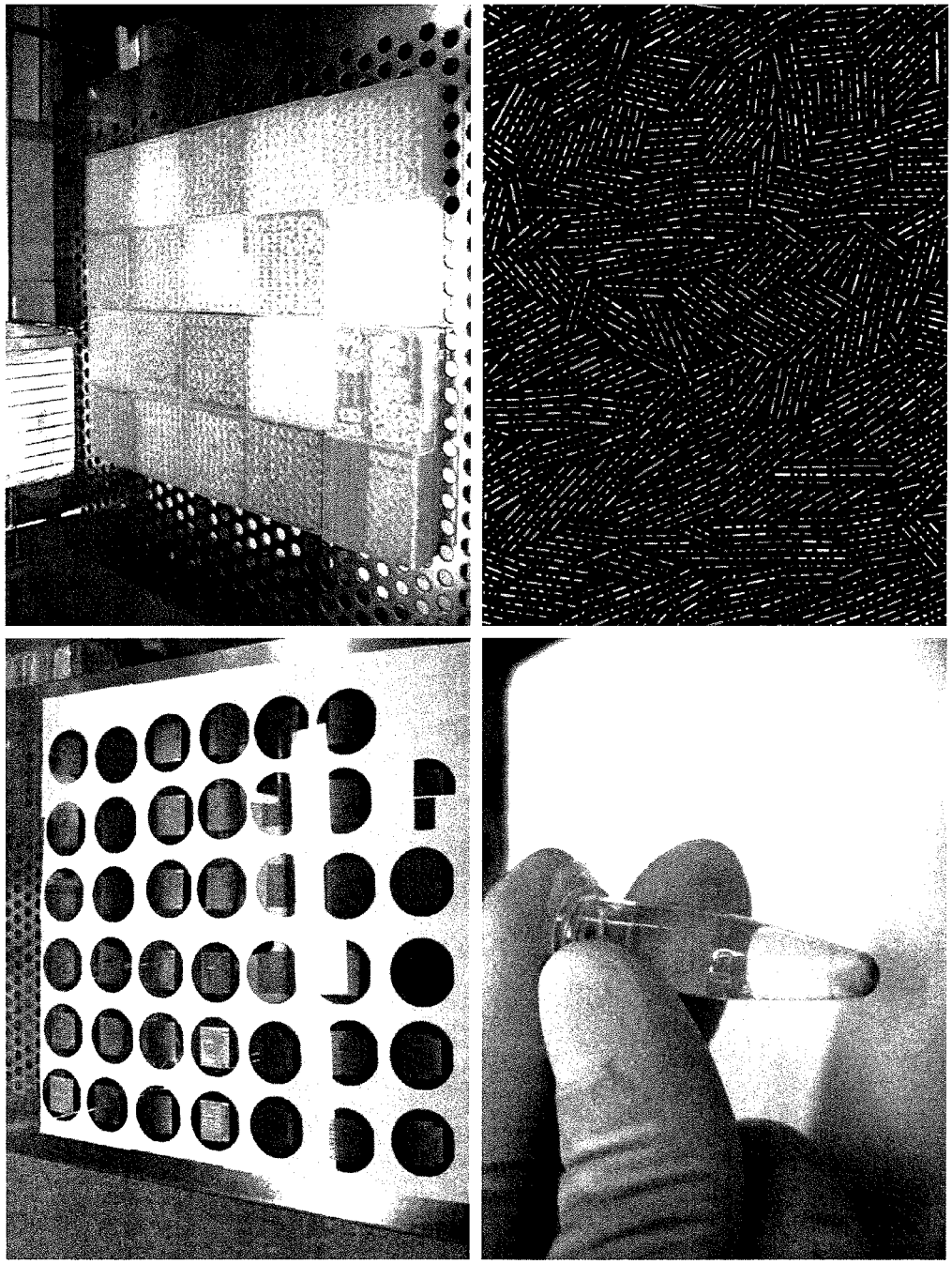
FIG. 40 shows photographs a montage of 4 photographs of various forms of a large prototype set of microparticles.

FIG. 40 shows photographs a montage of 4 photographs of various forms of a large prototype set of microparticles. The set contains over 1,000 codes and approximately 2 million particles of each code. The upper left photograph shows 40 wafers during the fabrication process. Each wafer has 32 dies with each die comprising approximately 2 million particles of a single code. As a further example, dies on a wafer may contain many more particles per wafer, e.g. 5 million or more.

Also, wafers (or other substrates, such as glass panels), may contain 100 or more dies, or alternately 200 or more, or 1000 or more dies. The wafer taken in whole may have 100 or more codes of encoded microparticle, or alternately 200 or more, or 1000 or more codes, or 5,000 or more codes. In an exemplary example of a large set of encoded microparticles, substantially all dies used to produce the large set, e.g. microparticles released from dies, comprise different codes. In another example, all dies on a wafer or substrate, may have the same code. The size of dies may be selected so as to optimize the balance between the number of particles per code and the number of codes in the large set of a large set. The number of particles per die and dies per wafer may be changed in software, for example by utilizing the invented method of producing codes, and optimized on a per manufacturing lot or per product basis for different applications, without necessitating the high capital costs of fixed tooling, e.g. large and expensive sets of photomasks.

In the upper right photograph of FIG. 40, the wafer fabrication has been completed and the particles released from the silicon substrate into test tubes. The test tubes are shown in the photograph in placed in containers that each hold 64 test tubes. The photograph in the lower left corner shows a single test tube which contains a small portion (approximately a few thousand particles) of each of 1035 test tubes of particles from the large set. The lower right image is a microscope image of a sample of the single test tube. This image shows members of 1035 codes mixed together.

Assays

The encoded microparticles, systems, and methods of the invention have a wide range of applications in the fields of biology, chemistry, and medicine, as well as in security and commercial fields involving the tagging of monetary bills, identification cards and passports, commercial products, and the like. In one example, the microparticles can be used in for molecular detection, such for as analyzing DNA, RNA, and proteins. In other examples, combinatorial chemistry or drug screening assays are performed as known in the art.

Figure 41:
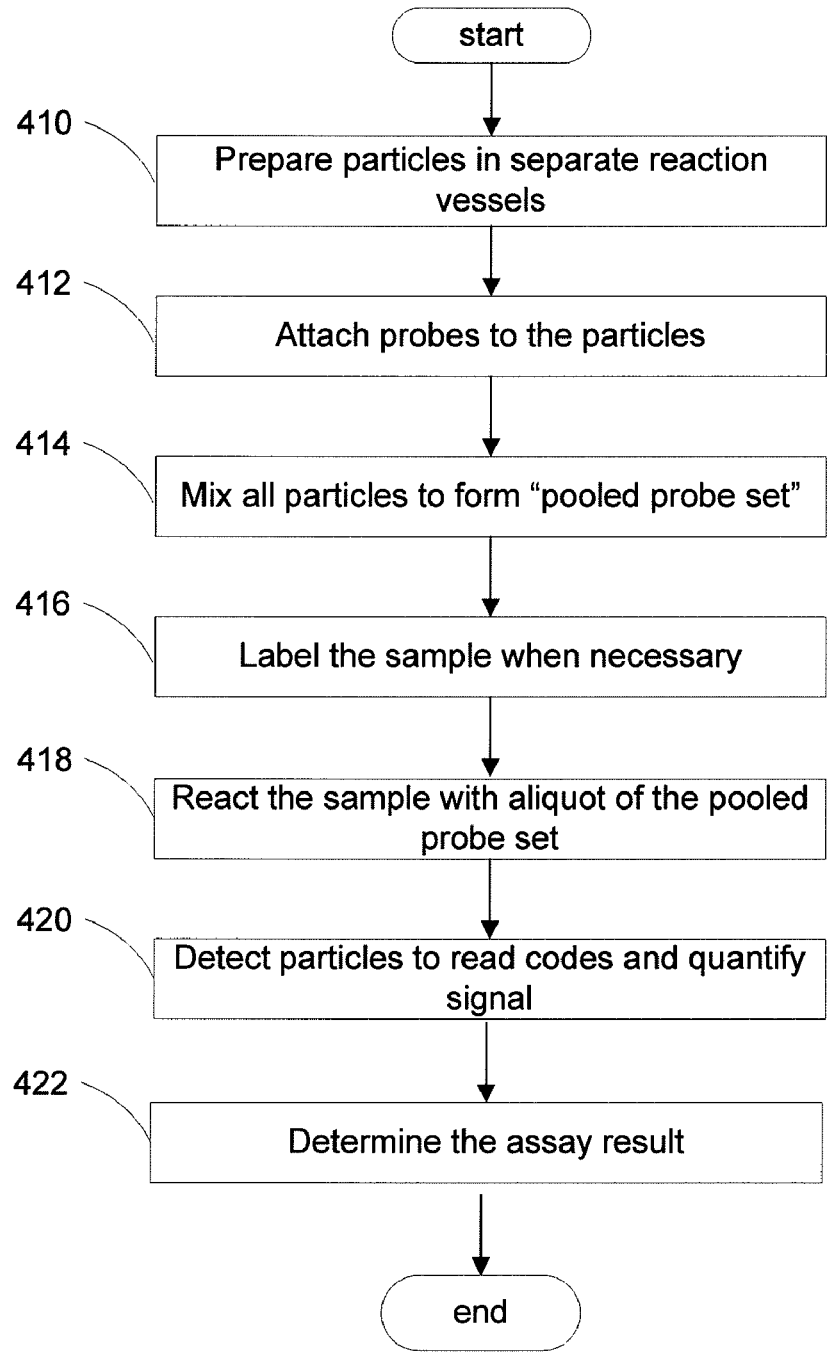
FIG. 41 is a flow chart of an exemplary bioassay process.

Referring to the flowchart shown in FIG. 41, microparticles are contained in separate tubes (or wells of well plates). Each tube contains a large number (e.g. a million or higher) of microparticles of a single code, at step 410. Biomolecules, such as DNA or RNA are immobilized on the surface of the particles and referred to as "probes" at step 412. Each species of probe is immobilized onto a different code and a lookup table is generated for future reference. Each species of probe also has one or more corresponding species of "targets" for which the binding between the two is specific. The probe/target terminology is usually used in reference to DNA and RNA complements but in this context refers to all biomolecules, including antibodies. Many probes are immobilized on a single particle, typically with a density on the order $10^4/\mu m^2$ or higher. The singular use of "a probe" often refers to a plurality of probe molecules; and "a code" often refers to a plurality of particles of a certain code, as with other terms used herein.

The mating of the encoded particles and biomolecules produces a "pooled probe set" through step 414. The pooled probe set is a mixture of encoded particles where each code has a particular probe attached to the particle surface. The pooled probe set can then be used to determine the amount of individual targets present in a mixture of targets. The mixture of targets is referred to as the sample and is typically derived from a biological specimen. The sample is then labeled, typically with a fluorophore at step 416. When the sample is mixed with the pooled probe set, the probes and targets find each other in solution and bind together. With nucleic acids, this reaction, step 418, is called hybridization and is very selective. After the reaction, the particles are imaged to read the codes and quantify the fluorescence at step 420. Referring to the code-probe lookup table, the amounts of the different target species in the mixed sample can now be measured and the assay result determined at step 422.

The samples reacted with the microparticles may be a purified biological extract or a non-purified sample, including but not limited to whole blood, serum, cell lysates, swabs, or tissue extracts. The samples reacted with the microparticles may be produced by culturing, cloning, dissection, or microdissection. Cells may serve as either the sample or probe in a bioassay utilizing the microparticles and other aforementioned inventions.

Figure 44:
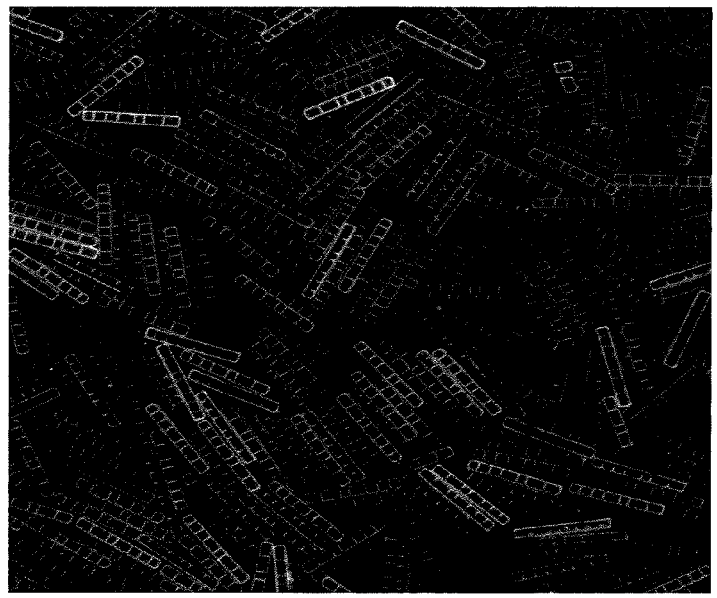
FIGS. 44 and 45 show dense fluorescence microscope image of a multiplicity of encoded microparticles.
Figure 45:
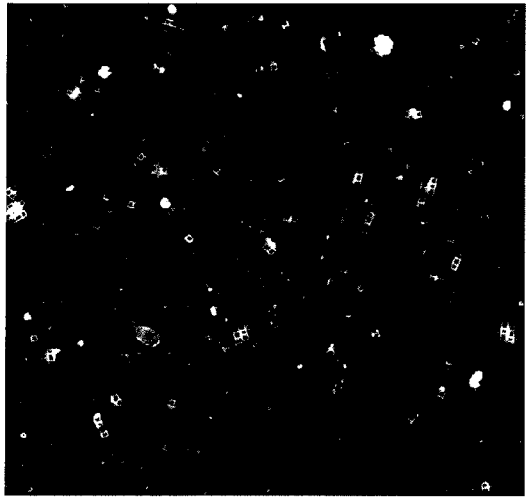

FIGS. 44 and 45 show dense fluorescence microscope image of a multiplicity of encoded microparticles. The microparticles shown in the images have oligo probe molecules attached to their surfaces and have been hybridized to prelabeled fluorescent oligo targets, where the base pair sequence of the targets is complementary to the sequence of the probes.

Figure 42:
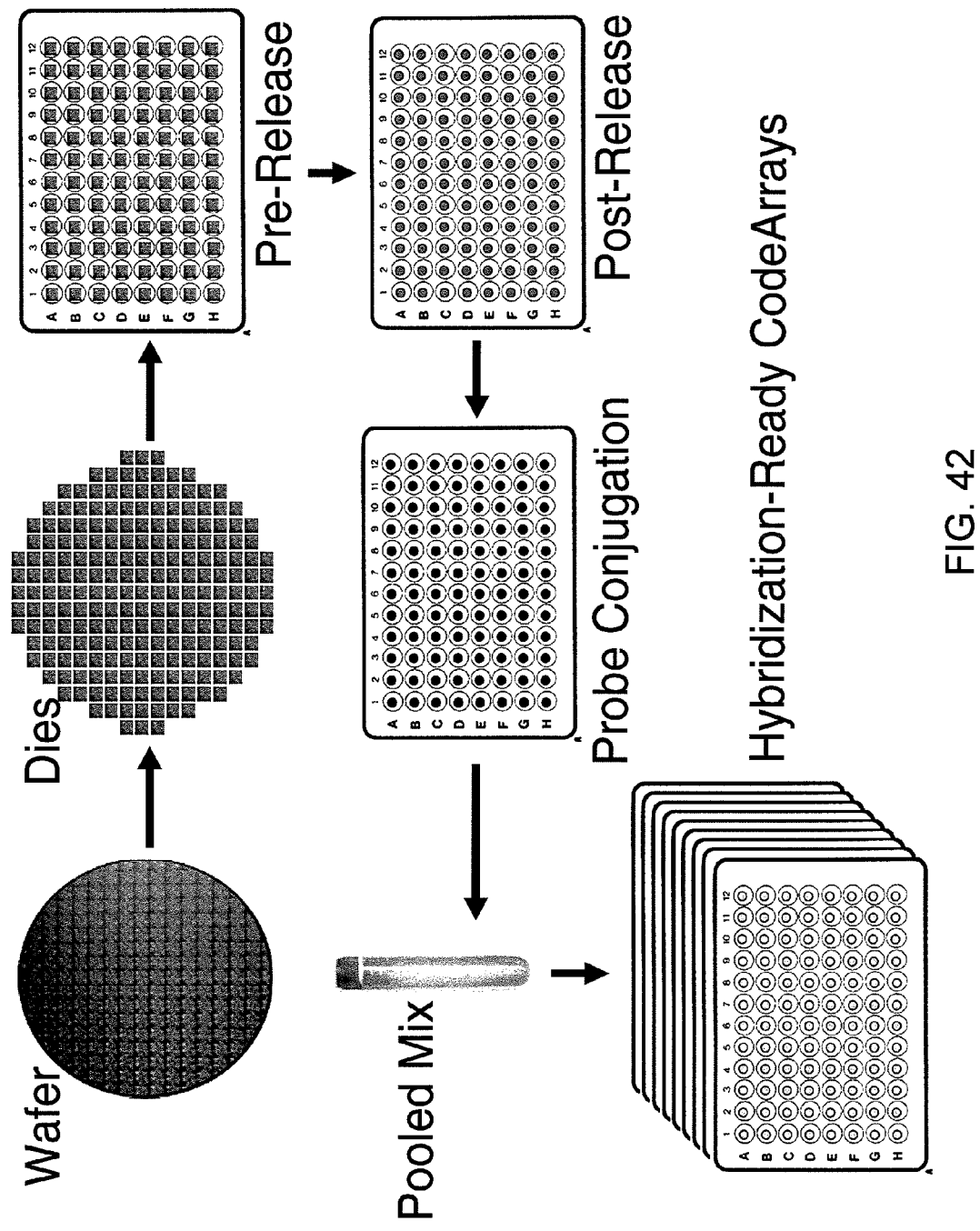
FIG. 42 shows a diagram of an exemplary example of the process by which whole wafers become mixtures of particle-probe conjugates that are ready to be reacted with samples to perform a bioassay.

FIG. 42 shows a diagram of an exemplary example of the process by which whole wafers become mixtures of particle-probe conjugates that are ready to be reacted with samples to perform a bioassay (so called "Hybridization-Ready Code-Arrays"). After completion of the wafer fabrication steps, the wafer has many dies where each die contains many particles of a single code. As has been previously described, alternative schemes may be used where dies are produced with the same code or dies are subdivided and contain multiple codes. The wafer is diced (usually by wafer saw) into the separate dies, then each die is placed into separate wells of a wellplate. Alternatively, test tubes can be used instead of wells. A release step is performed e.g. using a chemical etchant such as TMAH) that removes the particles from the surface of the die. The die is then removed from the well, leaving the free particles. After release, the conjugation of the biomolecule probes is performed resulting in each well containing a single type of particle probe conjugate (with particles of a single code and those particles having a single species of biomolecule on the surface). After conjugation, all of the particles are mixed together to form a "pooled master mix". The pooled master mix is divided into aliquots such that sufficient representation from all species of particle-probe conjugates is present. These aliquots are then ready to be reacted with a sample to perform a bioassay.

It is noted that multiple different samples may be identified in a single bioassay as discussed above. Before the detection and after the hybridization, the microparticles can be placed into wells of a well plate or other container for detection. In one detection example, the microparticles settle by gravity onto the bottom surface of the well plate. The microparticles in the well can be subjected to centrifugation, sonication, or other physical or chemical processes (multiple washing steps, etc.), to assist in preparing the particles for detection. In another example, the microparticles can be placed onto a glass slide or other specially prepared substrate for detection. In yet other examples, the particles are present in a flow stream during detection, or present in a suspended solution.

Term conjugation is used to refer to the process by which substantially each microparticle has one or more probe molecules attached to its surface. Methods of conjugation are well known in the art, for example in Bioconjugate Techniques, First Edition, Greg T. Hermanson, Academic Press, 1996: Part I (Review of the major chemical groups that can be used in modification or crosslinking reactions), Part II (A detailed overview of the major modification and conjugation chemicals in common use today), and Part III (Discussion on how to prepare unique conjugates and labeled molecules for use in applications).

The molecular probes attached to the surface of the particles typically have known attributes or properties. In an example, the molecular probes can be derived from biological specimens or samples and used in the screening, including but not limited to genetic sequencing, of large populations where typically, the derivatives from one member of the population is applied to a single code, typically a multiplicity of particles of a single code. Preferably, microparticles having the same code have attached substantially the same probe molecules; whereas microparticles having different codes likewise have different probe molecules.

One of the most powerful features of a multiplexed assay using solution arrays of encoded particles as the platform instead of planar microarrays is the flexibility to add functionality to the assay by simply adding new particles. With standard microarrays, once the arrays are printed or synthesized, the array typically cannot be changed. If the researcher wants to change the probes for genes on the array or add probes for new genes, typically entirely new arrays would then be produced. With pooled probe sets of particles, new probe and particle conjugates (probes for short) can easily be added to the existing pooled probe set. In practice the new probes could be different probes for an already represented gene, probes for alternative splicing variants of genes, or tiling probes for genes.

Figure 46C:
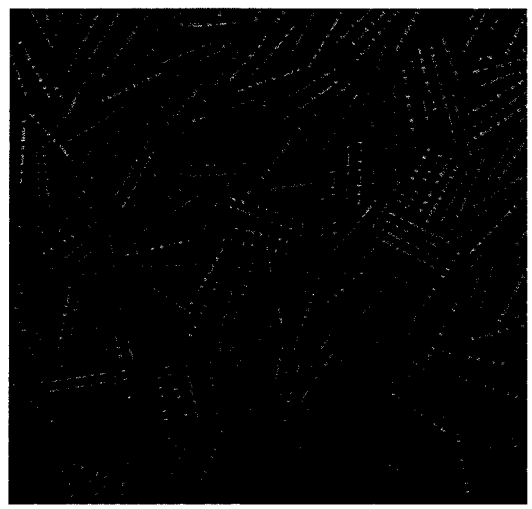
FIG. 46a and FIG. 46b show a reflectance and fluorescence image pair for the same set of microparticles of the invention, and 46c is an overlay of the images in FIG. 46a and FIG. 46b.
Figure 46A:
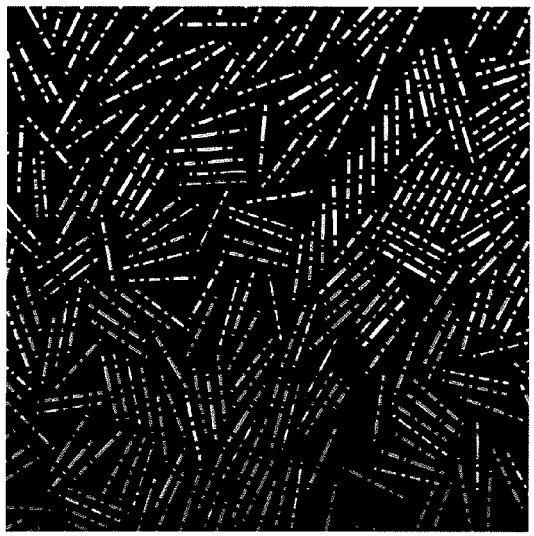
Figure 46B:
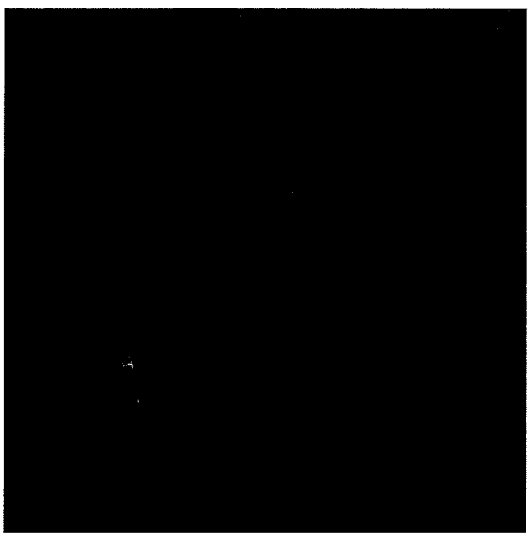
Figure 47A:
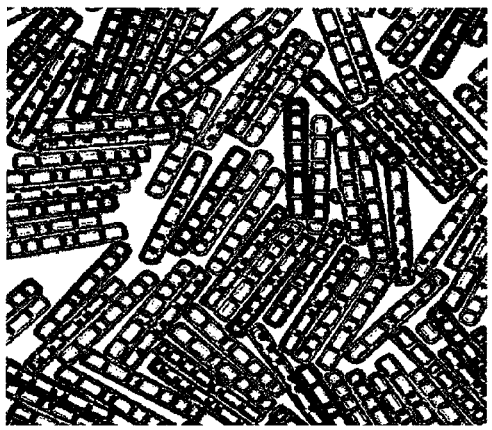
FIG. 47a to FIG. 47f show dense fluorescence microscope images of encoded microparticles in a time sequence.
Figure 47B:
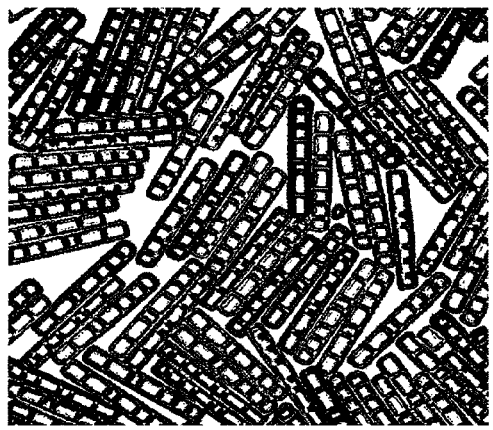
Figure 47C:
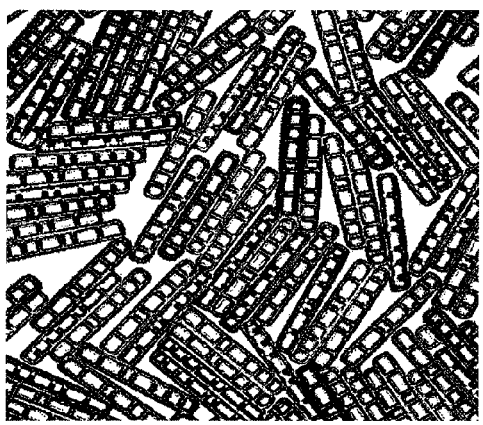
Figure 47D:
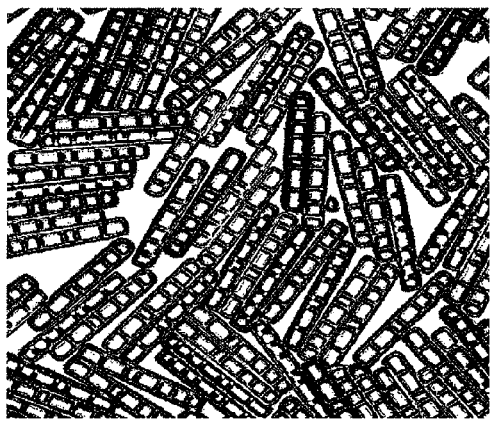
Figure 47E:
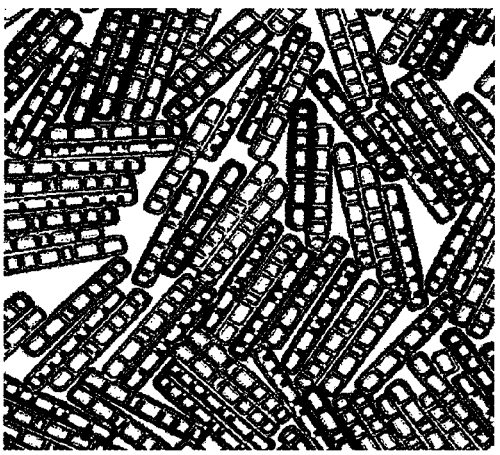
Figure 47F:
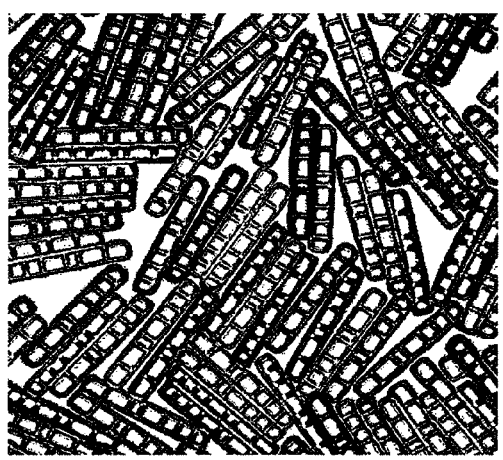

FIG. 46a and FIG. 46b show a reflectance and fluorescence image pair for the same set of microparticles of the invention. The images were taken in succession by about 1 second apart. FIG. 46a, the reflectance image was taken with blue light illumination and collection (excitation filter=436/10 nm, emission filter=457/50, i.e. overlapping filters). This image is used to determine the code of each particle. FIG. 46b, the fluorescence image, was taken with green illumination and red collection (excitation filter=555/28 nm, emission filter=617/73, i.e. filters for Cy3). FIG. 46c the image pair of FIG. 46a and FIG. 46b overlaid on top of one another in a single image.

FIG. 47a to FIG. 47f show dense fluorescence microscope images of encoded microparticles in a time sequence. The images have been processed for edge detection. The images were acquired approximately 1 second apart and are frames of the time sequence. The individual particles that comprise the images move a measurable amount between the frames due to molecular collisions (aka Brownian motion). This Brownian motion facilitates the assembly of the particles into a dense 2-dimensional monolayer. The particles shown in the images are examples of biochemically active encoded microparticles. The particles have oligonucleotide probes attached to the surface and have been hybridized (i.e. reacted in solution) with complementary oligonucleotide targets.

A Bioassay Process Using the Microparticle

The microparticles of the invention can be used as major functional members of biochemical (or chemical) analysis systems, including but not limited to solution based arrays, biochips, DNA microarrays, protein microarrays, lab-on-a-chip systems, lateral flow devices (immunochromatographic test strips). Applications include but are not limited to gDNA and protein sequencing, gene expression profiling, genotyping, polymorphism analysis, comparative genomic hybridization (CGH), chromatin immunoprecipitation (CHiP), methylation detection, as well as discovering disease mechanisms, studying gene function, investigating biological pathways, and a variety of other biochemical and biomolecular related applications such as inspection and analyses of proteins, peptides, polypeptide, and related biochemical applications. Assay architectures may include those well known in the art, including but not limited to direct DNA hybridization, hybridization of DNA to RNA or RNA to RNA, enzymatic assays such as polyemerase extension, ligation. The microparticles can also be used in microfluidic or lab-on-a-chip systems or any flow based systems, including but not limited to those systems wherein sample preparation, biochemical reaction, and bio-analyses are integrated.

For example, fluorescent tags can be employed when an optical imaging method based on the presence of fluorescence can be used. Radioactive labels can be used when the microparticles are utilized to expose or develop relevant photographic films. Alternatively, enzymatic tags can be used when the detection involves detection of the product of the enzyme tag that is released when the sample molecules bind to or react with the probe molecules on the microparticles. Other tagging methods are also possible, as set forth in "Quantitative monitoring of gene expression patterns with a complementary DNA microarray" by Schena et al. Science, 1995, 270-467, the subject matter of which is incorporated herein by reference in its entirety.

Samples without labels can also be reacted with the microparticles. For example, molecular beacon probes can be applied to the microparticle. Molecular beacon probes typically contains a hairpin structure that, upon binding the labelless, or in some examples labeled, sample molecules unfold, thus producing a signal indicative of the binding events. Such molecular beacon probes, as well as other probes, may be used in assays involving FRET (Fluorescence Resonant Energy Transfer), where for example fluorophores or quenchers are placed on or in the surface of the microparticles.

FIG. 48 shows real assay data from a 2-plex DNA hybridization assay. In this experiment, 2 different oligo probes (with 2 different sequences shown at the bottom) were attached to the surface of the different particle batches (with different codes). After probe attachment, the particles were mixed together and aliquots of the mixture were placed into two wells of a wellplate. Targets composed of oligos with sequences complementary to the probe sequences and fluorophore labels were then added to the two wells and reacted with the mixture of particle-probe conjugates. Target1, complementary to probe1, was added to the first well and target2, complementary to probe2, was added to the second well. Imaging of the particles of both wells was performed and the results are shown in FIG. 48. In the first well (with target1), particles of the corresponding code exhibit a relatively high fluorescence signal, and vice-versa for the second well.

For facilitating fast, reliable, and efficient bioassay for large number of sample molecules, it is preferred that the microparticles are capable of arranging themselves substantially in a monolayer on a surface, such as the bottom surface of the well in which the microparticles are contained. The microparticles are preferred to be able to undergo Brownian motion in the specific liquid in which the optical detection is performed. Given the specific liquid in which the microparticles are hybridized and detected, it is preferred that the 2D diffusion coefficient of the microparticles is equal to or greater than $1 \times 10^{-12}$ cm$^2$/s and/or 10% or more, such as 15% or more, or even 20% or more, and 50% or more of the microparticles are measured to undergo a lateral displacement of 20 nm or greater, such as 30 nm or greater, or even 50 nm or greater—in a time interval of 1 second or less, or preferably 3 seconds or less, or five seconds or less.

The detectable microparticles, which are referred to as those that are able to be accurately detected by the desired detection means, such as optical imaging using visible light, are capable of occupying 30% or more, 40% or more, and typically 50% or more of the surface area on which the microparticles are collected together, such as a portion of the bottom surface of the container in which the microparticles are contained. Defining an area in which at least 90% of all the microparticles are disposed (typically at least 95% or more typically at least 99%, and often 100%), the microparticles can be seen to have a density of 1000 particles/mm$^2$ or more, such as 1500 particles/mm$^2$ or more, 2000 particles/mm$^2$ or more, and typically 3000 particles/mm$^2$ or more (e.g. 5000 particles/mm$^2$ or more). The detection rate within the above-mentioned area, which rate is defined as the ratio of the total number of detected microparticles (microparticles with spatial codes detected) of a collection of microparticles under detection to the total number of the collection of microparticles, is preferably 80% or more, typically 90% or more, or more typically 99% or more.

Another preferred example of the invention is a kit comprising biochemically active encoded microparticles that contains 200 or more, more preferably 500 or more, 1000 or more, or even 10,000 or more different codes within the kit (due to the large codespace enabled by the invention, even larger numbers of codes.) Due to statistical sample requirements of convenient liquid pipetting and a desired redundancy of particular codes within the kit, more than 10 particles of the same code are typically provided (20 or more, or even 30 or more microparticles of the same code) within the kit, as in some example applications the redundancy improves the overall assay performance. The term "biochemically active encoded microparticles" is refers to microparticles that have biological or chemical moieties on surfaces and thus can be used in assays; and the term "moieties" are referred to as molecular species; including but are not limited to nucleic acids, synthetic nucleic acids, oligonucleotides, single stranded nucleic acids, double stranded nucleic acids, proteins, polypeptides, antibodies, antigens, enzymes, receptors, ligands, and drug molecules, cells, and complex biologically derived samples.

Figure 49A:
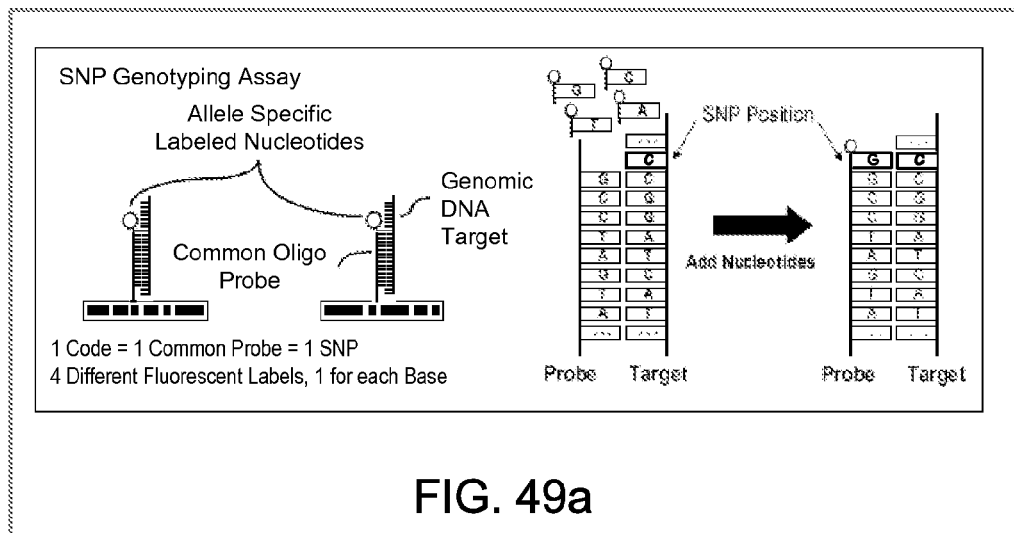
FIG. 49a illustrates an exemplary assay in which the microparticles of the invention can be used.
Figure 49B:
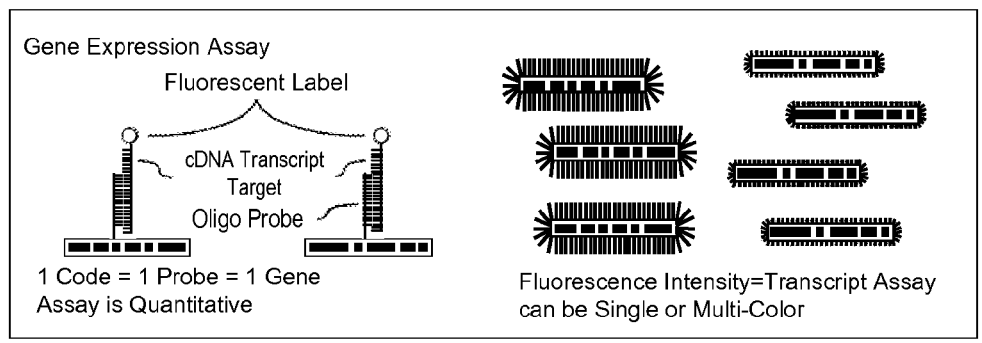
FIG. 49b illustrates another exemplary assay in which the microparticles of the invention can be used.

Universal adapter schemes may be used to provide a set of non-interacting synthetic sequences that are complementary to sequences provided on the probes. Genotyping can be performed using common probes and allele specific reporters or allele specific probes and common reporters. Amplification assays such as those involving PCR, padlock probes, or Molecular Inversion Probes can be performed using the particles of the current invention. Examples of two of these assays are shown in FIG. 49*a* and FIG. 49*b*. In an alternative example of the invention, biomolecules that are present on the surface of the particles can be pre-synthesized and then attached to the particle surface. Alternatively, biomolecules can be in situ synthesized on the particles.

Figure 50:
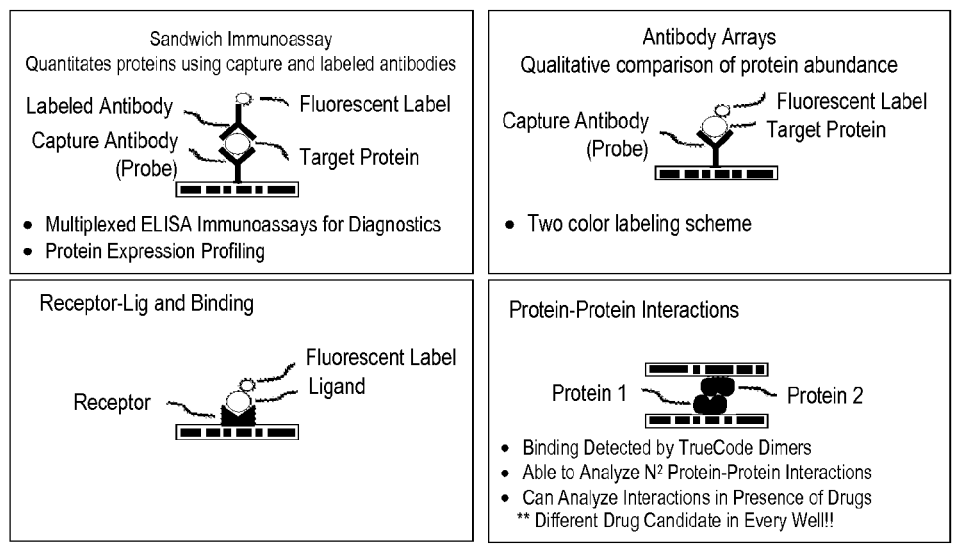
FIG. 50 illustrates another exemplary assay in which the microparticles of the invention can be used.

Protein based assays are also applicable. These include but are not limited to sandwich immunoassays, antibody-protein binding assays, receptor-ligand binding assays, or protein-protein interaction assays. Examples of these assays are shown in FIG. 50. The sets of encoded microparticles of the present invention can be used in solution based assays to investigate protein-protein interactions. This is shown in the bottom right of FIG. 50.

A single type of protein can be applied to microparticles of a single code. Upon mixing of the particle-protein conjugates and reaction in a particular biochemical environment, proteins that interact and bind to one another are determined by the presence of adjacent particles during detection. The square cross section of the microparticle structures of the present invention provide an improvement over the prior art by providing an increased area of contact in the shape of a flat, rectangular surface. Prior art particles that are spherical or cylindrical in shape limit the contact areas to single points or lines respectively. This invention is not limited to proteins: any interacting molecules may be used with this assay architecture. Also, the omni-directional encoded microparticles of the present invention may be used in conjunction with any other encoded particles including but not limited to fluorophores, quantum dots, latex or glass beads, colloidal metal particles, spectroscopically active particles, SERS particles, or semiconductor nanorods.

The encoded microparticles may be used in conjunction with a 2D planar array of molecules. Interaction between molecules on the surface of the particles and those contained in spots on the 2D planar array are determined by the binding of the particles to the spots. The presence of the particles in the predetermined spot locations, preferably after washing steps, indicates a binding interaction between the molecules on the particles and the molecules on the 2D planar array. The assay result can be determined by identifying 1) the particle code, and 2) the spot location. This is shown in FIG. 51. FIG. 51 is a schematic that includes images of particles but is not the result of an actual experiment, i.e. meant to serve as an illustration of this invention. In this invention, the square cross section of the microparticles of the present invention provide for increased binding contact area and is a significant improvement over the prior art.

The microparticles of the invention may have other applications. For example, by placing protein-detection molecules (e.g., ligands, dyes which change color, fluoresce, or cause electronic signal upon contact with specific protein molecules) onto the microparticles, bioassay analyses can be performed (i.e., evaluation of the protein and/or gene expression levels in a biological sample). As another example, by placing (cellular) receptors, nucleic acids/probes, oligonucleotides, adhesion molecules, messenger RNA (specific to which gene is "turned on" in a given disease state), cDNA (complementary to mRNA coded-for by each gene that is "turned on"), oligosaccharides & other relevant carbohydrate molecules, or cells (indicating which cellular pathway is "turned on", etc.) onto the microparticles, the microparticles can be used to screen for proteins or other chemical compounds that act against a disease (i.e., therapeutic target); as indicated by (the relevant component from biological sample) adhesion or hybridization to specific spot (location) on the microarray where a specific (target molecule) was earlier placed/attached. In fact, the microparticles of the invention can be applied to many other biochemical or biomolecular fields, such as those set forth in the appendix attached herewith, the subject matter of each is incorporated herein by reference.

It will be appreciated by those of skill in the art that a new and useful microparticle and a method of making the same have been described herein. The large sets of encoded microparticles produced by this invention can be a fundamental technology that will have far reaching applications, especially in the field of biotechnology and more specifically genomics. It has the potential to dramatically reduce the cost of highly multiplexed bioassays. Moreover, enables researchers to easily design custom content solution arrays. The researcher can also easily add new particle types to the pooled set, for instance including new found genes of interest with the microparticles of the invention.

In view of the many possible embodiments to which the principles of this invention may be applied, however, it should be recognized that the embodiments described herein with respect to the drawing figures are meant to be illustrative only and should not be taken as limiting the scope of invention. Those of skill in the art will recognize that the illustrated embodiments can be modified in arrangement and detail without departing from the spirit of the invention.

For example, the microparticle may have a six sided shape with four elongated sides and two end sides. The encoded microparticle can be configured such that the code of the encoded microparticle can be detectable regardless of which of the four elongated sides the barcode is disposed on. The microparticle may have a ratio of the length to width is from 2:1 to 50:1, from 4:1 to 20:1. The length of the microparticle is preferably from 5 to 100 μm and more preferably less than 50 μm. The width of the microparticle can be from 0.5 to 10 μm. In other examples, the length of the microparticle can be less than 10 μm, less than 25 μm, less than 25 μm; less than 5 μm, less than 27 μm; and the width of the microparticle can be less than 3 μm. The ratio of width to height of the microparticle can be from 0.5 to 2.0. The ratio of the length to width of the microparticle can be from 2:1 to 50:1. The cross section taken along the length of the microparticle is substantially rectangular with a length at least twice the width.

The microparticle may have a glass body with segments embedded therein. The difference of the transmissivity of the glass body and segments can be 10% or more. The glass body may have a length of less than 50 μm and a width of less than 10 μm with the glass body having a volume of from 5 to 500 μm³. The encoded microparticle may have 2 to 15, 3 to 10, or 4 to 8 portions of less transparent material within the encoded microparticle. The code incorporated in the microparticle can be binary or non-binary or any other desired codes. The microparticle may have biochemical molecules attached to one or more surfaces of the microparticle, such as DNA and RNA probes with a density of from $10^2$ to $10^6$ μm². When fabricated on the wafer-level, the wafer may have a surface area of from 12.5 in² to 120 in², and wherein there are at least 3 million microparticles per m² of the wafer. The wafer may have at least one million codes are formed on the substrate, or at least two hundred different codes are present within the one million codes, or at least 3000 different codes are present within the one million codes. When placed in a liquid buffer, for example in a bioassay, the microparticles can form a single monolayer with a 2 dimensional diffusion coefficient of the microparticles greater than $1\times10^{-12}$ cm²/s and more preferably greater than $1\times10^{-11}$ cm²/s.

Therefore, the invention as described herein contemplates all such embodiments as may come within the scope of the following claims and equivalents thereof.

APPENDIX

The subject matter of each one of the following references is incorporated herein by reference in entirety:
Preparing Probe Immobilized Arrays
G. Steinberg, K. Stromsborg., et al. Strategies for Covalent Attachment of DNA to Beads. Biopolymers. Vol. 73, 597-605. Published online 17 Feb., 2004 in Wiley InterScience (www.interscience.wiley.com). DOI 10.1002/bip.20006.
Kumar, O. Larsson, D. Parodi, & Z. Liang. 2000. Silanized nucleic acids: a general platform for DNA immobilization. ucleic Acids Research, 2000, Vol. 28. No. 14.
F. Vianello, L. Zennaro, et. al. Preparation, Morphological Characterization, and Activity of Thin Films of Horseradish Peroxidase. Biotechnology and Bioengineering, Vol. 68, Nol 5., Jun. 5, 2000.
U. Maskos, & E. M. Southern. 1992. Oligonucleotide hybridixations on glass supports: a novel linker for oligonucleotide synthesis and hybridization properties of oligonucleotides synthesized in situ. Nucleic Acids Research, Vol. 20, No. 7 1679-1684.
M. Bele, O, Silman, & E. Matijevic. 2002. Preparation and Flow Cytometry of Uniform Silica-Fluorescent dye microspheres. Journal of Colloid and Interface Science. 254, 274-282.
N. Zammatteo, L. Jeanmart, et al. Comparison between Different Strategies of Covalent Attachment of DNA to Glass Surfaces to Build DNA Microarrays, Analytical Biochemistry. 280, 143-150 (2000)
N. P. Mellott, S. L. Brantley, et al. Evaluation of surface preparation methods for glass. Surface and interface Analysis. 2001; 31: 362-368
F. Diehl, S. Grahlmann, et al. Manufacturing DAN microarrays of high spot homogeneity and reduced background signal. Nucleic Acids Research, 2001, Vol. 29, No. 7 e38.
Particle Arrays
Nicewarner-Pena, S. R., R. G. Freeman, B. D. Reiss, L. He, D. J. Pena, I. D. Walton, R. Cromer, C. D. Keating, and M. J. Natan, "Submicrometer Metallic Barcodes," *Science,* 294 (5540), 137-141 (2001).
Natan, M. J., J. Lissack, "Barcoding Tackles the Nanometer," Tags and Labels"
Walton, I. D., S. M. Norton, A. Balasingham, L. He, D. F. Oviso, D. Gupta, P. A. Raju, M. J. Natan, and R. G. Freeman, "Particles for multiplexed analysis in solution: detection and identification of striped metallic particles using optical microscopy," *Anal. Chem.,* 74, 2240-2247 (2002).
True, R. J., M. K. Taylor, G. S. Chakarova, I. D. Walton, "Microfabricated templates for the electrodeposition of metallic barcodes for use in multiplexed bioassays," IEEE-EMB Proceedings, 26(IV), 2619-2622 (2004).
Xu, H. X., M. Y. Sha, E. Y. Wong, J. Uphoff, Y. H. Xu, J. A. Treadway, A. Truong, E. O'Brien, S. Asquith, M. Stubbins, et. al., "Multiplexed SNP genotyping using the Qbead™ system: a quantum dot-encoded microsphere-based assay," Nucleic Acids Res., 31(8), E43 (2003).
Han, M., X. Gao, J. Z. Su, S, Nie, "Quantum-dot-tagged microbeads for multiplexed optical coding of biomolecules," *Nat. Biotechnol.,* 19(7), 631-635 (2001).
Protein Arrays
Haab, B. B., M. J. Dunham, & P. O. Brown. 2001. Protein microarrays for highly parallel detection and quantitation of specific proteins and antibodies in complex solutions. Geneome Biology. 2(2): 0004.1-0004.13.
MacBeath, G., & S. L. Schreiber. 2000. Printint proteins as microarrays for high-throughput function determination. Science. 289; 1760-1763.
Zhu, H., J. F. Klemic, et al. 2000. Analysis of yeast protein kinases using protein chips. Nature Genetics. 26: 283-289.
Zhu, H., & M. Snyder. 2001. Protein arrays and microarrays. Current Opinion in Chemical Biology. 5: 40-45.
B. B. Haab, M. J. Dunham & P. O. Brown. Protein microarrays for highly parallel detection and quantitation of specific proteins and antibodies in complex solutions. Genome Biology 2001, 2(2) research 0004.1-0004.13
Glycan Arrays
Blixt, O; Head, S; Mondala, T; Scanlan, C; Huflejt, M E; Alvarez, R; Bryan, M C; Fazio, F; Calarese, D; Stevens, J; Razi, N; Stevens, D J; Skehel, J J; van Die, I; Burton, D R; Wilson, I A; Cummings, R; Bovin, N; Wong, C H; Paulson, J C. 2004 Printed covalent glycan array for ligand profiling of diverse glycan binding proteins. PROC NAT ACAD SCI USA 101:49 17033-17038

A focused microarray approach to functional glycomics: transcriptional regulation of the glycome. Comelli, E. M. et al. Glycobiology 16(2), 117-31, 2006

Glycomics investigation into insulin action. Parry, S. et al. Biochimica Et Biophysica Acta-General Subjects 1760(4), 652-68, 2006

Cancer Chips

Alizadeh. A. A., M. B. Eisen, et al. 2000. Distinct types of diffuse large B-cell lymphoma identified by gene expression profiling. Nature. 403: 503-511.

Ein-Dor, L., I. Kela, et al. 2005. Outcome signature genes in breast cancer: is there a unique set? Bioinformatics. 21(2): 171-178.

Ross, D. T., U. Scherf, et al. 2000. Systematic variation in gene expression patterns in human cancer cell lines. Nature Genetics. 24: 227-238.

Sorlie, T., R. Tibshirani, et al. 2003. Repeated observation of breast tumor subtypes in independent gene expression data sets. PNAS USA. 200: 8418-8423.

Aneuploidy Chips

Behr, M. A., M. A. Wilson, et al. 1999. Comparative genomics of BCG vaccines by whole-genome DNA microarray. Science. 284: 1520-1523.

Forozan, F., E. H. Mahlamaki, et al. 2000. Comparative genomic Hybridization analysis of 38 breast cancer cell lines: A basis for interpreting complementary DNA microarray data. Cancer Research. 60: 4519-4528.

Grimm, D. 2004. Disease back cancer origin theory. Science 306: 389.

Hughes, T. R., C. J. Roberts, et al. 2000. Widespread aneuploidy revealed by DNA microarray expression profiling. Nature Genetics. 25: 333-337

Leptin Chips

Belkin, L. 2000, Dec. 24. The making of an 8-year-old woman. How do we understand puberty? Through the prism of our times. New York Times magazine. 38-43.

Nohturfft, A., & R. Losick. 2002. Fats, flies and palmitate. Science. 296: 857-858.

Soukas, A., P. Cohen, et al. 2000. Leptin-specific patterns of gene expression in white adipose tissue. Genes and Development. 14: 963-980.

Microarray Fabrication Methods

Brown, P. O., et al. 2001. The Mguide. http://cmgm.stanford.edu/pbrown/mguide/. Accessed 8 Feb. 2002.

Kane, M. D., T. A. Jatkoe, et al. 2000. Assessment of the sensitivity and specificity of oligonucleotide (50mer) microarrays. Nucleic Acids Research. 28(22): 4552-4557.

Kumar, A., & A. Liang. 2001. Chemical nanoprinting: A novel method for fabricating DNA microchips. Nucleic Acids Research 29(2): e2.

Okamoto, T., T. Suzuki, & N. Yamamoto. 2000. Microarray fabrication with covalent attachment of DNA using bubble jet technology. Nature Biotechnology. 18: 438-441.

Harris, T. M., A. Massimi, & G. Childs. 2000. Injecting new ideas into microarray printing. Nature Biotechnology. 18:384-385.

General References

Cummings, C. A., & D. Relman. 2000. Using DNA microarrays to study host-microbe interactions. Genomics. 6(5): 513-525.

Schaffer, J. L., M. Perez-Amador, & E. Wisman, 2000. Monitoring genome-wide expression in plants. Current Opinion in Biotechnology. 11: 162-167

Lockhart, D. J., & C. Barlow. 2001. Expressing what's on your mind: DNA arrays and the brain. Nature Reviews. 2: 63-68.

Shoemaker, D. D., E. E. Schadt, et al. 2001. Experimental annotation of the human genome using microarray technology. Nature. 409: 922-927.

Dalton, R. 2000. DIY (Do it yourself) microarrays promise DNA chips with everything. Nature. 403: 236

DeRisi, J. L. V. R. Iyer, & P. O. Brown 1997. Exploring the metabolic and genetic control of gene expression on a genomic scale. Science. 278:680-686.

Gasch, A. P., P. T. Spellman, et al. 2000. Genomic expression programs in the response of yeast cells to environmental changes. Molecular Biology of the Cell. 11: 4241-4257

Geschwind, D. H. 2000. Mice, microarrays, and the genetic diversity of the brain. PNAS. 97: 10676-10678.

R. Drmanac, S. Drmanac, G. Chui, et al. Sequencing by Hybridization (SBH): Advantages, Achievements, and Opportunities. Advanced in Biochemical Engineering/Biotechnology, Vol. 77, 75-100.

Membrane Chips

Fang Y, Frutos A G, Webb B, Hong Y, Ferrie A, Lai F, Lahiri J. Membrane biochips. Biotechniques. 2002 December; Suppl:62-5. PMID: 12514931

Fang Y, Frutos A G, Lahiri J. G-protein-coupled receptor microarrays. Chembiochem. 2002 Oct. 4; 3(10):987-91. PMID: 12362364

Fang Y, Frutos A G, Lahiri J. Membrane protein microarrays. J Am Chem. Soc. 2002 Mar. 20; 124(11):2394-5. PMID: 11890761

Fang Y, Webb B, Hong Y, Ferrie A, Lai F, Frutos A G, Lahiri J. Fabrication and application of G protein-coupled receptor microarrays. Methods Mol. Biol. 2004; 264:233-43. PMID: 15020794

Fang Y, Lahiri J, Picard L. G protein-coupled receptor microarrays for drug discovery. Drug Discov Today. 2003 Aug. 15; 8(16):755-61. Review. PMID: 12944098

Mishina Y M, Wilson C J, Bruett L, Smith J J, Stoop-Myer C, Jong S, Amaral L P, Pedersen R, Lyman S K, Myer V E, Kreider B L, Thompson C M. Multiplex GPCR assay in reverse transfection cell microarrays. J Biomol Screen. 2004 April; 9(3):196-207. PMID: 15140381

Mack J. Fulwyler and Thomas M. McHugh, "Flow Microsphere Immunoassay for the Quantitative and Simultaneous Detection of Multiple Soluble Analytes," Methods In Cell Biology, vol. 33, pp. 613-619.

Fulwyler et al, "Immunorealtive Bead (IRB) Assay for the Quantative and Simultaneous Flow Cytometric Detection of Multiple Analytes", Cytometry, Supplement 2, p. 19, Sep. 2, 1988.

Fulwyler et al., "Flow Micropheres Immunoassay for the Quantitative and Simultaneous Detection of Multiple Soluble Analytes," Methods in Cell Biology, 33, 613-629 (1990).

Vener et al., "A Novel Approach to Nonradioactive Hybridization Assay of Nucleic Acids Using Stained Latex Particles," Analytical Biochemistry, 198, 308-311 (1991).

Wilson et al., "A New Microsphere-Based Immunofluorescence Assay Using Flow Cytometry," Journal of Immunological Methods, 107, 225-230 (1988).

Bayerl, T. M. & Bloom, M. Physical properties of single phospholipid bilayers adsorbed to micro glass beads. Biophys. J. 58, 357-362 (1990).

Buranda, T. et al. Biomimetic molecular assemblies on glass and mesoporous silica microbeads for biotechnology. Langmuir 19, 1654-1663 (2003).

Pathogen Detection

Seung Min Yoo, Ki Chang Keum, et al. 2004. Development of DNA Microarray for Pathogen Detection. Biotechnology and Bioprocess Engineering. 9: 93-99

Call D R, Borucki M K, Loge F J. Detection of bacterial pathogens in environmental samples using DNA microarrays. J Microbiol Methods. 2003 May; 53(2):235-43. Review. PMID: 12654494

Somer L, Kashi Y. A PCR method based on 16S rRNA sequence for simultaneous detection of the genus *Listeria* and the species *Listeria monocytogenes* in food products. J Food Prot. 2003 September; 66(9):1658-65. PMID: 14503721

Warsen A E, Krug M J, LaFrentz S, Stanek D R, Loge F J, Call D R. Simultaneous discrimination between 15 fish pathogens by using 16S ribosomal DNA PCR and DNA microarrays. Appl Environ Microbiol. 2004 July; 70(7):4216-21. PMID: 15240304

Maynard C, Berthiaume F, Lemarchand K, Harel J, Payment P, Bayardelle P, Masson L, Brousseau R. Waterborne pathogen detection by use of oligonucleotide-based microarrays. Appl Environ Microbiol. 2005 December; 71(12):8548-57. PMID: 16332846

Gonzalez S F, Krug M J, Nielsen M E, Santos Y, Call D R. Simultaneous detection of marine fish pathogens by using multiplex PCR and a DNA microarray. J Clin Microbiol. 2004. April; 42(4):1414-9. PMID: 15070982

M. T. McBride, S. M. Messenger, T. R. Slezak, & P. M. Imbro. Tailored assays for the detection of foreign disease pathogens in animals. IVD Technology, May 2005

Small RNA

Remodelling of the *Escherichia coli* outer membrane by two small regulatory RNAs "Guillier, M. et al. Molecular Microbiology 59(1), 231-47, 2006

Genes for small, noncoding RNAs under sporulation control in *Bacillus subtilis* Silvaggi, J. M. et al. Journal of Bacteriology 188(2), 532-41, 2006

Comparative RNA expression analyses from small-scale, single-donor platelet samples Hillmann, A. G. et al. Journal of Thrombosis and Haemostasis 4(2), 349-56, 2006

Optimization and validation of small quantity RNA profiling for identifying TNF responses in cultured human vascular endothelial cells Shou, H. Y. et al. Journal of Pharmacological and Toxicological Methods 53(2), 152-9, 2006

An antibody-based microarray assay for small RNA detection

Hu, Z. L. et al. Nucleic Acids Research 34(7), NPG, 2006

Notch3 gene amplification in ovarian cancer

Park, J. T. et al. Cancer Research 66(12), 6312-8, 2006

Dissecting the biological functions of *Drosophila* histone deacetylases by RNA interference and transcriptional profiling Foglietti, C. et al. Journal of Biological Chemistry 281(26), 17968-76, 2006 c-Myb is an essential downstream target for homeobox-mediated transformation of hematopoietic cells Hess, J. L. et al. Blood 108(1), 297-304, 2006

Localization of candidate regions for a novel gene for Kartagener syndrome

Gutierrez-Roelens, I. et al. European Journal of Human Genetics 14(7), 809-15, 2006

MicroRNA-targeted and small interfering RNA-mediated mRNA degradation is regulated by Argonaute, Dicer, and RNA-dependent RNA polymerase in *Arabidopsis*

Ronemus, M. et al. Plant Cell 18(7), 1559-74, 2006

Methylation

*High-Throughput DNA Methylation Profiling Using Universal Bead Arrays*, M. Bibikova, Z. Lin, L. Zhou, E. Chudin, E. Wickham Garcia, B. Wu, D. Doucet, N. J. Thomas, Y. Wang, E. Vollmer, T. Goldmann, C. Seifart, W. Jiang, D. L. Barker, M. S. Chee, J. A. Floros and J. B. Fan, Genome Research, 16 (3), 383-393, March 2006.

*Human Embryonic Stem Cells Have a Unique Epigenetic Signature*, M. Bibikova, E. Chudin, B. Wu, L. Zhou, E. Wickham Garcia, Y. Liu, S. Shin, T. W. Plaia, J. M. Auerbach, D. E. Arking, R. Gonzalez, J. Crook, B. Davidson, T. C. Schulz, A. Robins, A. Khanna, P. Sartipy, J. Hyllner, P. Vanguri, S. Savant-Bhonsale, A. K. Smith, A. Chakravarti, A. Maitra, M. Rao, D. L. Barker, J. F. Loring and J. B. Fan, Genome Research, Published online Aug. 9, 2006, 10.1101/gr.5319906.

Tagging

Summary of the Sensing and Positioning Technology, Workshop of the Committee on nanotechnology for Intelligence Community: Interim Report (2004), National Materials Advisory Board, Topic 1: Security Technologies Overview Desouza, K. C. Vanapalli, G. K. Securing Knowledge Assets and Processes: Lessons from the Defense and Intelligence Sectors System Sciences, 2005. HICSS '05. Proceedings of the 38th Annual Hawaii International Conference on Publication Date: 3-6 Jan. 2005

Books

D. Bowtell and J. Sambrook. 2003, DNA Microarrays, A Molecular Cloning Manual. Cold Spring Harbor Laboratory Press (in particular, sections 1-4)

G. T. Hermanson, Bioconjugate Techniques, 1996, Academic Press (Parts 1, 2 and 3 are all directly applicable)

Hacia J, Brody L, Chee M, et al. "Detection of heterozygous mutations in BRCA1 using high density oligonucleotide arrays and two-color fluorescence Analysis" Nat Genet, 1996, 14, 441.

Hacia J, Edgemon K, Sun B et al. "Two color hybridization analysis using high density oligonucleotide arrays and energy transfer dyes" Nucleic Acids Res, 1998, 26, 4249.

Hacia J. "Resequencing and mutation analysis using oligonucleotides microarrays" Nature Genetics (Supplement), 1999, 21, 42.

Wodicka L et al. "Genome-wide expression monitoring in *Saccharomyces cerevisiae*" Nature Biotechnology, 1997, 15, 1359.

Lockhart D et al. "Expression monitoring by hybridization to high-density oligonucleotide arrays" Nature Biotechnology, 1997, 14, 1675.

DeRisi J. et al. "Use of a cDNA microarray to analysis gene expression patterns in human cancer" Nat Genet, 1996, 14, 457.

Brown P O, Botstein D. "Exploring the new world of genome with DNA microarrays" Nature Genetics (Supplement), 1999, 21, 33.

Jelinsky S and Samson L. "Global response of *Saccharomyces cerevisiae* to a alkylating agent" proc. Natl Acad Sci USA, 1999, 96, 486.

Golub T. et al., 1999, "Molecular Classification of cancer: Class Discovery and Prediction by Gene Expression Monitoring" Science, 1999, 286, 531.

Heller R A, Schena M, Chai A, et al. "Discovery and analysis of inflammatory disease-related genes using cDNA microarrays" Proc Natl Acad Sci USA, 1997, 94, 2150.

Wang D, Fan J, Siao C et al. "Large-scale identification, mapping and genotyping of single-nucleotide polymorphism in human genome" Science, 1998, 280, 1077.

Lipshutz R J, Morris D, Chee M, et al. "Using oligonucleotide probe arrays to access genetic diversity" Bio Feature, 1995, 19(3), 442.

Wallraff G., Labadie J., Brock P. et al. "DNA Sequencing on a Chip" Chemtech, 1997, 22, 32.

What is claimed is:

1. A method of forming an encoded microparticle, the method comprising:

depositing and patterning a plurality of layers on a substrate so as to form a plurality of microparticles, each microparticle comprising a plurality of separate segments aligned along an axis and representing a code; and releasing the microparticles in order to separate the microparticles from the substrate.

2. The method of claim 1, wherein depositing and patterning the plurality of layers further comprises:

depositing a first layer on the substrate;

depositing a second layer on the first layer;

forming the second layer into a plurality of particle regions such that each particle region has two or more discrete segments aligned along the axis; and depositing a third layer after forming the second layer.

3. The method of claim 1, wherein depositing and patterning the plurality of layers further comprises:

depositing a first layer on the substrate;

depositing a second layer on the first layer;

forming, at a first time, a first pattern on the second layer;

forming, at a second time, a second pattern on the second layer; and wherein the first and second patterns form all or a portion of the code of the microparticle.

4. The method of claim 1, wherein the microparticle comprises a transparent material.

5. The method of claim 1, wherein the discrete segments of the microparticle are opaque.

6. The method of claim 5, wherein the discrete segments comprise a semiconductor or metal.

7. The method of claim 1, wherein a cross section of the microparticle is substantially rectangular.

8. The method of claim 1, wherein a volume of the microparticle is 20,000 cubic microns or less.

9. The method of claim 1, wherein a length of the microparticle is 160 microns or less.

10. The method of claim 1, wherein a width of the microparticle is 70 microns or less.

11. The method of claim 1, further comprising:

forming a layer that comprises a material selected from the group consisting of a magnetic, ferromagnetic, diamagnetic, paramagnetic, and a superparamagnetic material.

12. The method of claim 1, further comprising:

forming a fluorescent layer composed of a plurality of fluorescent molecules.

13. The method of claim 1, further comprising:

attaching a multiplicity of biochemical molecules on or in a surface microparticle.

14. A method of producing an encoded particle comprising:

providing a substrate;

depositing a first layer on the substrate;

depositing a second layer on the first layer;

forming the second layer into a plurality of particle regions such that each particle region has two or more discrete segments aligned along an axis, wherein a code is formed by the discrete segments of an individual particle;

depositing a third layer after forming the second layer; and releasing the layers in the particle regions from the substrate to form individual particles.

15. The method of claim 14, wherein the step of patterning the second layer comprises:

forming, at a first time, a first pattern on the second layer;

forming, at a second time, a second pattern on the second layer; and wherein the first and second patterns form all or a portion of the code of the particle.

16. The method of claim 14, wherein the first layer comprises a transparent material.

17. The method of claim 14, wherein the second layer comprises an opaque material.

18. The method of claim 14, wherein the second layer comprises a material selected from the group consisting of a magnetic, ferromagnetic, diamagnetic, paramagnetic, and a superparamagnetic material.

19. The method of claim 14, wherein the volume of the particle is 20,000 cubic microns or less.

20. The method of claim 14, wherein a length of the particle is 160 microns or less.

21. The method of claim 14, wherein a width of the particle is 70 microns or less.

22. The method of claim 14, further comprising:

forming a fluorescent layer composed of a plurality of fluorescent molecules.

23. The method of claim 14, further comprising:

attaching a multiplicity of biochemical molecules on or in a surface of the particle.

24. A method of forming a plurality of encoded microparticles, comprising:

depositing and patterning a layer on a substrate so as to form a plurality of microparticles, each comprising a plurality of discrete segments aligned along an axis which is substantially parallel to the substrate and representing a code; and releasing the microparticles in order to separate the microparticles from the substrate, wherein the code for each microparticle is detectable from all directions perpendicular to the axis.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: 2-plex DNA hybridization assay oligo probe
<220> FEATURE:
<221> NAME/KEY: misc_feature
<222> LOCATION: (1)..(1)
<223> OTHER INFORMATION: May be modified with a 5' Amino Modifier C6
      moiety

<400> SEQUENCE: 1
aaatcatcgg gagcattgtg                                              20

<210> SEQ ID NO 2
<211> LENGTH: 20
<212> TYPE: DNA
<213> ORGANISM: Artificial Sequence
<220> FEATURE:
<223> OTHER INFORMATION: 2-plex DNA hybridization assay oligo probe
<220> FEATURE:
<221> NAME/KEY: misc_feature
<222> LOCATION: (1)..(1)
<223> OTHER INFORMATION: May be modified with a 5' Cy3 moiety

<400> SEQUENCE: 2
cacaatgctc ccgatgattt                                              20

<210> SEQ ID NO 3
<211> LENGTH: 20
<212> TYPE: DNA
<213> ORGANISM: Artificial Sequence
<220> FEATURE:
<223> OTHER INFORMATION: 2-plex DNA hybridization assay oligo probe
<220> FEATURE:
<221> NAME/KEY: misc_feature
<222> LOCATION: (1)..(1)
<223> OTHER INFORMATION: May be modified with a 5' Amino Modifier C6
      moiety

<400> SEQUENCE: 3
aacgcctggt cactgctatt                                              20

<210> SEQ ID NO 4
<211> LENGTH: 20
<212> TYPE: DNA
<213> ORGANISM: Artificial Sequence
<220> FEATURE:
<223> OTHER INFORMATION: 2-plex DNA hybridization assay oligo probe
<220> FEATURE:
<221> NAME/KEY: misc_feature
<222> LOCATION: (1)..(1)
<223> OTHER INFORMATION: May be modified with a 5' Cy3 moiety

<400> SEQUENCE: 4
aatagcagtg accaggcgtt                                              20